US011351222B2

(12) United States Patent
Pei et al.

(10) Patent No.: US 11,351,222 B2
(45) Date of Patent: Jun. 7, 2022

(54) DI-SULFIDE CONTAINING CELL PENETRATING PEPTIDES AND METHODS OF MAKING AND USING THEREOF

(71) Applicant: Ohio State Innovation Foundation, Columbus, OH (US)

(72) Inventors: Dehua Pei, Columbus, OH (US); Ziqing Qian, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/348,706

(22) PCT Filed: Nov. 9, 2017

(86) PCT No.: PCT/US2017/060881
§ 371 (c)(1),
(2) Date: May 9, 2019

(87) PCT Pub. No.: WO2018/089648
PCT Pub. Date: May 17, 2018

(65) Prior Publication Data
US 2019/0282654 A1    Sep. 19, 2019

Related U.S. Application Data

(60) Provisional application No. 62/419,781, filed on Nov. 9, 2016, provisional application No. 62/425,550, filed on Nov. 22, 2016, provisional application No. 62/438,141, filed on Dec. 22, 2016.

(51) Int. Cl.
| A61K 38/12 | (2006.01) |
| C07K 5/10  | (2006.01) |
| C07K 7/06  | (2006.01) |
| C07K 7/08  | (2006.01) |
| C07K 7/50  | (2006.01) |
| A61K 38/00 | (2006.01) |
| C07K 14/00 | (2006.01) |

(52) U.S. Cl.
CPC ............... *A61K 38/12* (2013.01); *C07K 5/10* (2013.01); *C07K 7/06* (2013.01); *C07K 7/08* (2013.01); *C07K 7/50* (2013.01); *C07K 14/001* (2013.01); *A61K 38/00* (2013.01)

(58) Field of Classification Search
None
See application file for complete search history.

(56) References Cited

U.S. PATENT DOCUMENTS

| 5,804,558 | A  | 9/1998  | Lehrer et al. |
| 6,864,355 | B1 | 3/2005  | May et al. |
| 6,960,648 | B2 | 11/2005 | Bonny |
| 7,850,949 | B2 | 12/2010 | Fang |
| 9,868,767 | B2 | 1/2018  | Pei et al. |
| 10,501,496 | B2 | 12/2019 | Pei et al. |
| 10,626,147 | B2 | 4/2020  | Pei et al. |
| 10,738,093 | B2 | 8/2020  | Qian et al. |
| 2002/0035243 | A1 | 3/2002 | Imfeld |
| 2002/0120100 | A1 | 8/2002 | Bonny |
| 2003/0032594 | A1 | 2/2003 | Bonny |
| 2004/0014669 | A1 | 1/2004 | Selsted et al. |
| 2007/0041904 | A1 | 2/2007 | Jiang et al. |
| 2010/0292148 | A1 | 11/2010 | Krippner et al. |
| 2014/0294942 | A1 | 10/2014 | French et al. |
| 2015/0297742 | A1 | 10/2015 | Strieker et al. |
| 2016/0115202 | A1 | 4/2016 | Pei et al. |
| 2016/0235807 | A1 | 8/2016 | Shailubhai |
| 2016/0271216 | A1 | 9/2016 | Kemper et al. |
| 2017/0190743 | A1 | 7/2017 | Pei et al. |
| 2017/0355730 | A1 | 12/2017 | Pei et al. |
| 2018/0030094 | A1 | 2/2018 | Pei et al. |
| 2019/0282654 | A1 | 9/2019 | Pei et al. |
| 2019/0284240 | A1 | 9/2019 | Pei et al. |
| 2020/0291070 | A1 | 9/2020 | Pei |

FOREIGN PATENT DOCUMENTS

| EP | 2420255       | 2/2012  |
| WO | 2001052875    | 7/2001  |
| WO | 2008134761    | 11/2008 |
| WO | 2009098450    | 8/2009  |
| WO | 2014053882    | 4/2014  |
| WO | 2015051030    | 4/2015  |
| WO | 2015/179691 A2 | 11/2015 |
| WO | 2016054510    | 4/2016  |

(Continued)

OTHER PUBLICATIONS

Extended European Search Report issued in EP 14800563.0 dated Nov. 17, 2016.
Non-Final Office Action issued in U.S. Appl. No. 14/893,203, dated Dec. 6, 2016.
Restriction Requirement issued in U.S. Appl. No. 16/462,920, dated Apr. 13, 2020.
Non-Final Office Action issued in U.S. Appl. No. 16/762,914, dated Apr. 17, 2020.

(Continued)

*Primary Examiner* — Thomas S Heard
(74) *Attorney, Agent, or Firm* — Meunier Carlin & Curfman LLC

(57) ABSTRACT

Disclosed is a general, reversible bicyclization strategy to increase both the proteolytic stability and cell permeability of peptidyl drugs. A peptide drug is fused with a short cell-penetrating motif and converted into a conformationally constrained bicyclic structure through the formation of a pair of disulfide bonds. The resulting bicyclic peptide has greatly enhanced proteolytic stability as well as cell-permeability. Once inside the cell, the disulfide bonds are reduced to produce a linear, biologically active peptide. This strategy was applied to generate a cell-permeable bicyclic peptidyl inhibitor against the NEMO-IKK interaction.

18 Claims, 26 Drawing Sheets

Specification includes a Sequence Listing.

(56) References Cited

FOREIGN PATENT DOCUMENTS

| WO | 2017/109076 A1 | 6/2017 |
|---|---|---|
| WO | 2018098231 | 5/2018 |

OTHER PUBLICATIONS

Srinivas et al., Biaryl amino acid templates in place of D-Pro-L-Pro in cyclic beta-hairpin cationic antimicrobial peptidemimetics. Organic and Biomolecular Chemistry. vol. 5, pp. 3100-3105, 2007.
Non-Final Office Action issued in U.S. Appl. No. 16/462,920, dated Aug. 18, 2020.
Almarsson, Örn, and Michael J. Zaworotko. "Crystal engineering of the composition of pharmaceutical phases. Do pharmaceutical co-crystals represent a new path to improved medicines?" Chemical communications 17 (2004): 1889-1896.
Alzani, R. et al. "Suramin induces deoligomerization of human tumor necrosis factor alpha." J. Biol. Chem. 268, (1993): 12526-12529.
Angelini, Alessandro, et al. "Bicyclic peptide inhibitor reveals large contact interface with a protease target." ACS chemical biology 7.5 (2012): 817-821.
Appelbaum, Jacob S., et al. "Arginine topology controls escape of minimally cationic proteins from early endosomes to the cytoplasm." Chemistry & biology 19.7 (2012): 819-830.
Ardi, V. C., et al., "Macrocycles that inhibit the binding between heat shock protein 90 and TPR-containing proteins." ACS Chem. Biol. 6, (2011): 1357-1366.
Baud, Véronique, and Michael Karin. "Is NF-κB a good target for cancer therapy? Hopes and pitfalls." Nature reviews Drug discovery 8.1 (2009): 33.
Beste, G. et al. "Small antibody-like proteins with prescribed ligand specificities derivedfrom the lipocalin fold." Proc. Natl. Acad. Sci. USA 96, (1999): 1898-1903.
Beutler, B. et al. "Purification of cachectin, a lipoprotein-lipase suppressing hormone secreted by endotoxin-induced RAW 264.7 cells." J. Exp. Med. 161, (1985): 984-995.
Birts, C. N. et al. "A cyclic peptide inhibitor of C-terminal binding protein dimerization links metabolism with mitotic fidelity in breast cancer cells." Chem. Sci., 4, (2013): 3046-3057.
Buller, F., et al. "Discovery of TNF inhibitors from a DNA-encoded chemical library based on Diels-Alder cycloaddition." Chem. Biol. 16, (2009): 1075-1086.
Chan, D. S. et al. "Structure-based discovery of natural-product-like TNF-a inhibitors." Angew. Chem. Int. Ed. Engl. 49, (2010): 2860-2864.
Chatterjee, Jayanta, et al. "N-methylation of peptides: a new perspective in medicinal chemistry." Accounts of chemical research 41.10 (2008): 1331-1342.
Chen, G. & Goeddel, D. V. "TNF-R1 signaling: a beautiful pathway." Science 296, (2002): 1634-1635.
Chen, S., et al., "Structurally diverse cyclization linkers impose different backbone conformations in bicyclic peptides." ChemBioChem. 13, (2012): 1032-1038.
Chen, X., Tan, P. H., Zhang, Y. & Pei, D. "On-bead screening of combinatorial libraries: Reduction of nonspecific binding by decreasing surface ligand density." J. Comb. Chem. 11, (2009): 604-611.
Cheng, Seng H., et al. "Defective intracellular transport and processing of CFTR is the molecular basis of most cystic fibrosis." Cell 63.4 (1990): 827-834.
Choi, H., et al., "Discovery of the inhibitors of tumor necrosis factor alpha with structure-based virtual screening." Bioorg. Med. Chem. Lett. 20, (2010): 6195-6198.
Cildir, Gökhan, Kee Chung Low, and Vinay Tergaonkar. "Noncanonical NF-κB signaling in health and disease." Trends in molecular medicine 22.5 (2016): 414-429.
Cochran, Andrea G., Nicholas J. Skelton, and Melissa A. Starovasnik. "Tryptophan zippers: Stable, monomeric β-hairpins." Proceedings of the National Academy of Sciences 98.10 (2001): 5578-5583.
Cooley, Christina B., et al. "Oligocarbonate molecular transporters: oligomerization-based syntheses and cell-penetrating studies." Journal of the American Chemical Society 131.45 (2009): 16401-16403.
Craik, David J., et al. "The future of peptide-based drugs." Chemical biology & drug design 81.1 (2013): 136-147.
Cushing, Patrick R., et al. "A Stabilizing Influence: CAL PDZ Inhibition Extends the Half-Life of ΔF508-CFTR." Angewandte Chemie International Edition 49.51 (2010): 9907-9911.
Dai, Simon, et al. "The IκB kinase (IKK) inhibitor, NEMO-binding domain peptide, blocks osteoclastogenesis and bone erosion in inflammatory arthritis." Journal of Biological Chemistry 279.36 (2004): 37219-37222.
Davé, Shaival H., et al. "Amelioration of chronic murine colitis by peptide-mediated transduction of the IκB kinase inhibitor NEMO binding domain peptide." The Journal of Immunology 179.11 (2007): 7852-7859.
Delfín, Dawn A., et al. "Improvement of cardiac contractile function by peptide-based inhibition of NF-κB in the utrophin/dystrophin-deficient murine model of muscular dystrophy." Journal of translational medicine 9.1 (2011): 68.
Deshayes, Sebastien, et al. "Cell-penetrating peptides: tools for intracellular delivery of therapeutics." Cellular and Molecular Life Sciences CMLS 62.16 (2005): 1839-1849.
Desimmie, B. A. et al. "Phage Display-directed Discovery of LEDGF/p75 Binding Cyclic Peptide Inhibitors of HIV Replication." Mol. Therapy 20, (2012): 2064-2075.
Dewan, V. et al. "Cyclic peptide inhibitors of HIV-I capsid-human lysyl-tRNA synthetase interaction." ACS Chem. Biol. 7, (2012):761-769.
Dong et al., A Photocontrolled β-Hairpin Peptide. Chemistry—A European Journal. 2006, 12(4): 1114 1120.
Duchardt, Falk, et al. "A comprehensive model for the cellular uptake of cationic cell-penetrating peptides." Traffic 8.7 (2007): 848-866.
Eguchi, Akiko, et al. "Protein transduction domain of HIV-1 Tat protein promotes efficient delivery of DNA into mammalian cells." Journal of Biological Chemistry 276.28 (2001): 26204-26210.
Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.
El Andaloussi, Samir, et al. "Design of a peptide-based vector, PepFect6, for efficient delivery of siRNA in cell culture and systemically in vivo." Nucleic acids research 39.9 (2011): 3972-3987.
El-Sayed, Ayman, Shiroh Futaki, and Hideyoshi Harashima. "Delivery of macromolecules using arginine-rich cell-penetrating peptides: ways to overcome endosomal entrapment." The AAPS journal 11.1 (2009): 13-22.
Engelman, D. M., T. A. Steitz, and A. Goldman. "Identifying nonpolar transbilayer helices in amino acid sequences of membrane proteins." Annual review of biophysics and biophysical chemistry 15.1 (1986): 321-353.
Esposito, E. & Cuzzocrea, S. "TNF-alpha as a therapeutic target in inflammatory diseases, ischemia-reperfusion injury and trauma." Curr. Med. Chem. 16, (2009): 3152-3167.
Ferrari, Aldo, et al. "Caveolae-mediated internalization of extracellular HIV-1 tat fusion proteins visualized in real time." Molecular therapy 8.2 (2003): 284-294.
Fittipaldi, Antonio, et al. "Cell membrane lipid rafts mediate caveolar endocytosis of HIV-1 Tat fusion proteins." Journal of Biological Chemistry 278.36 (2003): 34141-34149.
Fosgerau, Keld, and Torsten Hoffmann. "Peptide therapeutics: current status and future directions." Drug discovery today 20.1 (2015): 122-128.
Frankel, Alan D., and Carl O. Pabo. "Cellular uptake of the tat protein from human immunodeficiency virus." Cell 55.6 (1988): 1189-1193.
Furka, A., et al. "General method for rapid synthesis of multicomponent peptide mixtures." Int. J. Pep. Prat. Res. 37, (1991): 487-493.
Futaki, Shiroh. "Membrane-permeable arginine-rich peptides and the translocation mechanisms." Advanced drug delivery reviews 57.4 (2005): 547-558.

(56) References Cited

OTHER PUBLICATIONS

Gaurnier-Hausser, Anita, et al. "NEMO-binding domain peptide inhibits constitutive NF-κB activity and reduces tumor burden in a canine model of relapsed, refractory diffuse large B-cell lymphoma." Clinical Cancer Research 17.14 (2011): 4661-4671.
Gotoh, Yusuke, et al. "A homogeneous time-resolved fluorescence-based high-throughput screening system for discovery of inhibitors of IKKβ-NEMO interaction." Analytical biochemistry 405.1 (2010): 19-27.
Goun, Elena A., et al. "Molecular transporters: synthesis of oligoguanidinium transporters and their application to drug delivery and real-time imaging." Chem Bio Chem 7.10 (2006): 1497-1515.
Green, Maurice, and Paul M. Loewenstein. "Autonomous functional domains of chemically synthesized human immunodeficiency virus tat trans-activator protein." Cell 55.6 (1988): 1179-1188.
Guo, Bingqian, et al. "Protein engineering of the N-terminus of NEMO: structure stabilization and rescue of IKKβ binding." Biochemistry 53.43 (2014): 6776-6785.
Gupta, Bhawna, Tatiana S. Levchenko, and Vladimir P. Torchilin. "Intracellular delivery of large molecules and small particles by cell-penetrating proteins and peptides." Advanced drug delivery reviews 57.4 (2005): 637-651.
Gupta, Subash C., et al. "Inhibiting NF-κB activation by small molecules as a therapeutic strategy." Biochimica et Biophysica Acta (BBA)—Gene Regulatory Mechanisms 1799.10-12 (2010): 775-787.
Hancock R., et al., Peptide inhibitors of the Keap1-Nrf2 protein-protein interaction. Free Radic. Biol. Med. 52, (2012):444-451.
He, M. M. et al. "Small-molecule inhibition of TNF-a." Science 310, (2005): 1022-1025.
Heinis, C., Rutherford, T., Freund, S. & Winter, G. "Phage-encoded combinatorial chemical libraries based on bicyclic peptides." Nat. Chem. Biol. 5, (2009): 502-507.
Herce, H. D., et al. "Arginine-rich peptides destabilize the plasma membrane, consistent with a pore formation translocation mechanism of cell-penetrating peptides." Biophysical journal 97.7 (2009): 1917-1925.
Herce, Henry D., and Angel E. Garcia. "Molecular dynamics simulations suggest a mechanism for translocation of the HIV-1 TAT peptide across lipid membranes." Proceedings of the National Academy of Sciences 104.52 (2007): 20805-20810.
Herndon, Thomas M., et al. "US Food and Drug Administration approval: carfilzomib for the treatment of multiple myeloma." Clinical cancer research 19.17 (2013): 4559-4563.
Herrington, Felicity D., Ruaidhri J. Carmody, and Carl S. Goodyear. "Modulation of NF-κB signaling as a therapeutic target in autoimmunity." Journal of biomolecular screening 21.3 (2016): 223-242.
Hintersteiner, M. et al. "Single bead labeling method for combining confocal fluorescence on-bead screening and solution validation of tagged one-bead one-compound libraries." Chem. Biol. 16, (2009): 724-735.
Hirose, Hisaaki, et al. "Transient focal membrane deformation induced by arginine-rich peptides leads to their direct penetration into cells." Molecular Therapy 20.5 (2012): 984-993.
Hopp, Thomas P., and Kenneth R. Woods. "Prediction of protein antigenic determinants from amino acid sequences." Proceedings of the National Academy of Sciences 78.6 (1981): 3824-3828.
Houghten, R. A et al. "Generation and use of synthetic peptide combinatorial libraries for basic research and drug discovery." Nature 354, (1991): 84-86.
Hoyer, J. A. N., and Ines Neundorf. "Peptide vectors for the nonviral delivery of nucleic acids." Accounts of chemical research 45.7 (2012): 1048-1056.
Hu, B. H., Jones, M. R. & Messersmith, P. B. "Method for screening and MALDI-TOF MS sequencing of encoded combinatorial libraries." Anal. Chem. 79, (2007): 7275-7285.
Huang, H-C., Truyen Nguyen, and Cecil B. Pickett. "Regulation of the antioxidant response element by protein kinase C-mediated phosphorylation of NF-E2-related factor 2." Proceedings of the National Academy of Sciences 97.23 (2000): 12475-12480.

Inoyama, Daigo, et al. "Optimization of fluorescently labeled Nrf2 peptide probes and the development of a fluorescence polarization assay for the discovery of inhibitors of Keap1-Nrf2 interaction." Journal of biomolecular screening 17.4 (2012): 435-447.
Ishii, Tetsuro, et al. "Transcription factor Nrf2 coordinately regulates a group of oxidative stress-inducible genes in macrophages." Journal of Biological Chemistry 275.21 (2000): 16023-16029.
Janin, J. O. E. L. "Surface and inside volumes in globular proteins." Nature 277, 5696 (1979): 491.
Jeong, Ji Hoon, et al. "siRNA conjugate delivery systems." Bioconjugate chemistry 20.1 (2008): 5-14.
Jimi, Eijiro, et al. "Selective inhibition of NF-κB blocks osteoclastogenesis and prevents inflammatory bone destruction in vivo." Nature medicine 10.6 (2004): 617.
Joo, S. H., Xiao, Q., Ling, Y., Gopishetty, B. & Pei, D. "High-throughput sequence determination of cyclic peptide library members by partial Edman degradation/mass spectrometry." J. Am. Chem. Soc. 128, (2006): 13000-13009.
Josephson, Lee, et al. "High-efficiency intracellular magnetic labeling with novel superparamagnetic-Tat peptide conjugates." Bioconjugate chemistry 10.2 (1999): 186-191.
Kansanen, Emilia, et al. "The Keap1-Nrf2 pathway: mechanisms of activation and dysregulation in cancer." Redox biology 1.1 (2013): 45-49.
Kaplan, Ian M., Jehangir S. Wadia, and Steven F. Dowdy. "Cationic TAT peptide transduction domain enters cells by macropinocytosis." Journal of Controlled Release 102.1 (2005): 247-253.
Kawakami, M., & Cerami, A. Studies of endotoxin-induced decrease in lipoprotein-lipase activity. J. Exp. Med. 154, (1981): 631-639.
Kerem, Bat-sheva, et al. "Identification of the cystic fibrosis gene: genetic analysis." Science 245.4922 (1989): 1073-1080.
Khabar, K. S., Siddiqui, S. & Armstrong, J. A. "WEHI-13V AR: a stable and sensitive variant of WEHI 164 clone 13 fibrosarcoma for tumor necrosis factor bioassay." Immunol. Lett. 46, (1995): 107-110.
Khakshoor, Omid, and James S. Nowick. "Artificial β-sheets: chemical models of β-sheets." Current opinion in chemical biology 12.6 (2008): 722-729.
Kimber, Matthew S., et al. "Structural basis for specificity switching of the Src SH2 domain." Molecular cell 5.6 (2000): 1043-1049.
Kodadek, T. & Bachhawat-Sikder, K. "Optimized protocols for the isolation of specific protein-binding peptides or peptoids from combinatorial libraries displayed on beads." Mol. BioSyst. 2, (2006): 25-35.
Koide, A. et al. "The fibronectin type III domain as a scaffold for novel binding proteins." J. Mol. Biol. 284, (1998): 1141-1151.
Kornegay, Joe N., et al. "NBD delivery improves the disease phenotype of the golden retriever model of Duchenne muscular dystrophy." Skeletal muscle 4.1 (2014): 18.
Kriegler, M. et al. "A Novel Form of TNF/cachectin Is a Cell Surface Cytotoxic Transmembrane Protein: Ramifications for the Complex Physiology of TNF." Cell 53, (1988): 45-53.
Kyte, Jack, and Russell F. Doolittle. "A simple method for displaying the hydropathic character of a protein." Journal of molecular biology 157.1 (1982): 105-132.
Lam, K. S. et al. "A new type of synthetic peptide library for identifying ligand-binding activity." Nature 354, (1991): 82-84.
LaRochelle, Jonathan R., et al. "Fluorescence correlation spectroscopy reveals highly efficient cytosolic delivery of certain penta-arg proteins and stapled peptides." Journal of the American Chemical Society 137.7 (2015): 2536-2541.
Lättig-Tünnemann, Gisela, et al. "Backbone rigidity and static presentation of guanidinium groups increases cellular uptake of arginine-rich cell-penetrating peptides." Nature communications 2 (2011): 453.
Leduc, A. M. et al. "Helix-stabilized cyclic peptides as selective inhibitors of steroid receptor-coactivator interactions." Proc. Natl. Acad. Sci. USA 100, (2003): 11273-11278.
Leung, C. H. et al. "Structure-based repurposing of FDA-approved drugs as TNF-a inhibitors." ChemMedChem 6, (2011): 765-768.
Lewis, Kaitlyn N., et al. "Nrf2, a guardian of healthspan and gatekeeper of species longevity." Integrative and comparative biology 50.5 (2010): 829-843.

(56) References Cited

OTHER PUBLICATIONS

Lian, Wenlong, et al. "Cell-permeable bicyclic peptide inhibitors against intracellular proteins." Journal of the American Chemical Society 136.28 (2014): 9830-9833.
Lian, Wenlong, et al. "Screening bicyclic peptide libraries for protein-protein interaction inhibitors: discovery of a tumor necrosis factor-α antagonist." Journal of the American Chemical Society 135.32 (2013): 11990-11995.
Liu, Jianquan, et al. "Nanostructured materials designed for cell binding and transduction." Biomacromolecules 2.2 (2001): 362-368.
Liu, R., Maril, J. & Lam, K. S. "A novel peptide-based encoding system for "one-bead one-compound" peptidomimetic and small molecule combinatorial libraries." J. Am. Chem. Soc. 124, (2002): 7678-7680.
Liu, T. et al. "Synthesis and screening of a cyclic peptide library: Discovery of small-molecule ligands against human prolactin receptor." Bioorg. Med. Chem. 17, (2009): 1026-1033.
Liu, T., Qian, Z., Xiao, Q. & Pei, D. "High-throughput screening of one-bead-one compound libraries: identification of cyclic peptidyl inhibitors against calcineurin/NF AT interaction." ACS Comb. Sci. 13, (2011): 537-546.
Liu, X., Chen, C. & Hop, C. E. "Do we need to optimize plasma protein and tissue binding in drug discovery?" Curr. Top. Med. Chem. 11, (2011):450-466.
Lo, Shih-Ching, et al. "Structure of the Keap1: Nrf2 interface provides mechanistic insight into Nrf2 signaling." The EMBO journal 25.15 (2006): 3605-3617.
Luzi et al. Subunit disassembly and inhibition of TNFalpha by a semi-synthetic bicyclic peptide, Protein Engineering, Design, & Selection 28(2), (2015): 45-52.
Ma, Bing, et al. "Total synthesis of the antimitotic bicyclic peptide celogentin c." Journal of the American Chemical Society 132.3 (2009): 1159-1171.
Ma, L. et al. "A Novel Small-Molecule Tumor Necrosis Factor α Inhibitor Attenuates Inflammation in a Hepatitis Mouse Model." J. Biol. Chem. 289, (2014): 12457-12466.
Maiolo, et al. "Effects of cargo molecules on the cellular uptake of arginine-rich cell-penetrating peptides." Biochimica et Biophysica Acta (BBA)—Biomembranes 1712.2 (2005): 161-172.
Mancini, F., Toro, C. M., Mabilia, M., Giannangeli, M., Pinza, M. & Milanese, C. Inhibition of tumor necrosis factor-a (TNF-a )—TNF-a receptor binding by structural analogues of suramin. Biochem. Pharmocol. 58, (1999): 851-859.
Mandal, Deendayal, Amir Nasrolahi Shirazi, and Keykavous Parang. "Cell-penetrating homochiral cyclic peptides as nuclear-targeting molecular transporters." Angewandte Chemie International Edition 50.41 (2011): 9633-9637.
Martin, T. L., Mufson, E. J. & Mesulam, M. M. The light side of horseradish peroxidase histochemistry. J. Histochem. Cytochem. 32, (1984):793.
May, Michael J., et al. "Selective inhibition of NF-κB activation by a peptide that blocks the interaction of NEMO with the IκB kinase complex." Science 289.5484 (2000): 1550-1554.
Millward, S.W., et al., "Design of cyclic peptides that bind protein surfaces with antibody-like affinity." ACS Chem. Biol. 2, (2007): 625-634.
Miranda, E. et al. "A Cyclic Peptide Inhibitor of HIF-1 Heterodimerization That Inhibits Hypoxia Signaling in Cancer Cells." J. Am. Chem. Soc. 135, (2013): 10418-10425.
Mitra, Sayantan, and Amy M. Barrios. "Highly sensitive peptide-based probes for protein tyrosine phosphatase activity utilizing a fluorogenic mimic of phosphotyrosine." Bioorganic & medicinal chemistry letters 15.23 (2005): 5142-5145.
Mueller, Judith, et al. "Comparison of cellular uptake using 22 CPPs in 4 different cell lines." Bioconjugate chemistry 19.12 (2008): 2363-2374.
Muratovska, Aleksandra, and Michael R. Eccles. "Conjugate for efficient delivery of short interfering RNA (siRNA) into mammalian cells." FEBS letters 558.1-3 (2004): 63-68.

Nakase, Ikuhiko, et al. "Efficient intracellular delivery of nucleic acid pharmaceuticals using cell-penetrating peptides." Accounts of chemical research 45.7 (2011): 1132-1139.
Nakase, Ikuhiko, et al. "Interaction of arginine-rich peptides with membrane-associated proteoglycans is crucial for induction of actin organization and macropinocytosis." Biochemistry 46.2 (2007): 492-501.
Ndikuyeze, Georges Habineza, et al. "A phase I clinical trial of systemically delivered NEMO binding domain peptide in dogs with spontaneous activated B-cell like diffuse large B-cell lymphoma." PloS one 9.5 (2014): e95404.
Nevola, Laura, and Ernest Giralt. "Modulating protein-protein interactions: the potential of peptides." Chemical Communications 51.16 (2015): 3302-3315.
Nguyen, Leonard T., et al. "Serum stabilities of short tryptophan- and arginine-rich antimicrobial peptide analogs." PloS one 5.9 (2010): e12684.
Nori, Aparna, et al. "Tat-conjugated synthetic macromolecules facilitate cytoplasmic drug delivery to human ovarian carcinoma cells." Bioconjugate chemistry 14.1 (2003): 44-50.
Oeckinghaus, Andrea, and Sankar Ghosh. "The NF-κB family of transcription factors and its regulation." Cold Spring Harbor perspectives in biology 1.4 (2009): a000034.
Palm-Apergi, Caroline, et al. "The membrane repair response masks membrane disturbances caused by cell-penetrating peptide uptake." The FASEB Journal 23.1 (2009): 214-223.
Pelay-Gimeno, Marta, et al. "Structure-based design of inhibitors of protein-protein interactions: mimicking peptide binding epitopes." Angewandte Chemie International Edition 54.31 (2015): 8896-8927.
Pelay-Gimeno, Marta, et al. "Strukturbasierte Entwicklung von Protein-Protein-Interaktionsinhibitoren: Stabilisierung und Nachahmung von Peptidliganden." Angewandte Chemie 127.31 (2015): 9022-9054.
Pennica, D. et al. "Human Tumour Necrosis Factor: Precursor Structure, Expression and Homology to Lymphotoxin." Nature 312, (1984):724-729.
Peterson, Jennifer M., et al. "Peptide-based inhibition of NF-κB rescues diaphragm muscle contractile dysfunction in a murine model of Duchenne muscular dystrophy." Molecular medicine 17.5-6 (2011): 508-515.
Pham, Wellington, et al. "Enhancing membrane permeability by fatty acylation of oligoarginine peptides." Chembiochem 5.8 (2004): 1148-1151.
Pooga, Margus, et al. "Cellular translocation of proteins by transportan." The FASEB Journal 15.8 (2001): 1451-1453.
Qian, Ziqing, et al. "Discovery and mechanism of highly efficient cyclic cell-penetrating peptides." Biochemistry 55.18 (2016): 2601-2612.
Qian, Ziqing, et al. "Early endosomal escape of a cyclic cell-penetrating peptide allows effective cytosolic cargo delivery." Biochemistry 53.24 (2014): 4034-4046.
Qian, Ziqing, et al. "Efficient delivery of cyclic peptides into mammalian cells with short sequence motifs." ACS chemical biology 8.2 (2012): 423-431.
Qian, Ziqing, et al. "Intracellular delivery of peptidyl ligands by reversible cyclization: discovery of a PDZ domain inhibitor that rescues CFTR activity." Angewandte Chemie International Edition 54.20 (2015): 5874-5878. Angew. Chem. 2015, 127, 5972.
Qian, Ziqing, et al. "Monitoring the cytosolic entry of cell-penetrating peptides using a pH-sensitive fluorophore." Chemical Communications 51.11 (2015): 2162-2165.
Rajendran, Peramaiyan, et al. "Antioxidants and human diseases." Clinica chimica acta 436 (2014): 332-347.
Reay, Daniel P., et al. "Systemic delivery of NEMO binding domain/IKKγ inhibitory peptide to young mdx mice improves dystrophic skeletal muscle histopathology." Neurobiology of disease 43.3 (2011): 598-608.
Rezai, Taha, et al. "Conformational flexibility, internal hydrogen bonding, and passive membrane permeability: successful in silico prediction of the relative permeabilities of cyclic peptides." Journal of the American Chemical Society 128.43 (2006): 14073-14080.

(56) References Cited

OTHER PUBLICATIONS

Richard, Jean Philippe, et al. "Cellular uptake of unconjugated TAT peptide involves clathrin-dependent endocytosis and heparan sulfate receptors." Journal of Biological Chemistry 280.15 (2005): 15300-15306.

Robinson, John A. "β-Hairpin peptidomimetics: design, structures and biological activities." Accounts of chemical research 41.10 (2008): 1278-1288.

Rothbard, Jonathan B., et al. "Conjugation of arginine oligomers to cyclosporin A facilitates topical delivery and inhibition of inflammation." Nature medicine 6.11 (2000): 1253.

Rothwarf, David M., et al. "IKK-γ is an essential regulatory subunit of the IκB kinase complex." Nature 395.6699 (1998): 297.

Rueping, Magnus, et al. "Cellular uptake studies with β-peptides." ChemBioChem 3.2-3 (2002): 257-259.

Rushe, Mia, et al. "Structure of a NEMO/IKK-associating domain reveals architecture of the interaction site." Structure 16.5 (2008): 798-808.

Rutledge, S.E., Volkman, H.M. & Schepartz, A."Molecular recognition of protein surfaces: high affinity ligands for the CBPKIX domain." J. Am. Chem. Soc. 125, (2003): 14336-14347.

Saar, Külliki, et al. "Cell-penetrating peptides: a comparative membrane toxicity study." Analytical biochemistry 345.1 (2005): 55-65.

Saito, H. et al. "A tumor necrosis factor receptor loop peptide mimic inhibits bone destruction to the same extent as anti-tumor necrosis factor monoclonal antibody in murine collagen-induced arthritis." Arthritis Rheum. 56, (2007):1164-1174.

Sako, Y., Morimoto, J., Murakami, H. & Suga, H. "Ribosomal synthesis of bicyclic peptides via two orthogonal inter-side-chain reactions." J. Am. Chem. Soc. 130, (2008): 7232-7234.

Sandberg, Mats, et al. "NRF2-regulation in brain health and disease: implication of cerebral inflammation." Neuropharmacology 79 (2014): 298-306.

Schmidt, Nathan, et al. "Arginine-rich cell-penetrating peptides." FEBS letters 584.9 (2010): 1806-1813.

Scholl, Markus, Zuzana Kadlecova, and Harm-Anton Klok. "Dendritic and hygerbranched polyamides." Progress in Polymer Science 34.1 (2009): 24-61.

Schwarze, Steven R., et al. "In vivo protein transduction: delivery of a biologically active protein into the mouse." Science 285.5433 (1999): 1569-1572.

Shen, Q. et al., "De novo design of helical peptides to inhibit tumor necrosis factor-α by disrupting its trimer formation." Med. Chem. Commun. 7, (2016): 725-729.

Shibata, Wataru, et al. "Cutting edge: the IκB kinase (IKK) inhibitor, NEMO-binding domain peptide, blocks inflammatory injury in murine colitis." The Journal of Immunology 179.5 (2007): 2681-2685.

Shrake, A., and J. A. Rupley. "Environment and exposure to solvent of protein atoms. Lysozyme and insulin." Journal of molecular biology 79.2 (1973): 351-371.

Skelton, Nicholas J., et al. "β-hairpin polypeptides by design and selection." Journal of Spectroscopy 17.2-3 (2003): 213-230.

Stanford, Stephanie M., et al. "High-throughput screen using a single-cell tyrosine phosphatase assay reveals biologically active inhibitors of tyrosine phosphatase CD45." Proceedings of the National Academy of Sciences 109.35 (2012): 13972-13977.

Steiner, D., Forrer, P. & Plueckthun, A. "Efficient selection of DARPins with subnanomolar affinities using SRP phage display." J. Mol. Biol. 382, (2008):1211-1227.

Stewart, Kelly M., Kristin L. Horton, and Shana O. Kelley. "Cell-penetrating peptides as delivery vehicles for biology and medicine." Organic & biomolecular chemistry 6.13 (2008): 2242-2255.

Suhorutsenko, Julia, et al. "Cell-penetrating peptides, PepFects, show no evidence of toxicity and immunogenicity in vitro and in vivo." Bioconjugate chemistry 22.11 (2011): 2255-2262.

Sun, Shao-Cong, Jae-Hoon Chang, and Jin Jin. "Regulation of nuclear factor-κB in autoimmunity." Trends in immunology 34.6 (2013): 282-289.

Sun, Y., Lu, G. & Tam, J. P. "A thioester ligation approach to amphipathic bicyclic peptide library." Org. Lett. 3, (2001): 1681-1684.

Sweeney, M. C et al. "Decoding protein-protein interactions through combinatorial chemistry: sequence specificity of SHP-1, SHP-2, and SHIP SH2 domains." Biochemistry 44, (2005): 14932-14947.

Taguchi, Keiko, Hozumi Motohashi, and Masayuki Yamamoto. "Molecular mechanisms of the Keap1-Nrf2 pathway in stress response and cancer evolution." Genes to cells 16.2 (2011): 123-140.

Takada, Y. et al. "Evodiamine Abolishes Constitutive and Inducible NF-κB Activation by Inhibiting IκBα Kinase Activation, Thereby Suppressing NF-κB-regulated Antiapoptotic and Metastatic Gene Expression, Up-regulating Apoptosis, and Inhibiting Invasion." J. Biol. Chem. 280, (2005): 17203-17212.

Takasaki,W .,et al., "Structure-based design and characterization of exocyclic peptidomimetics that inhibit TNF alpha binding to its receptor." Nat. Biotechnol. 15, (1997): 1266-1270.

Tang, P. et al. "Human pro-Tumor Necrosis Factor Is a Homotrimer." Biochemistry (Mosc.) 35, (1995): 8216-8225.

Tavassoli, A., et al., "Inhibition of HN budding by a genetically selected cyclic peptide targeting the Gag-TSG 101 interaction." ACS Chem. Biol. 3, (2008): 757-764.

Thakkar, A., Thi, T. B. & Pei, D. "Global analysis of peptide cyclization efficiency." ACS Comb. Sci. 15, (2013): 120-129.

Thakkar, A., Wavreille, A-S. & Pei, D. "Traceless capping agent for peptide sequencing by partial Edman degradation and mass spectrometry." Anal. Chem. 78, (2006): 5935-5939.

Tien, Matthew Z., et al. "Maximum allowed solvent accessibilites of residues in proteins." PloS one 8.11 (2013): e80635.

Timmerman, P. et al. "A combinatorial approach for the design of complementarity determining region-derived peptidomimetics with in vitro anti-tumoral activity." J. Biol. Chem. 284, (2009): 34126-34134.

Tong, Kit I., et al. "Different electrostatic potentials define ETGE and DLG motifs as hinge and latch in oxidative stress response." Molecular and cellular biology 27.21 (2007): 7511-7521.

Tong, Kit I., et al. "Keap1 recruits Neh2 through binding to ETGE and DLG motifs: characterization of the two-site molecular recognition model." Molecular and cellular biology 26.8 (2006): 2887-2900.

Trinh, Thi B., et al. "Discovery of a direct Ras inhibitor by screening a combinatorial library of cell-permeable bicyclic peptides." ACS combinatorial science 18.1 (2015): 75-85.

Upadhyaya, et al. "Direct Ras inhibitors identified from a structurally ridigified bicyclic peptide library." Tetrahedron, 2014, 70(42), 7714-7720.

Upadhyaya, Punit, et al. "Inhibition of Ras signaling by blocking Ras-effector interactions with cyclic peptides." Angewandte Chemie International Edition 54.26 (2015): 7602-7606. Angew. Chem. 127, (2015): 7712.

Varkouhi, Amir K., et al. "Endosomal escape pathways for delivery of biologicals." Journal of Controlled Release 151.3 (2011): 220-228.

Virta, P. & Lonnberg, H. J. "Solid-supported synthesis of cryptand-like macrobicyclic peptides." J. Org. Chem. 68, (2003): 8534.

Vriens, Kim, Bruno Cammue, and Karin Thevissen. "Antifungal plant defensins: mechanisms of action and production." Molecules 19.8 (2014): 12280-12303.

Wadia, Jehangir S., and Steven F. Dowdy. "Transmembrane delivery of protein and peptide drugs by TAT-mediated transduction in the treatment of cancer." Advanced drug delivery reviews 57.4 (2005): 579-596.

Wajant, H. et al. "Tumor Necrosis Factor Signaling." Cell Death Differ 10, (2003): 45-65.

Wells, James A., and Christopher L. McClendon. "Reaching for high-hanging fruit in drug discovery at protein-protein interfaces." Nature 450.7172 (2007): 1001.

White, Tina R., et al. "On-resin N-methylation of cyclic peptides for discovery of orally bioavailable scaffolds." Nature chemical biology 7.11 (2011): 810.

(56) References Cited

OTHER PUBLICATIONS

Wolde, Michael, et al. "Targeting CAL as a negative regulator of ΔF508-CFTR cell-surface expression an rna interference and structure-based mutagenetic approaCH." Journal of Biological Chemistry 282.11 (2007): 8099-8109.

Wu, X., et al., "Inhibition of Ras-effector interactions by cyclic peptides." Med. Chem. Commun. 4, (2013): 378-382.

Xu, L.H. et al. "Directed evolution of high-affinity antibody mimics using mRNA display." Chem. Biol. 9, (2002):933-942.

Yamagishi, Y. et al. "Natural product-like macrocyclic N-methyl-peptide inhibitors against a ubiquitin ligase uncovered from a ribosome-expressed de novo library." Chem. Biol. 18, (2011):1562-1570.

Yamaoka, Shoji, et al. "Complementation cloning of NEMO, a component of the IκB kinase complex essential for NF-κB activation." Cell 93.7 (1998): 1231-1240.

Yin, J. et al. "Genetically encoded short peptide tag for versatile protein labeling by Sfp phosphopantetheinyl transferase." Proc. Natl. Acad. Sci. USA 102 (2005): 15815-15820.

Zhang, Donna D., et al. "Distinct cysteine residues in Keap1 are required for Keap1-dependent ubiquitination of Nrf2 and for stabilization of Nrf2 by chemopreventive agents and oxidative stress." Molecular and cellular biology 23.22 (2003): 8137-8151.

Zhang, Meijuan, et al. "Emerging roles of Nrf2 and phase II antioxidant enzymes in neuroprotection." Progress in neurobiology 100 (2013): 30-47.

Zhao, Bingchuan, et al. "A Thioether-Stabilized d-Proline-1-Proline-Induced β-Hairpin Peptide of Defensin Segment Increases Its Anti-Candida albicans Ability." ChemBioChem 17.15 (2016): 1416-1420.

Zhao, Kun, et al. "Enhanced activity of cyclic transporter sequences driven by phase behavior of peptide-lipid complexes." Soft Matter 8.24 (2012): 6430-6433.

Zhou, H. et al. "Structure-based design of high-affinity macrocyclic peptidomimetics to block the menin-mixed lineage leukemia 1 (MLL1) protein-protein interaction." J. Med. Chem. (2013) 56, 1113-1123.

International Search Report and Written Opinion issued for Application No. PCT/US2017/062951, dated Apr. 30, 2018.

International Preliminary Report on Patentability issued for Application No. PCT/US2017/062951 dated Jun. 6, 2019.

International Preliminary Report on Patentability issued for Application No. PCT/US17/60881, dated May 23, 2019.

International Preliminary Report on Patentability issued for Application No. PCT/US2017/063020 dated Jun. 6, 2019.

International Search Report and Written Opinion issued for Application No. PCT/US2017/063020 dated May 4, 2018.

International Search Report and Written Opinion issued for Application No. PCT/US2019/031522, dated Sep. 27, 2019.

International Search Report and Written Opinion issued for Application No. PCT/US2014/039332, dated Dec. 3, 2014.

International Search Report and Written Opinion issued for Application No. PCT/US2017/062945, dated Feb. 16, 2018.

International Preliminary Report on Patentability issued for Application No. PCT/US2017/062945, dated Jun. 6, 2019.

D'Souza et al., Structural parameters modulating the cellular uptake of disulfide-rich cyclic cell-penetrating peptides: MCoTI-II and SFTI-1, European Journal of Medicinal Chemistry, vol. 88, 99 10-18, 2014.

Extended European Search Report issued in EP 17870556.2, dated Sep. 8, 2020.

Notice of Allowance issued in U.S. Appl. No. 16/462,914, dated Sep. 29, 2020.

Lai et al. Design of Non-Cysteine-Containing Antimicrobial a-Hairpins: Structure-Activity Relationship Studies with Linear Protegrin-1 Analogues. Biochemistry 2002, 41, 12835-12842.

Langham et al. Comparison of interactions between beta-hairpin decapeptides and SDS/DPC micelles from experimental and simulation data. BMC Biochemistry, 2007. vol. 8. No. 11, pp. 1-13.

International Preliminary Report on Patentability issued in PCT/US2019/031522, dated Nov. 19, 2020.

International Search Report and Written Opinion. Issued by the International Searching Authority (US) in PCT Application No. PCT/US2017/060881 dated Apr. 26, 2018. 15 pages.

Chen, Shiyu, et al. "Bicyclic peptide ligands pulled out of cysteine-rich peptide libraries." Journal of the American Chemical Society 135.17 (2013): 6562-6569.

Orange, J. S., and M. J. May. "Cell penetrating peptide inhibitors of nuclear factor-kappa B." Cellular and Molecular Life Sciences 65.22 (2008): 3564-3591.

Qian, Ziqing, et al. "Enhancing the cell permeability and metabolic stability of peptidyl drugs by reversible bicyclization." Angewandte Chemie International Edition 56.6 (2017): 1525-1529.

Office Action in connection to TW Applicaton No. 106138809, dated Nov. 5, 2021.

Chen et al. Nature Chemistry. "Dithiol Amono acids can structurally shape and enhance the ligand-binding properties of polypeptides" dated Aug. 31, 2014, 8 pages.

Office Acttion in connection with JP Applicatin No. 2019-524067, dated Oct. 5, 2021.

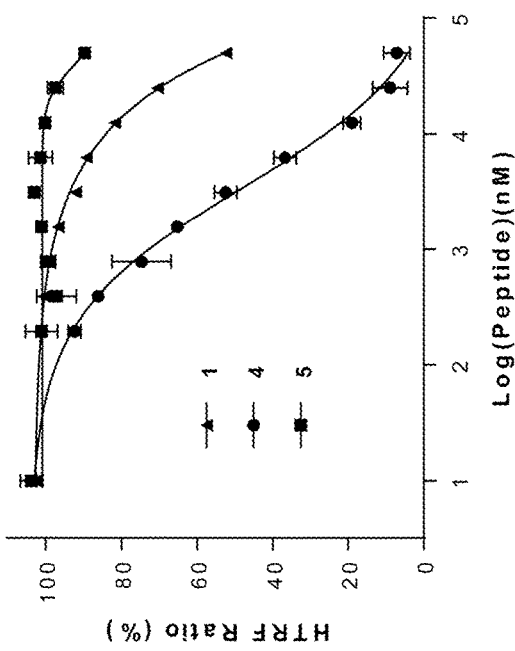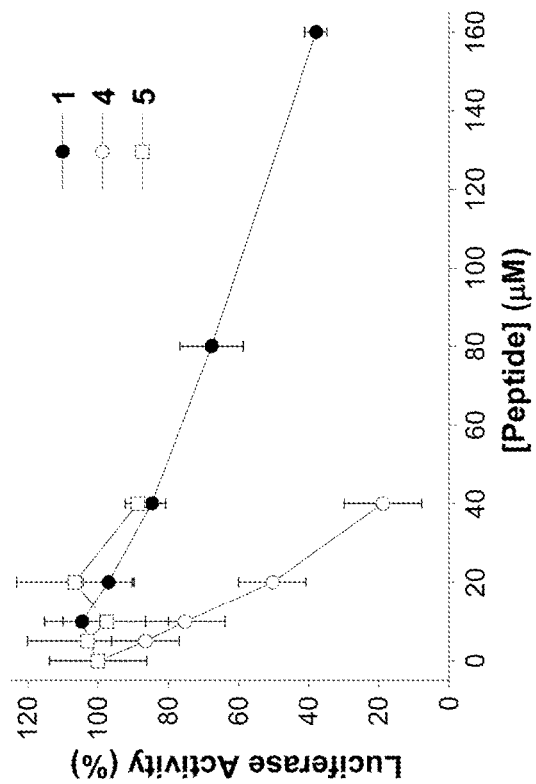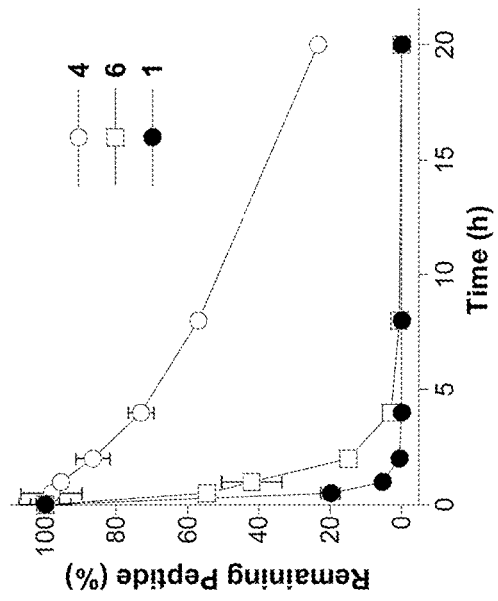

Peptide 3

Peptide 6

DI-SULFIDE CONTAINING CELL PENETRATING PEPTIDES AND METHODS OF MAKING AND USING THEREOF

CROSS-REFERENCE TO RELATED APPLICATIONS

This application is a national stage application filed under 35 U.S.C. § 371 of PCT/US2017/060881 filed Nov. 9, 2017, which claims priority to U.S. App. No. 62/419,781, filed on Nov. 9, 2016, U.S. App. No. 62/425,550, filed Nov. 22, 2016, and U.S. App. No. 62/438,141, filed Dec. 22, 2016, each of which are herein incorporated by reference in its entirety.

STATEMENT REGARDING FEDERALLY FUNDED RESEARCH

This invention was made with government support under grant numbers GM062820, GM110208, and GM122459 awarded by the National Institutes of Health. The government has certain rights in the invention.

BACKGROUND

Compared to small-molecule drugs, peptides are highly selective and efficacious and, at the same time, relatively safe and well tolerated. A particularly exciting application of peptides is the inhibition of protein-protein interactions (PPIs), which remain challenging targets for small molecules. Consequently, there is an increased interest in peptides in pharmaceutical research and development, and ~140 peptide therapeutics are currently being evaluated in clinical trials. However, peptides are inherently susceptible to proteolytic degradation. Additionally, peptides are generally impermeable to the cell membrane, largely limiting their applications to extracellular targets. Although N-methylation of the peptide backbone and formation of intramolecular hydrogen bonds have been shown to improve the proteolytic stability and membrane permeability of certain cyclic peptides (T. Rezai, et al., *J. Am. Chem. Soc.* 2006, 128, 14073), alternative strategies to increase both the metabolic stability and cell permeability of peptide drugs are clearly needed.

NF-κB is a transcription factor that controls the expression of numerous gene products involved in immune, stress, inflammatory responses, cell proliferation, and apoptosis (A. Oeckinghaus, S. Ghosh, *Cold Spring Harb. Perspect. Biol.* 2009, 1, a000034). Aberrant activation of NF-κB signaling has been implicated in a number of autoimmune diseases (e.g., rheumatoid arthritis) and cancer (e.g., diffuse large B-cell lymphoma), among others (V. Baud, M. Karin, *Nat. Rev. Drug Discov.* 2009, 8, 33; S.-C. Sun, et al., *Trends Immunol.* 2013, 34, 282; F. D. Herrington, et al., *J. Biomol. Screen.* 2016, 21, 223; G. Cildir, et al., *Trends Mol. Med.* 2016, 22, 414). Canonical NF-κB signaling is mediated by the interaction between the inhibitor of κB (IκB)-kinase (IKK) complex and regulatory protein NF-κB essential modifier (NEMO) (S. Yamaoka, et al., *Cell* 1998, 26, 1231; D. M. Rothwarf, et al., *Nature* 1998, 395, 297). Binding to NEMO activates IKK, which in turn phosphorylates IκB, promoting the proteasomal degradation of IκB and release of active NF-κB. Modulators targeting various steps of the NF-κB signaling pathway have been reported, and some of them have progressed into the clinic (V. Baud, M. Karin, *Nat. Rev. Drug Discov.* 2009, 8, 33; S.-C. Sun, et al., *Trends Immunol.* 2013, 34, 282; F. D. Herrington, et al., *J. Biomol. Screen.* 2016, 21, 223; G. Cildir, et al., *Trends Mol. Med.* 2016, 22, 414; S. C. Gupta, et al., *Biochim. Biophys. Acta.* 2011, 1799, 775; T. M. Herndon, et al., *Clin. Cancer Res.* 2013, 19, 4559). One attractive strategy for ameliorating the NF-κB activity is to selectively disrupt the IKK-NEMO interaction. Previous studies generated a weak NEMO inhibitor ($K_D$~37 μM), Antp-NBD (Table 6, peptide 1), which contains the 11-residue NEMO-binding domain (NBD) of IKKβ covalently linked to a cell-penetrating peptide (CPP), Antp (M. J. May, et al., *Science* 2000, 289, 1550). Interestingly, Antp-NBD blocks the IKK activity stimulated by different pro-inflammatory stimuli, but does not affect the basal NF-κB activity, thus providing a potentially safe and effective mechanism for reducing aberrant NF-κB activity (J. May, et al., *Science* 2000, 289, 1550). In several pre-clinical studies, Antp-NBD demonstrated in vivo efficacy for treating Duchenne muscular dystrophy and large B-cell lymphoma in mouse and canine models (E. Jimi, et al., *Nat. Med.* 2004, 10, 617; S. Dai, et al., *J. Biol. Chem.* 2004, 279, 37219; W. Shibata, et al., *J. Immunol.* 2007, 179, 2681; S. H. Dave, et al., *J. Immunol.* 2007, 179, 7852; A. Gaurnier-Hausser, et al., *Clin. Cancer Res.* 2011, 17, 4661; J. M. Peterson, et al., *Mol. Med.* 2011, 17, 508; D. A. Delfin, et al., *J. Transl. Med.* 2011, 9, 68; D. P. Reay, et al., *Neurobiol. Dis.* 2011, 43, 598; J. N. Kornegay, et al., *Skelet. Muscle* 2014, 4, 18; G. Habineza Ndikuyeze, et al., *PLoS One*, 2014, 9, e95404). However, to achieve clinical utility, Antp-NBD would benefit significantly from improvements in its NEMO-binding affinity, metabolic stability, and cell-permeability. What are thus needed are new compositions and methods for modulating NF-κB signaling. The compositions and methods disclosed herein address these and other needs.

SUMMARY

Disclosed herein are compounds, compositions, methods for making and using such compounds and compositions. In various embodiments disclosed herein are bicyclic peptides, compositions comprising such bicyclic peptides, and methods of making and using them.

In some embodiments, the bicyclic peptides disclosed herein comprise: (a) a first cyclic peptide comprising a cell-penetrating peptide sequence ($X_m$); (b) a second cyclic peptide comprising a peptidyl ligand ($X_n$); and (c) at least one disulfide bond which forms at least one of the first cyclic peptide or the second cyclic peptide, wherein the first cyclic peptide is conjugated to the second cyclic peptide.

In various embodiments, $X_m$ comprises the following peptide sequence:

$AA^1$-$AA^2$-$AA^3$-$AA^4$-$AA^5$-$(AA^6)_m$-$(AA^7)_n$-$(AA^8)_p$-$(AA^9)_q$- wherein:

$AA^1$, $AA^2$, $AA^3$, $AA^4$, $AA^5$, $AA^6$, $AA^7$, $AA^8$, and $AA^9$, are each independently an amino acid, which is optionally substituted, and where at least three amino acids are arginine and at least two amino acids independently comprise a hydrophobic side chain; and m, n, p, and q are independently selected from 0 and 1.

In some embodiments, the bicyclic peptides comprise a linking moiety which is conjugated, directly or indirectly, to $X_m$ and $X_n$. In some embodiments, $X_m$ is cyclized through the linking moiety, the C- or N-terminus of $X_n$ is conjugated to the linking moiety, and $X_n$ is cyclized through the disulfide bond, thereby forming the bicyclic peptide. In other embodiments, the linking moiety is conjugated to the side chain of an amino acid in the first cyclic peptide, the C- or N-terminus of $X_n$ is conjugated to the linking moiety, and wherein $X_n$ is cyclized through the disulfide bond, thereby forming the bicyclic peptide.

In some embodiments, the bicyclic peptides disclosed herein comprise a first disulfide bond and a second disulfide bond. In other embodiments, linking moiety comprises a first substituent which forms the first disulfide bond and a second substituent which forms the second disulfide bond. In some embodiments, $X_m$ is cyclized through the first disulfide bond, and $X_n$ is cyclized through the second disulfide bond, thereby forming the bicyclic peptide. In still other embodiments, the linking moiety is conjugated to the side chain of the first cyclic peptide, and $X_n$ is cyclized through the first disulfide bond and the second disulfide bond, thereby forming the bicyclic peptide. In yet still other embodiments, the C- or N-terminus of $X_m$ is conjugated to the linking moiety and $X_m$ is cyclized through the first disulfide bond, and wherein the C- or N-terminus of $X_n$ is conjugated to the linking moiety and $X_n$ is cyclized through the second disulfide bond, thereby forming the bicyclic peptide. In still even more embodiments, the C- or N-terminus of $X_n$ is conjugated to the linking moiety, and wherein $X_m$ is cyclized through the first disulfide bond and $X_n$ is cyclized through the second disulfide bond, thereby forming the bicyclic peptide.

In some embodiments, the bicyclic peptides disclosed herein comprise a third disulfide bond. In other embodiments, the linker moiety comprises a first substituent which forms the first disulfide bond, a second substituent which forms the second disulfide bond, and third substituent which forms the third disulfide bond. In still other embodiments, $X_m$ is fused to $X_n$, thereby forming a fused $X_m$-$X_n$ peptide, and the linking moiety is conjugated to the fused $X_m$-$X_n$, peptide through the third disulfide bond, and wherein $X_m$ is cyclized through the first disulfide bond and $X_n$ is cyclized through the second disulfide bond, thereby forming the bicyclic peptide.

In some embodiments, the bicyclic peptides disclosed herein comprise a fourth disulfide bond. In some embodiments, the linker moiety comprises a first substituent which forms the first disulfide bond, a second substituent which forms the second disulfide bond, third substituent which forms the third disulfide bond comprises, and a fourth substituent which forms a forth disulfide bond. In other embodiments, $X_m$ is cyclized through the first disulfide bond and the second disulfide bond, and $X_n$ is cyclized through the third disulfide bond and the fourth disulfide bond, thereby forming the bicyclic peptide.

In various embodiments, the bicyclic peptides disclosed herein have a structure according to any of Formulae 1-12

| Number | Formula |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) | wherein:
  $AA^S$ at each occurrence is independently a moiety which forms a disulfide bond with J;
  L-J is the linking moeity, wherein:
    J is absent, or an alkyl, N-alkyl, alkenyl, alkynyl, carbocyclyl, or heterocyclyl, each of which are independently substituted with at least two substituents which independently form a disulfide bond with $AA^S$ at each occurrence; and
    L is absent or a moiety which links $AA^S$ to an amino acid in $X_m$, $X_n$ or a combination thereof; and
  SS at each instance represents a disulfide bond.

In some embodiments, the bicyclic peptides described above have a structure according to any of Formula I, II, V, VI, VII, VIII, IX, X, and XII, each of which are described in more detail below.

In embodiments, disclosed herein are bicyclic peptides comprising Formula I or II

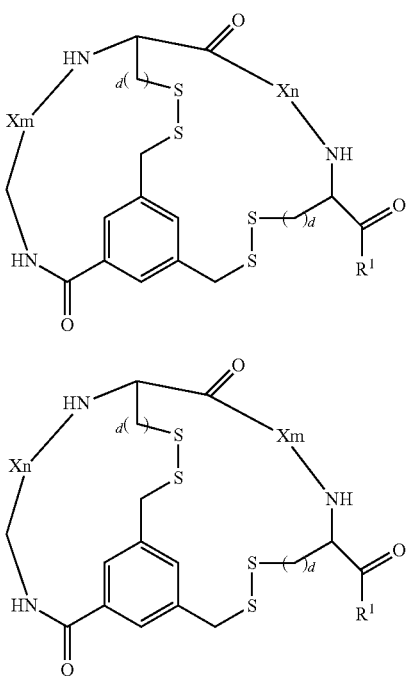

wherein $X_m$ and $X_n$ independently comprise a sequence of 1-20 amino acids and $R^1$ is OH, $OR^2$, or $NHR^2$, wherein $R^2$ is a $C_{1-20}$ alkyl, $C_{6-10}$ aryl or heteroaryl, amino acid, peptide sequence of 2 to 20 amino acids, detectable moiety, or solid support.

As used herein, $X_m$ refers to a cell penetrating peptide sequence. In some embodiments, $X_m$ is from 5 to 10 amino acids in length. In further embodiments, at least one, at least two, or at least three amino acids in $X_m$ have a hydrophobic side chain. In certain embodiments, $X_m$ comprises one or more phenylalanine, naphthylalanine, tryptophan, or an analog or derivative thereof. In some embodiments, $X_m$ comprises at least one arginine or an analog or derivative thereof. In other embodiments, $X_m$ comprises a sequence listed in Table 2 (SEQ ID NO:62 through SEQ ID NO:146). In certain embodiments, $X_m$ is or comprises RRRRΦF or RΦRRRR.

As used herein, $X_n$ refers to a cargo sequence. In some embodiments, $X_n$ comprises a sequence listed in Table 5 (SEQ ID NO:147 through SEQ ID NO:159). In some embodiments, the bicyclic peptide has a sequence listed in Table 6 (SEQ ID NO:160 through SEQ ID NO:167).

In additional examples disclosed herein are peptides of Formula III $$BMB\text{-}(AA^n)_u \qquad \qquad III$$

wherein n is an integer of from 5 to 20, and each $AA^n$ is, independently, a natural or non-natural amino acid residue, with at least two $AA^1$ residues being cysteine, and BMB is a 3,5-bis(mercaptomethyl)benzoic acid residue. In some specific examples u is 4 to 20, 5 to 9, 6 to 9, 7 to 8, or 8 to 9.

Also disclosed herein, in various embodiments, are methods of making a bicyclic peptide, comprising:
(a) contacting a solid supported peptide having from 8 to 40 amino acid, wherein at least two amino acids are independently selected from the group consisting of a cysteine, homocysteine, an amino acid analog having a thiol group, with a compound of Formula IV:

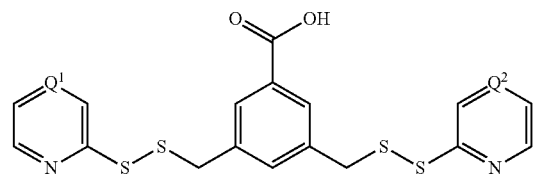

wherein $Q^1$ and $Q^2$ are, independent of one another, chosen from CH or N; and (b) cleaving the peptide from the solid support.

Other embodiments of the present disclosure provide a bicyclic peptide comprising Formula V, VI, VII, VIII, IX, X, or XII:

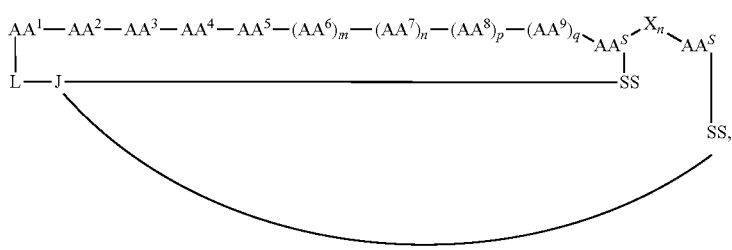

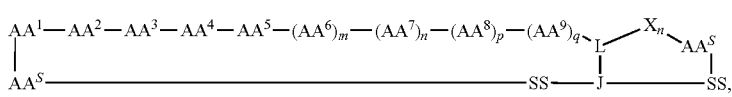

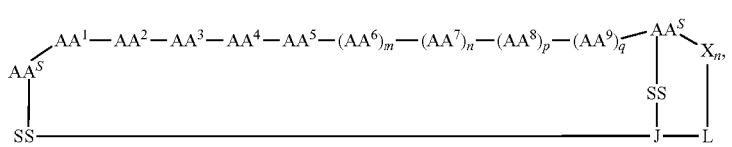

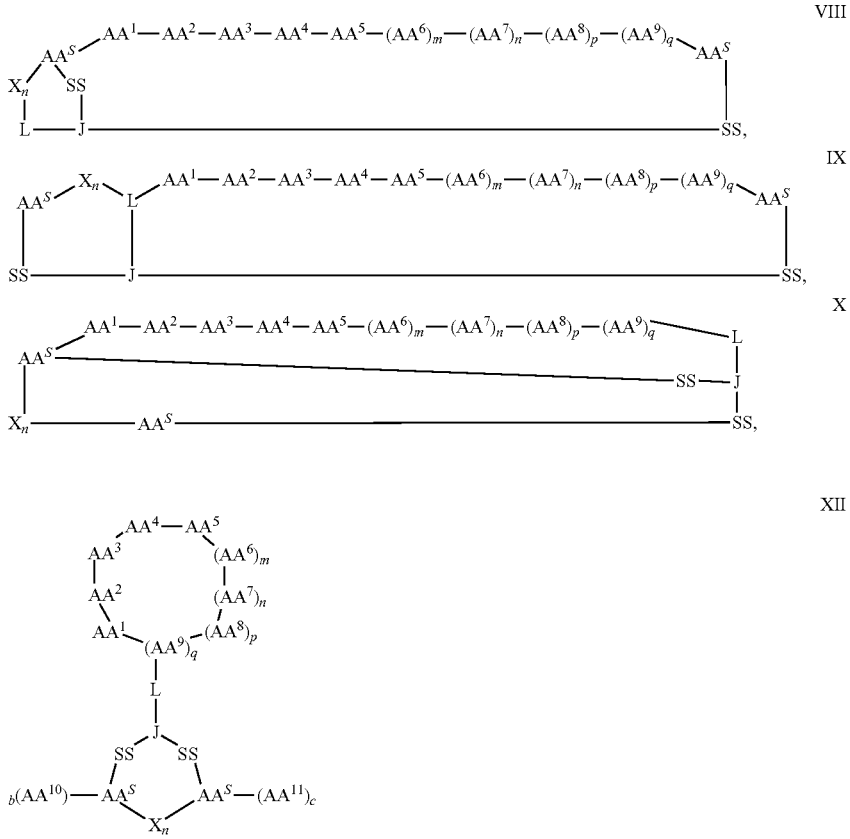

or a pharmaceutically acceptable salt thereof, wherein:

$AA^1$, $AA^2$, $AA^3$, $AA^4$, $AA^5$, $AA^6$, $AA^7$, $AA^8$, and $AA^9$ are each independently an amino acid, which is optionally substituted, where at least three amino acids are arginine and at least two amino acids independently comprise a hydrophobic side chain;

m, n, p, and q are independently selected from 0 and 1;

$AA^{10}$ and $AA^{11}$, are each independently an amino acid, which is optionally substituted;

b and c are independently an integer from 0 to 20;

$AA^S$ at each occurrence is independently a moiety which forms a disulfide bond with J;

J is an alkyl, N-alkyl, alkenyl, alkynyl, carbocyclyl, or heterocyclyl, each of which are independently substituted with at least two substituents which independently form a disulfide bond with $AA^S$ at each occurrence;

ss at each instance represents a disulfide bond; and

L is a moiety which links J to an amino acid, $X_n$, or a combination thereof; and $X_n$ is a cargo moiety comprising a peptide sequence having from 1 to 20 amino acids.

In some embodiments, J is N-alkyl, aryl, or heteroaryl, each of which are independently substituted with at least two substituents which independently form a disulfide bond with $AA^S$ at each occurrence. In other embodiments, J is

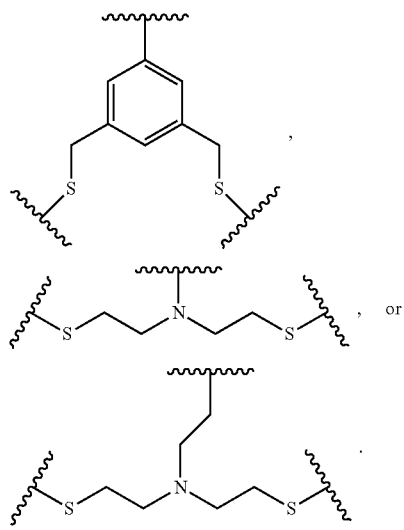

In some embodiments, L is a bond, an amino acid,

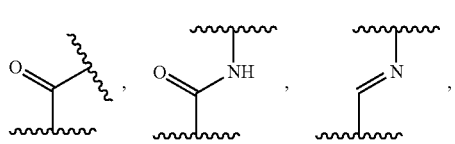

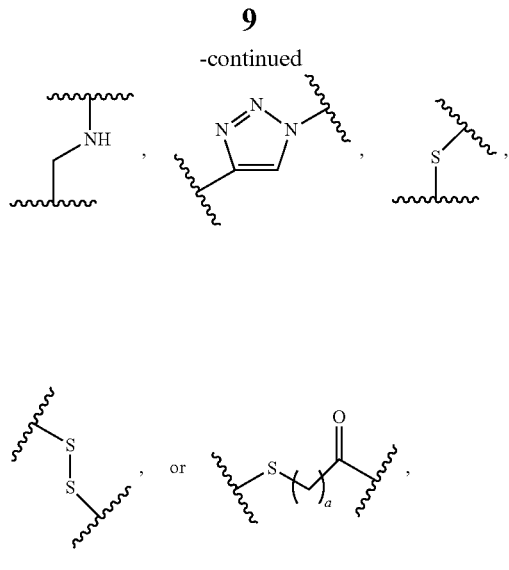

wherein a is an integer from 0 to 10.

In some embodiments, each $AA^S$ independently is

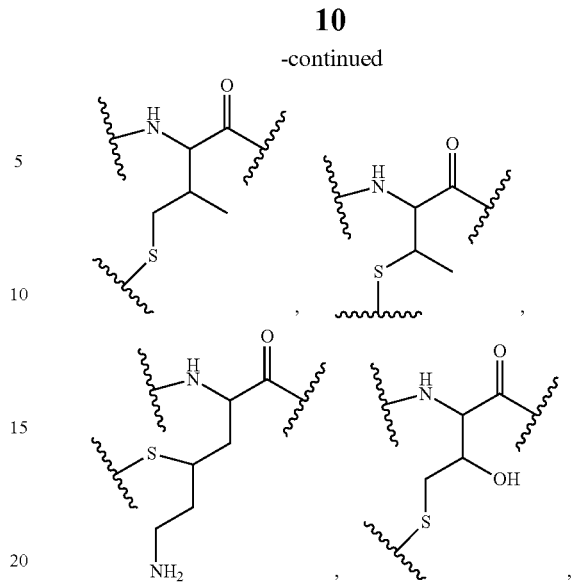

wherein the C-terminus of $AA^S$ forms an amide bond or is $R^1$, wherein $R^1$ is OH, $OR^2$, $NHR^2$; and wherein $R^2$ is an alkyl, aryl, heteroaryl, amino acid, peptide sequence of 2 to 20 amino acids, detectable moiety, or solid support.

In some embodiments, the bicyclic peptides disclosed herein are selected from the group consisting of:

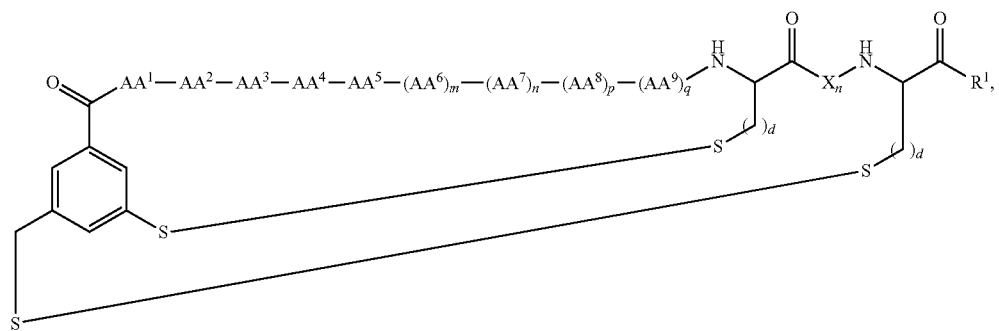

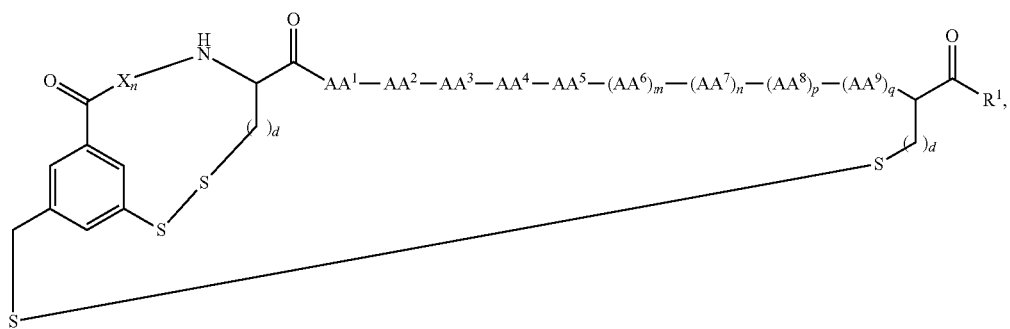
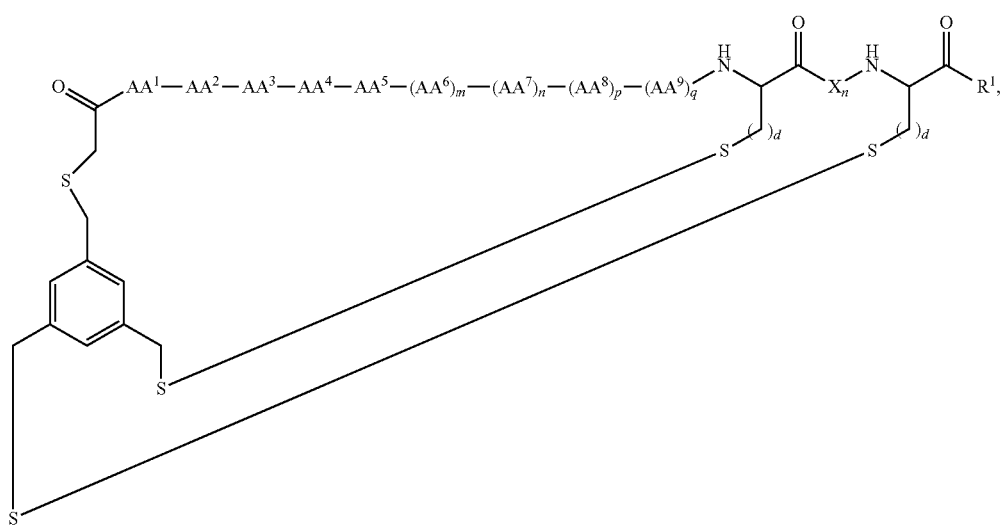
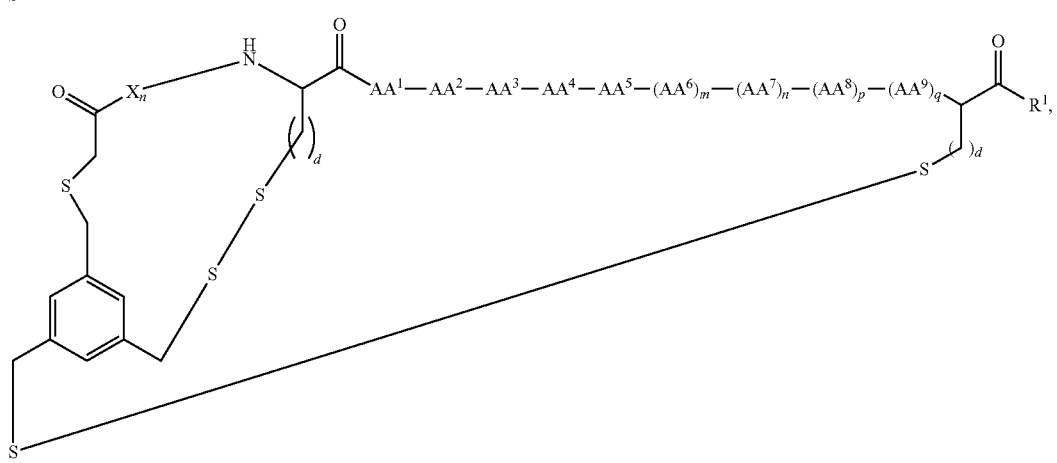
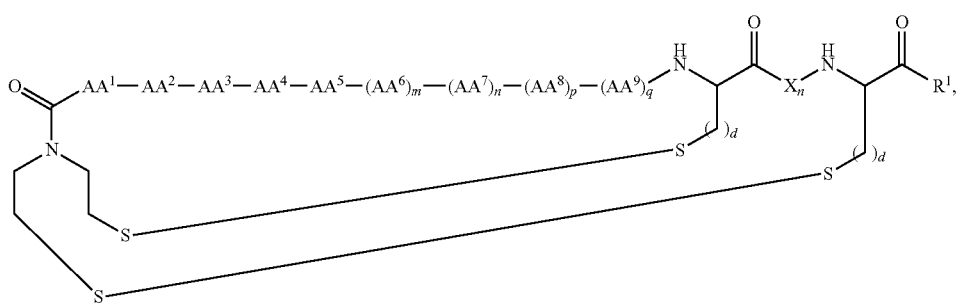

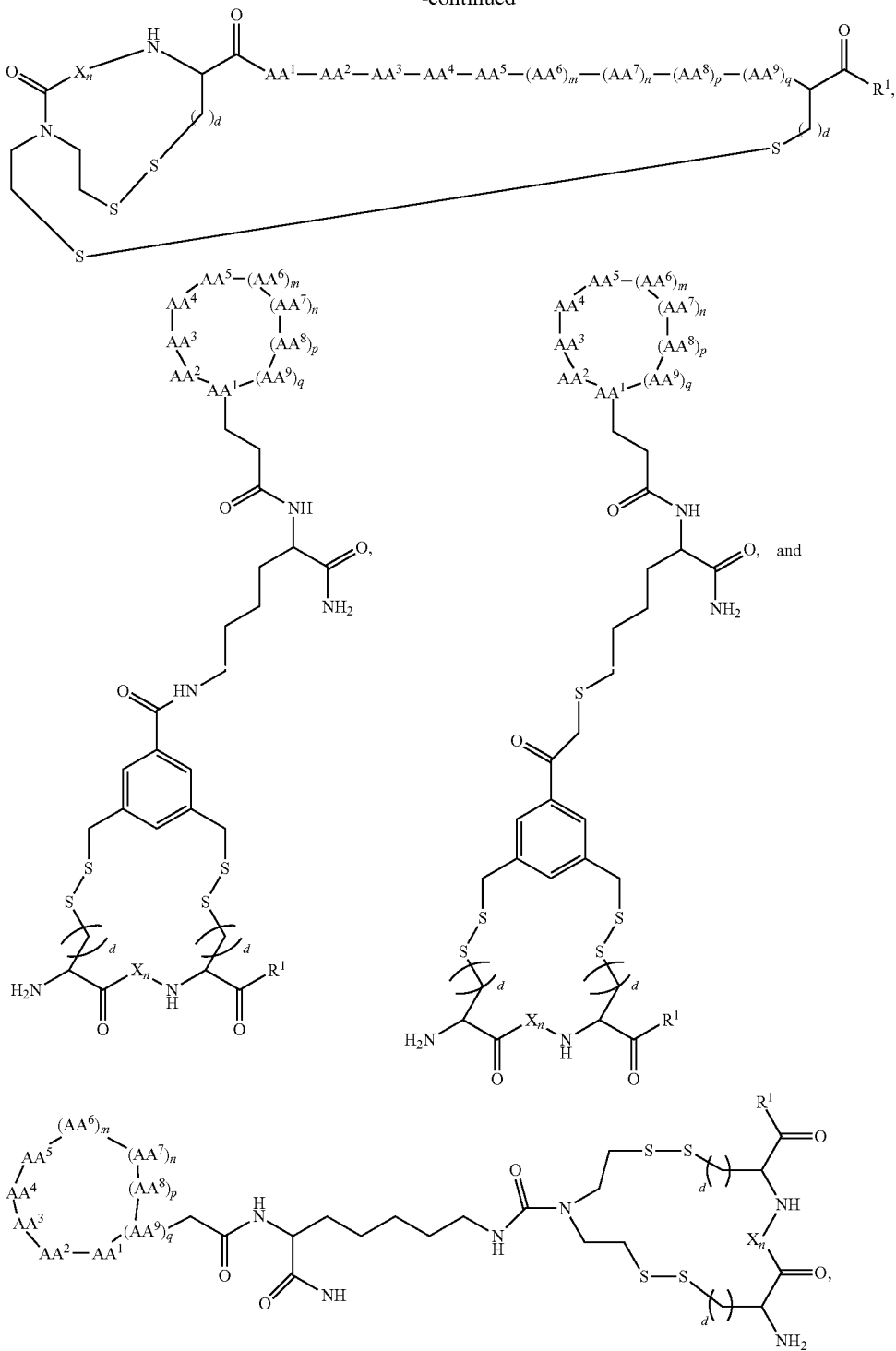

or a pharmaceutically acceptable salt thereof,
wherein each d is independently 1 or 2; and
wherein $R^1$ is OH, $OR^2$, $NHR^2$; and $R^2$ is a alkyl, aryl, heteroaryl, amino acid residue, peptide sequence of 2 to 20 amino acid residues, detectable moiety, or solid support.

In some embodiments, the at least two amino acid which independently comprise a hydrophobic side chain are selected from the group consisting of glycine, phenylglycine, alanine, valine, leucine, isoleucine, norleucine, phenylalanine, tryptophan, naphthylalanine, proline, and combinations thereof, wherein the aromatic side chains on phenylglycine, phenylalanine, tryptophan, or naphthylalanine are each optionally substituted with a halogen. In other embodiments, the at least two amino acid which independently comprise a hydrophobic side chain are independently selected from the group consisting of phenylalanine, naphthylalanine, and combinations thereof. In still other embodiments, the at least two amino acids which independently comprise a hydrophobic residue are consecutive amino acids.

In some embodiments:
AA$^1$ is L arginine;
AA$^2$ is L-arginine;
AA$^3$ is L-arginine;
AA$^4$ is L-phenylalanine;
AA$^S$ is L phenylalanine; and
m, n, p, and q, are each 0.
or
AA$^1$ is L-phenylalanine;
AA$^2$ is L-naphthylalanine;
AA$^3$ is L-arginine;
AA$^4$ is L-arginine;
AA$^5$ is L-arginine;
m is 1 and AA$^6$ is L-arginine; and
n, p, and q are each 0.
or
AA$^1$ is L-arginine;
AA$^2$ is L-arginine;
AA$^3$ is L-arginine;
AA$^4$ is L-arginine;
AA$^5$ is L-naphthylalanine;
m is 1 and AA$^6$ is L-phenylalanine; and
n, p, and q are each 0.

In some embodiments, at least three consecutive amino acids have alternating chirality. In other embodiments, the at least three consecutive amino acids having alternating chirality are arginines.

In some embodiments:
AA$^1$ is D-phenylalanine;
AA$^2$ is L-naphthylalanine;
AA$^3$ is L-arginine;
AA$^4$ is D-arginine;
AA$^5$ is L-arginine;
m is 1 and AA$^6$ is D-arginine; and
n, p, and q are each 0.
or
AA$^1$ is D-phenylalanine;
AA$^2$ is L-naphthylalanine;
AA$^3$ is L-arginine;
AA$^4$ is D-arginine;
AA$^5$ is L-arginine;
m and n are each 1, and AA$^6$ is D-arginine and AA$^1$ is L-arginine; and
p and q are each 0.
or
AA$^1$ is D-phenylalanine;
AA$^2$ is L-naphthylalanine;
AA$^3$ is L-arginine;
AA$^4$ is D-arginine;
AA$^5$ is L-arginine;
m and n are each 1, and AA$^6$ is D-arginine and AA$^7$ is L-phenylalanine; and
p and q are each 0.

In other embodiments, AA$^1$, AA$^2$, AA$^3$, AA$^4$, AA$^5$, AA$^6$, AA$^7$, AA$^8$, and AA$^9$ is selected from SEQ ID NO:62 through SEQ ID NO:146.

In some embodiments, the peptide sequence in X$_n$ inhibits at least one protein-protein interaction. In other embodiments, the protein-protein interaction is an interaction between a κB-kinase (IKK) complex and a regulatory protein NF-κB essential modifier (NEMO). In still other embodiments, the peptide sequence in X$_n$ is an inhibitor against Ras, PTP1 B, Pin 1, Grb2 SH2, MDM2, or combinations thereof. In yet still other embodiments, the peptide sequence in X$_n$ is a wild-type peptidyl ligand or a peptide mimetic.

In some embodiments, the provided herein are compounds according to Formula V-A, VI-A, VII-A, VIII-A, IX-A, X-A, or XII-A and XII-B:

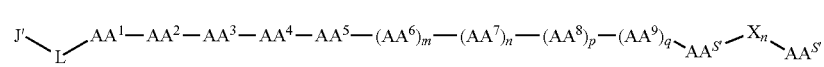

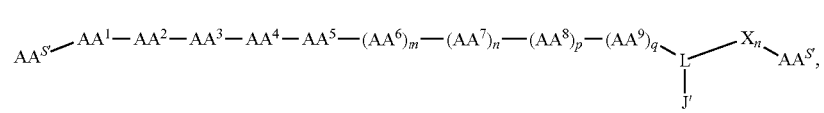

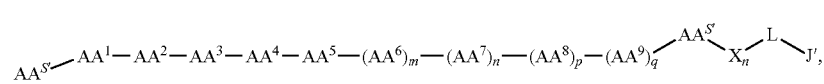

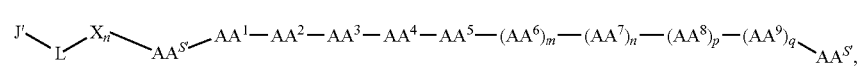

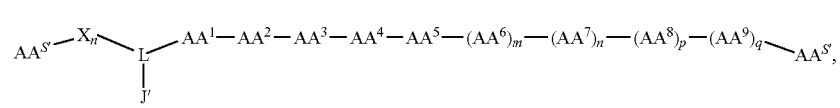

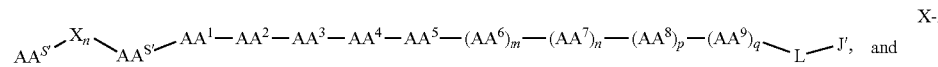

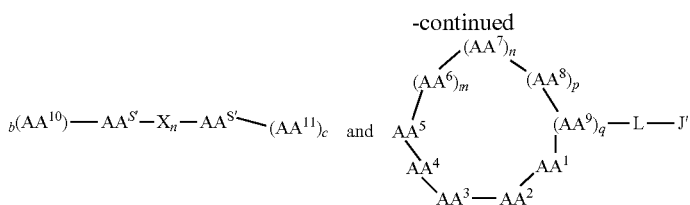

XII-A and XII-B or a pharmaceutically acceptable salt thereof,
wherein:
$AA^1$, $AA^2$, $AA^3$, $AA^4$, $AA^5$, $AA^6$, $AA^7$, $AA^8$, $AA^9$, $AA^1$, and $AA^{11}$ are independently selected from an amino acid, which is optionally substituted, where are at least three amino acids are arginine, and at least two amino acids independently comprise a hydrophobic side chain;

m, n, p, or q are independently selected from 0 and 1;

b and c are independently an integer from 0 to 20;

$AA^{S'}$ at each occurrence is independently a moiety which comprises a thiol;

J' is an alkyl, N-alkyl, alkenyl, alkynyl, carbocyclyl, or heterocyclyl, each of which are independently substituted with at least two thiol substituents; and L is an optional moiety which links $AA^{S'}$ to an amino acid, $X_n$, or a combination thereof; and $X_n$ is a cargo moiety comprising a peptide sequence having from 4 to 20 amino acids.

In some embodiments, J' is N-alkyl, aryl, or heteroaryl. In further embodiments, J' is

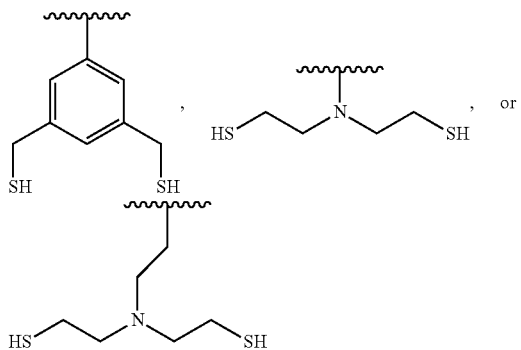

In some embodiments, L is absent, an amino acid,

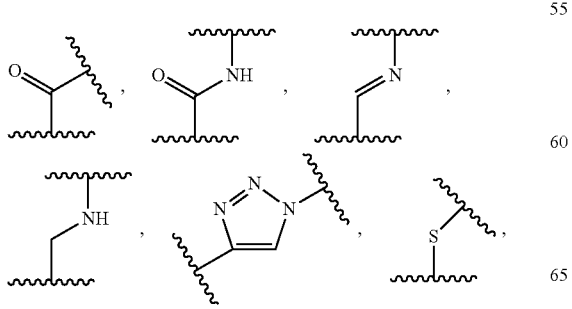

wherein a is an integer from 0 to 20.

In some embodiments, each $AA^{S'}$ is independently:

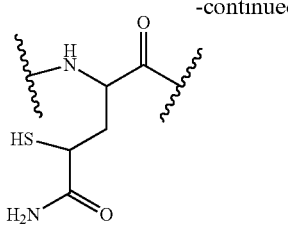
wherein the C-terminus of AA^{S'} forms an amide bond or is $R^1$, wherein $R^1$ is OH, $OR^2$, $NHR^2$; and wherein $R^2$ is a alkyl, aryl, heteroaryl, amino acid residue, peptide sequence of 2 to 20 amino acid residues, detectable moiety, or solid support.
In some embodiments, the compounds have a structure selected from the group consisting of
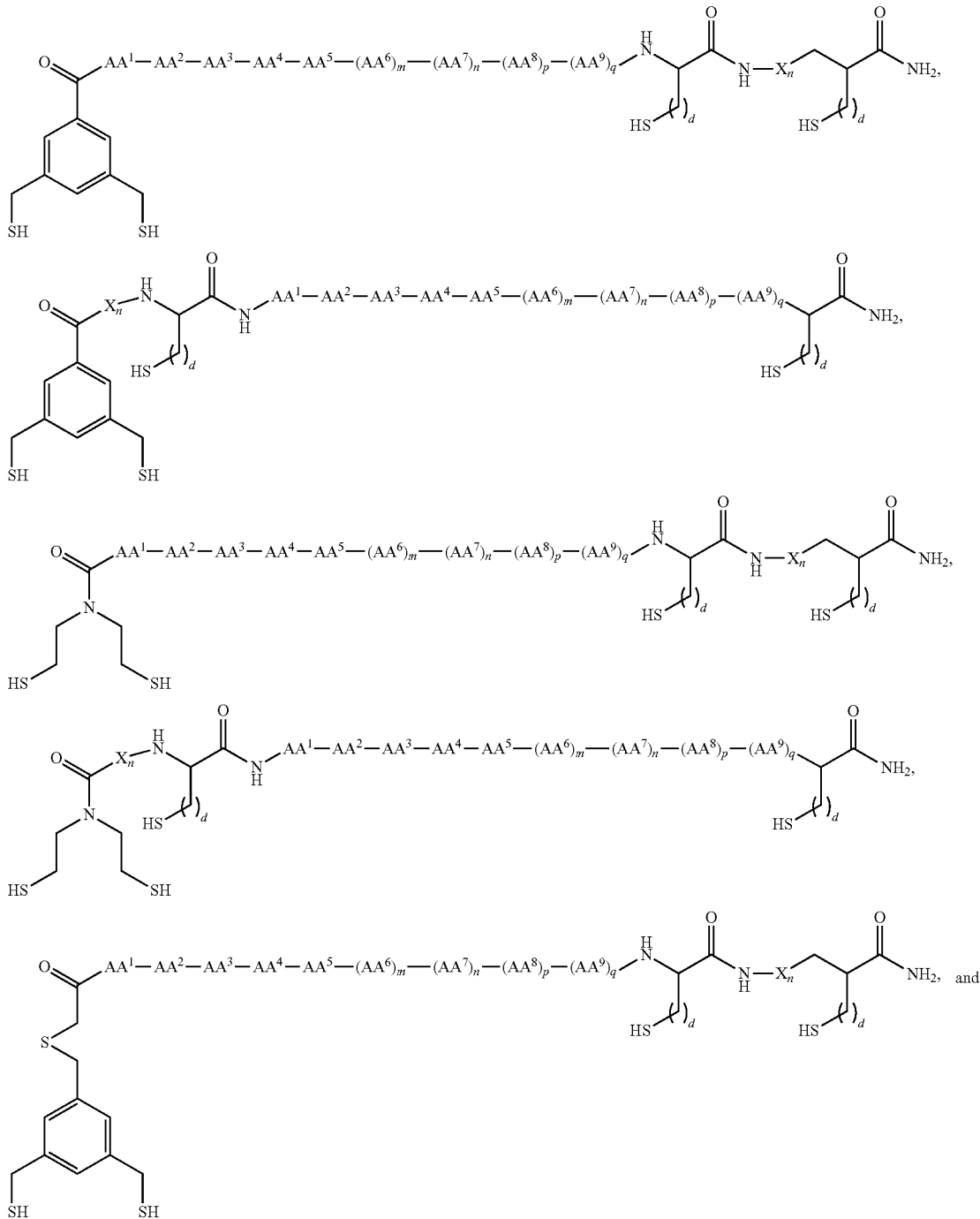

-continued

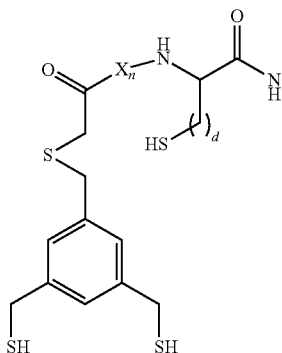

or a pharmaceutically acceptable salt thereof, wherein each d is independently 1 or 0.

In embodiments of the above compounds, the at least two amino acids which independently comprise a hydrophobic side chain are selected from the group consisting of glycine, phenylglycine, alanine, valine, leucine, isoleucine, norleucine, phenylalanine, tryptophan, naphthylalanine, proline, and combinations thereof, wherein the aromatic residues on phenylglycine, phenylalanine, tryptophan, naphthylalanine are optionally substituted. In other embodiments, the at least two amino acids which independently comprise a hydrophobic side chain are selected from the group consisting of phenylalanine, naphthylalanine, and combinations thereof. In still other embodiments, the at least two amino acids which independently comprise a hydrophobic side chain are consecutive amino acids.

In some embodiments:
$AA^1$ is L arginine;
$AA^2$ is L-arginine;
$AA^3$ is L-arginine;
$AA^4$ is L-phenylalanine;
$AA^5$ is L phenylalanine; and
m, n, p, and q, are each 0.
or
$AA^1$ is L-phenylalanine;
$AA^2$ is L-naphthylalanine;
$AA^3$ is L-arginine;
$AA^4$ is L-arginine;
$AA^5$ is L-arginine;
m is 1 and $AA^6$ is L-arginine; and
n, p, and q are each 0.
or
$AA^1$ is L-arginine;
$AA^2$ is L-arginine;
$AA^3$ is L-arginine;
$AA^4$ is L-arginine;
$AA^5$ is L-naphthylalanine;
m is 1 and $AA^6$ is L-phenylalanine; and
n, p, and q are each 0.

In some embodiments, at least three consecutive amino acids have alternating chirality. In other embodiments, the at least three consecutive amino acids having alternating chirality are arginines.

In some embodiments:
$AA^1$ is D-phenylalanine;
$AA^2$ is L-naphthylalanine;
$AA^3$ is L-arginine;
$AA^4$ is D-arginine;
$AA^5$ is L-arginine;
m is 1 and $AA^6$ is D-arginine; and
n, p, and q are each 0.
or
$AA^1$ is D-phenylalanine;
$AA^2$ is L-naphthylalanine;
$AA^3$ is L-arginine;
$AA^4$ is D-arginine;
$AA^5$ is L-arginine;
m and n are each 1, and $AA^6$ is D-arginine and $AA^1$ is L-arginine; and
p and q are each 0.
or
$AA^1$ is D-phenylalanine;
$AA^2$ is L-naphthylalanine;
$AA^3$ is L-arginine;
$AA^4$ is D-arginine;
$AA^5$ is L-arginine;
m and n are each 1, and $AA^6$ is D-arginine and $AA^1$ is L-phenylalanine; and
p and q are each 0.

In other embodiments, $AA^1$, $AA^2$, $AA^3$, $AA^4$, $AA^5$, $AA^6$, $AA^7$, $AA^8$, and $AA^9$ is selected from SEQ ID NO:62 through SEQ ID NO:146.

In some embodiments, the peptide sequence in $X_n$ inhibits at least one protein-protein interaction. In further embodiments, the protein-protein interaction is an interaction between a κB-kinase (IKK) complex and a regulatory protein NF-κB essential modifier (NEMO). In other embodiments, the peptide sequence in $X_n$ is an inhibitor against Ras, PTP1 B, Pin 1, Grb2 SH2, MDM2, or combinations thereof. In still other embodiments, the peptide sequence in $X_n$ is a peptidyl is a wild-type peptide ligand or a peptide mimetic.

In various embodiments, a compound according to Formula XI is disclosed:

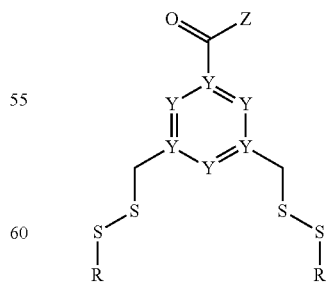

XI wherein:
Y at each instance is independently CH, N, O or S, provided no more than four Y are N, O, S, or combinations thereof;

Z is OR$_a$, hydrogen, halogen, carbocyclyl, heterocyclyl, or an amino acid;

R at each instance is independently an alkyl, alkenyl, alkynyl, carbocyclyl, heterocyclyl, or an amino acid; and R$_a$ is independently H, C(O)alkyl, alkyl, alkenyl, alkynyl, carbocyclic, or heterocyclyl.

In some embodiments, Y is independently CH. In other embodiments, the compound has a structure according to Formula XI-A:

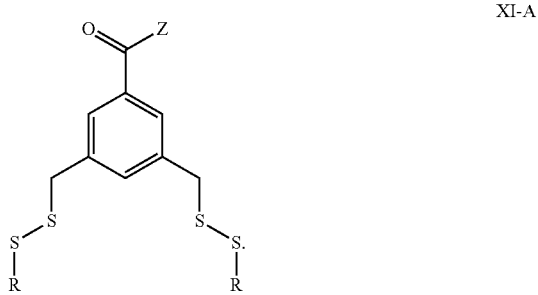

XI-A

In some embodiments, each R is independently aryl or hetereoaryl. In further embodiments, the compound has a structure according to Formula XI-B:

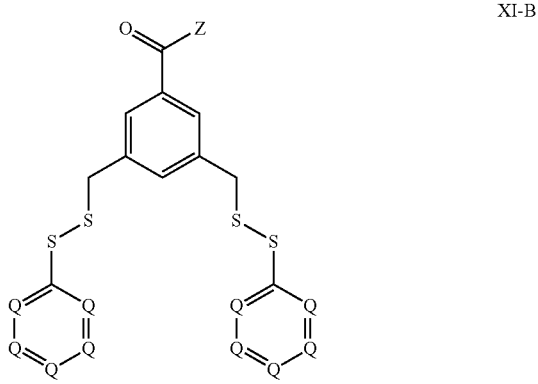

XI-B wherein Q at each instance is independently CH or N.

In some embodiments, Z is OH. In other embodiments, the compound has the following structure:

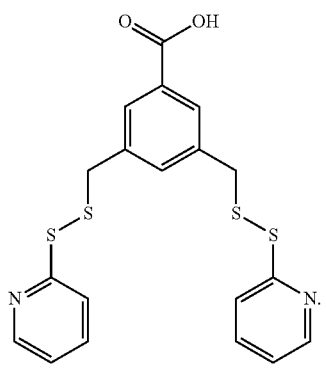 [SMILES: O=C(O)c1cc(CSSc2ccccn2)cc(CSSc2ccccn2)c1]

Also disclosed herein are methods of delivering a therapeutic agent to cytoplasm of a cell, comprising administering a compound of the formulae V-X or XII.

Also disclosed are pharmaceutical compositions comprising a bicyclic peptide disclosed herein and a pharmaceutical carrier Also disclosed herein are methods of treating or preventing a disorder in a subject, such as a human, comprising administering to the subject an effective amount of a compound disclosed herein or a pharmaceutically acceptable salt thereof. In some examples, the subject is an animal, such as a human. In some examples, the subject is identified as having a need for treatment of the disorder. In some examples, the method treats a disorder. In some examples, the disorder is associated with aberrant NF-κB signaling. In some examples the disorder is associated with uncontrolled cellular proliferation, such as cancer. In some examples, the disorder is cancer. In some examples the disorder is an inflammatory disorder, such as irritable bowl syndrome. In some examples, the disorder is an autoimmune disorder, such as a disorder selected from rheumatoid arthritis, ankylosing spondylitis, Crohn's disease, psoriasis, hidradenitis suppurativa, and refractory asthma. In some further examples, disclosed herein is a method of treating Duchenne muscular dystrophy or large B-cell lymphoma.

Also disclosed herein is a method for identifying a drug candidate for treatment of a disorder, the method comprising the steps of: exposing a compound disclosed herein, a compound prepared by the methods disclosed herein, a library disclosed herein, or a library prepared by the methods disclosed to a receptor associated with the disorder; b) detecting reaction between the receptor and the compound or the library; and c) determining the identity of compound reacting with the receptor.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION OF FIGURES

The accompanying figures, which are incorporated in and constitute a part of this specification, illustrate several aspects and together with the description serve to explain the principles of the invention.

FIG. 1A shows MFI of HeLa cells after 2-h treatment with 5 μM FITC-labeled peptide cFΦR4 (SEQ ID NO.:68) or 1-5, as determined by flow cytometry analysis. Blank, no peptide. FIG. 1B shows inhibition of the NEMO-IKKγ interaction by peptides 1, 4, and 5 as monitored by the HTRF assay. FIG. 1C shows dose-dependent inhibition of TNFα induced activation of NF-κB signaling in HEK293 cells by peptides 1, 4, and 5. FIG. 1D shows a comparison of the serum stability of peptides 1, 4, and 6. Data reported are the mean±SD of three independent experiments.

DETAILED DESCRIPTION

Figure 2:
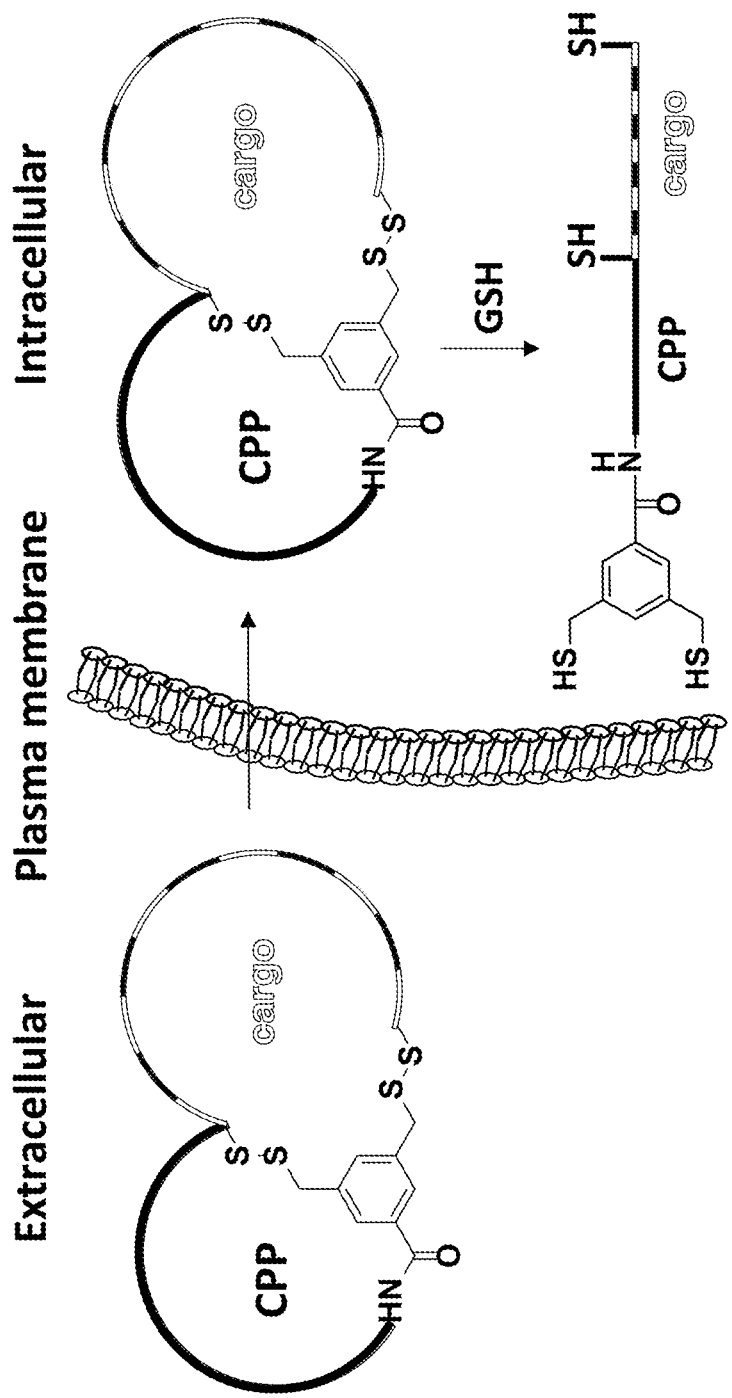
FIG. 2 is a reversible peptide bicyclization strategy. GSH, glutathione.

The present invention can be understood more readily by reference to the following detailed description of the invention and the Examples and Figures included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

General Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" refers to the target of administration, e.g. a subject. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, fish, bird, or rodent. The term does not denote a particular age or sex. Thus, adult and newborn subjects, as well as fetuses, whether male or female, are intended to be covered. In some examples, the subject is a mammal. A patient refers to a subject afflicted with a disease or disorder. The term "patient" includes human and veterinary subjects. In some examples of the disclosed methods, the subject has been diagnosed with a need for treatment of cancer prior to the administering step. In some examples of the disclosed method, the subject has been diagnosed with cancer prior to the administering step. The term subject also includes a cell, such as an animal, for example human, cell.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In some examples, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In some examples, the subject is a mammal such as a primate, and, in some examples, the subject is a human. The term "subject" also includes domesticated animals (e.g., cats, dogs, etc.), livestock (e.g., cattle, horses, pigs, sheep, goats, fish, bird, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with cancer" means having been subjected to a physical examination by a person of skill, for example, a physician, and found to have a condition that can be diagnosed or treated by a compound or composition that can treat or prevent cancer. As a further example, "diagnosed with a need for treating or preventing cancer" refers to having been subjected to a physical examination by a person of skill, for example, a physician, and found to have a condition characterized by cancer or other disease wherein treating or preventing cancer would be beneficial to the subject.

As used herein, the phrase "identified to be in need of treatment for a disorder," or the like, refers to selection of a subject based upon need for treatment of the disorder. For example, a subject can be identified as having a need for treatment of a disorder (e.g., a disorder related to cancer) based upon an earlier diagnosis by a person of skill and thereafter subjected to treatment for the disorder. It is contemplated that the identification can, In some examples, be performed by a person different from the person making the diagnosis. It is also contemplated, in some examples, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In some examples, a preparation can be administered therapeutically; that is, administered to treat an existing disease or condition. In some examples, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In some examples, a preparation can be administered in a "prophylactically effective amount"; that is, an amount effective for prevention of a disease or condition.

As used herein, "$EC_{50}$," is intended to refer to the concentration or dose of a substance (e.g., a compound or a drug) that is required for 50% enhancement or activation of a biological process, or component of a process, including a protein, subunit, organelle, ribonucleoprotein, etc. $EC_{50}$ also refers to the concentration or dose of a substance that is required for 50% enhancement or activation in vivo, as further defined elsewhere herein. Alternatively, $EC_{50}$ can refer to the concentration or dose of compound that provokes a response halfway between the baseline and maximum response. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein the gene or genes has been introduced or knocked-out, as appropriate, to replicate a disease process.

As used herein, "$IC_{50}$," is intended to refer to the concentration or dose of a substance (e.g., a compound or a drug) that is required for 50% inhibition or diminution of a biological process, or component of a process, including a protein, subunit, organelle, ribonucleoprotein, etc. $IC_{50}$ also refers to the concentration or dose of a substance that is required for 50% inhibition or diminution in vivo, as further defined elsewhere herein. Alternatively, $IC_{50}$ also refers to the half maximal (50%) inhibitory concentration (IC) or inhibitory dose of a substance. The response can be measured in an in vitro or in vivo system as is convenient and appropriate for the biological response of interest. For example, the response can be measured in vitro using cultured muscle cells or in an ex vivo organ culture system with isolated muscle fibers. Alternatively, the response can be measured in vivo using an appropriate research model such as rodent, including mice and rats. The mouse or rat can be an inbred strain with phenotypic characteristics of interest such as obesity or diabetes. As appropriate, the response can be measured in a transgenic or knockout mouse or rat wherein a gene or genes has been introduced or knocked-out, as appropriate, to replicate a disease process.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester. As another example, an amino acid residue, e.g., in a peptide, refers to one or more -AA- moieties, and such residues may be referred to herein interchangeably as an amino acid or an amino acid residue.

Chemical Definitions

As used herein, the term "substituted" is contemplated to include all permissible substituents of organic compounds. In some examples, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain examples, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$—(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

"Carbocyclyl," "carbocyclic ring" or "carbocycle" refers to a ring structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. The carbocyclic group can be substituted or unsubstituted. The carbocyclic group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_m$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

"N-alkyl" refers to a alkyl radical as defined above containing at least one nitrogen and where a point of attachment of the alkyl radical to the rest of the molecule is through a nitrogen atom in the N-alkyl radical. Unless stated otherwise specifically in the specification, a N-alkyl group can be optionally substituted.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds can contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group, and when more than one position in any given structure can be substituted with more than one substituent selected from a specified group, the substituent can be either the same or different at every position. Combinations of substituents envisioned herein are preferably those that result in the formation of stable or chemically feasible compounds. In is also contemplated that, in some examples, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in some examples, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH=CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR^{\circ}$, $SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —SC(S)SR$^{\circ}$, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —$(C_{1-4}$ straight or branched)alkylene)O—$N(R^{\circ})_2$; or —$(C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —O(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —C(O)SR, —$(C_{1-4}$ straight or branched alkylene)C(O)OR., or —SSR$^\bullet$ wherein each R$^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, or —$NO_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —$NH_2$, —NHR$^\bullet$, —NR$^\bullet_2$, or —$NO_2$, wherein each is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In some examples, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

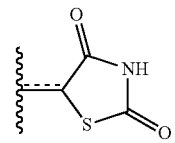

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the compounds and compositions disclosed herein unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In some examples, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, di alkylcarboxamide, substituted di alkylcarboxamide, alkyl sulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

As used herein, the symbol

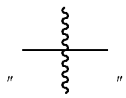

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

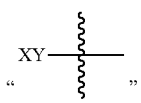

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

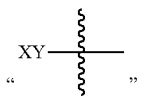

infers that when $R^3$ is "XY", the point of attachment bond is the same bond as the bond by which $R^3$ is depicted as being bonded to $CH_3$.

Compounds described herein can contain one or more double bonds and, thus, potentially give rise to cis/trans (E/Z) isomers, as well as other conformational isomers. Unless stated to the contrary, the compounds and compositions disclosed herein include all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the compounds and compositions disclosed herein include all such possible diastereomers as well as their racemic mixtures, their substantially pure resolved enantiomers, all possible geometric isomers, and pharmaceutically acceptable salts thereof Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds disclosed herein include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds and prodrugs thereof can generally be prepared by carrying out the procedures below, by substituting a readily available isotopically labeled reagent for a non-isotopically labeled reagent.

The compounds described herein can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds disclosed herein to form solvates and hydrates. Unless stated to the contrary, all such possible solvates are included in the discussion herein.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

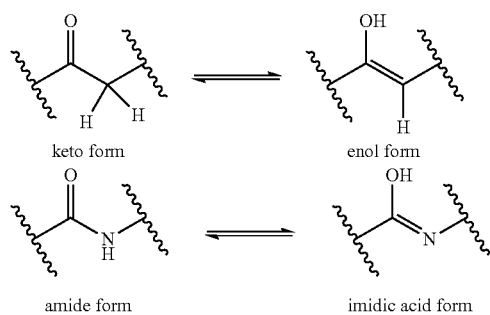

Likewise, amides with an N-hydrogen can exist in an equilibrium of the amide form and the imidic acid form. Unless stated to the contrary, all such possible tautomers are included herein.

It is known that chemical substances form solids which are present in different states of order which are termed polymorphic forms or modifications. The different modifications of a polymorphic substance can differ greatly in their physical properties. The compounds can be present in different polymorphic forms, with it being possible for particular modifications to be metastable. Unless stated to the contrary, all such possible polymorphic forms are included.

In some examples, a structure of a compound can be represented by a formula:

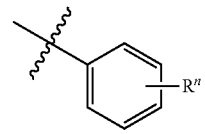

which is understood to be equivalent to a formula:

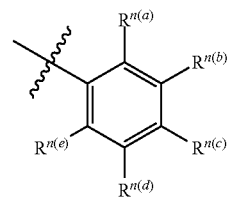

wherein n is typically an integer. That is, $R^n$ is understood to represent five independent substituents, $R^{n(a)}$, $R^{n(b)}$, $R^{n(c)}$, $-R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions disclosed herein as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods disclosed herein.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Abbreviations used herein are as follows: Cpa, L-4-chlorophenylalanine; dap, D-2,3-diaminopropionic acid; Dap, L-2,3-diaminopropionic acid; FITC, fluorescein isothiocyanate; Fpa, L-4-fluorophenyl alanine; $F_2pa$, L-3,4-difluorophenylalanine; fpa, D-2-fluorophenylalanine; $f_2pa$, D-3,4-difluorophenylalanine; Nal, L-2-naphthylalanine; Nle, norleucine; Phg, L-α-phenylglycine; Sar, sarcosine; TNFα, tumor necrosis factor-alpha; TNFR, TNFα receptor.

Compounds

Cyclo(FΦRRRRQ) (cFΦR$^4$, where Φ is L-2-naphthylalanine (SEQ ID NO.:72)) was previously reported as a member of a class of cyclic CPPs (Z. Qian, et al., *ACS Chem. Biol.* 2013, 8, 423; Z. Qian, et al., *Biochemistry* 2014, 53, 4034). These CPPs bind directly to the membrane phospholipids, enter cells by endocytosis, and efficiently escape from the early endosome into the cytosol by inducing budding of small, unstable vesicles (Id.; Z. Qian, et al., *Biochemistry* 2016, 55, 2601). With a cytosolic delivery efficiency (defined as the ratio of cytosolic over extracellular cargo concentration) of 20%, cFΦR$^4$ (SEQ ID NO.:72) is an order of magnitude more active than Tat, one of the most widely used CPPs (Id.). Most importantly, cFΦR4 (SEQ ID NO.:72) and other cyclic CPPs are capable of efficiently delivering a variety of cargo molecules including small molecules, peptides, and proteins into the cytosol of mammalian cells. For example, short peptidyl cargos were directly incorporated into the cFΦR$^4$ (SEQ ID NO.:72) ring (endocyclic delivery) and the resulting cyclic peptides were cell-permeable (Id.; P. Upadhyaya, et al., *Angew. Chem., Int. Ed.* 2015, 54, 7602; *Angew. Chem.* 2015, 127, 7712). cFΦR$^4$ (SEQ ID NO.:72) was also fused with 5.7 million different cyclic peptides to generate a library of cell-permeable bicyclic peptides (bicyclic delivery) (T. B. Trinh, P et al., *ACS Comb. Sci.* 2016, 18, 75). However, many peptide ligands must be in their extended conformations to be biologically active and are not compatible with the above cyclization approaches. To this end, a reversible cyclization strategy for intracellular delivery of linear peptidyl ligands was developed by fusing them with FΦR$_4$ (SEQ ID NO.:72) and cyclizing the fusion peptides through a disulfide bond (Z. Qian, et al., *Angew. Chem. Int. Ed.* 2015, 54, 5874; *Angew. Chem.* 2015, 127, 5972). Unfortunately, the previous approach is limited to relatively short peptides, as cyclization of longer peptides results in large rings, whose conformational flexibility limits the gains in metabolic stability and cell-permeability (Z. Qian, et al., *ACS Chem. Biol.* 2013, 8, 423; Z. Qian, et al., *Biochemistry* 2014, 53, 4034). Cyclization via an internal thiol-containing moieties (e.g., the AA$^S$ groups disclosed herein) results in smaller rings and better cellular uptake, but leaves a portion of the peptidyl cargo in the linear form, which remains susceptible to proteolytic degradation. To overcome this limitation, disclosed herein is a reversible bicyclization strategy, which allows the entire CPP-cargo fusion to be converted into a bicyclic structure by the formation of a pair of disulfide bonds (FIG. 2). When outside the cell, the peptide exists as a highly constrained bicycle, which possesses enhanced cell permeability and proteolytic stability. Upon entering the cytosol, the disulfide bonds are reduced by the intracellular glutathione (GSH) to produce the linear, biologically active peptide. The bicyclic system permits the formation of a small CPP ring for optimal cellular uptake and a separate cargo ring to accommodate peptides of different lengths.

In various embodiments, the reversible bicyclic peptides described herein comprise a first cyclic peptide sequence and a second cyclic peptide sequence. In some embodiments, the first cyclic peptide sequence comprises a cell-penetrating sequence ($X_m$). In other embodiments, the second cyclic peptide sequence comprises a cargo peptide sequence ($X_n$).

In some embodiments, $X_m$ and $X_n$ are fused. In some embodiments, the fusion occurs between the C-terminus of $X_m$ and the N-terminus of $X_n$. In other embodiments, the fusion occurs between the N-terminus $X_m$ and the C-terminus of $X_n$. In further embodiments, an amino acid or a linking moiety may be used to fuse $X_m$ and $X_n$. In still other embodiments, the amino acid or a linking moiety used to fuse $X_m$ and $X_n$ forms at least one intramolecular disulfide bond, thereby forming the bicyclic peptide sequence. In further embodiments, the amino acid which fuses $X_m$ and $X_n$ is represented by AA$^S$. In other embodiments, the linking moiety may be represented by "L-J" in the formulae provided herein.

In some embodiments, $X_m$ may be conjugated, directed or indirectly, to $X_n$ For example, in some embodiments, $X_m$ may comprise at least two AA$^S$ moeities, and $X_n$ may comprise at least two AA$^S$ moeities, and the $X_m$ may be directly conjugated to $X_n$ via two disulfide bonds formed between opposing AA$^S$ residues on $X_m$ and $X_n$, respectively. In other embodiments, the linking moiety is covalently bound a side chain of an amino acid in $X_m$, and $X_n$ comprises at least two AA$^S$ moeities, each of which form disulfide bonds with a linking moiety. Amino acids having side chains which are suitable for conjugating the linking moiety include asparagine, glutamine, aspartate, glutamate, and lysine. Further, amino acids may be appropriately modified for conjugation with the linking moiety.

As discussed above, to some embodiments, the bicyclic peptides described herein comprise a linking moiety. In some embodiments, $X_m$ is cyclized through a linking moiety. In other embodiments, $X_n$ is cyclized through a linking moiety. In still other embodiments, each of $X_m$ and $X_n$ are independently cyclized through the linking moiety. In certain embodiments, only $X_n$ is cyclized through a linking moiety, $X_m$ is a cyclic peptide sequence, and the linking moiety conjugates $X_n$ and $X_m$, thereby forming the bicyclic peptides disclosed herein.

In certain embodiments, the precursor to the linking moiety comprises at least two thiol groups which form at least two intramolecular disulifde bonds, thereby forming the bicyclic peptides disclosed herein. In these embodiments, the disulfide bonds can be reduced by intracellular GSH to form a linear peptide sequence comprising $X_m$ and $X_n$, to release a linear sequence comprising $X_m$ (in which case $X_n$ remains cyclic), or a linear sequence comprising $X_n$ (in which case $X_n$ remains cyclic). In certain embodiments after entry into the cytosol of the cell the disulfide bonds are reduced by intracellular GSH to thereby release a linear sequence comprising $X_n$. In other embodiments, intracellular GSH reduces the two disulfide bonds to thereby release a linear sequence comprising $X_m$ and $X_n$. In still other embodiments, a precursor to the linking moiety comprises three thiol groups, which form three intramolecular disulfide bonds in the bicyclic peptides disclosed herein. In still other embodiments, a precursor to the linking moiety comprises four thiol groups, which form four intramolecular disulfide bonds.

Accordingly, disclosed herein, in various embodiments, are bicyclic peptides according to Formulae 1-12.

| Number | Formula |
|---|---|
| 1 | $X_m$, $X_n$, L, J, SS, $AA^S$ (ring structure) |
| 2 | L—$X_m$—$AA^S$—$X_n$ with SS, $AA^S$, J, SS connections |
| 3 | $AA^S$—$X_m$—L—$X_n$—$AA^S$ with SS—J—SS |
| 4 | $X_m$—$AA^S$—$X_n$—L with $AA^S$, SS, SS, J |
| 5 | L—$X_n$—$AA^S$—$X_m$ with SS, $AA^S$, J, SS |
| 6 | $X_n$—L—$X_m$—$AA^S$ with $AA^S$, SS—J—SS |
| 7 | $X_n$—$AA^S$—$X_m$—L with $AA^S$, SS, SS, J |
| 8 | $X_n$—$AA^S$—$X_m$ with $AA^S$, SS, $AA^S$, SS—J—SS |
| 9 | $X_m$—$AA^S$—$X_n$ with $AA^S$, SS, $AA^S$, SS—J—SS |
| 10 | $X_n$($AA^S$—SS, $AA^S$—SS)—J—(SS—$AA^S$, SS—$AA^S$)$X_m$ |
| 11 | $X_m$—L—J—(SS—$AA^S$, SS—$AA^S$)—$X_n$ |
| 12 | $X_m$—L—$AA^S$—$X_n$—$AA^S$ with SS | wherein:

$X_m$ and $X_n$ independently comprise a sequence of 1-50 (e.g., 4-10) natural or non-natural amino acids, wherein $X_m$ corresponds to a cell-penetrating peptide (CPP) sequence as defined herein and $X_n$ corresponds to a cargo peptide sequence as defined herein;

$AA^S$ at each occurrence is independently a moiety which forms a disulfide bond with J;

J is absent, or an alkyl, N-alkyl, alkenyl, alkynyl, carbocyclyl, or heterocyclyl, each of which are independently substituted with at least two substituents which independently form a disulfide bond with $AA^S$ at each occurrence;

SS at each instance represents a disulfide bond; and

L is absent or a moiety which links $AA^S$ to an amino acid in $X_m$, $X_n$, or a combination thereof.

As shown above in Formulae 1-12, $X_n$ can be located on the N-terminus or C-terminus of $X_m$. In some embodiments, L is present and can be linked to the N-terminus or C-terminus of $X_m$, $X_n$ or $AA^S$. In other embodiments, L is present and can be located between and linked to each of $X_m$ and $X_n$, $X_m$ and $AA^S$, and/or $X_n$ and $AA^S$. In some embodiments, one or more $AA^S$ may be located in the $X_n$. In such embodiments, the $AA^S$ may be a component of the wild type peptide sequence (i.e., $X_n$) or $AA^S$ may be introduced into the peptide sequence ($X_n$). In some embodiments, the cargo peptide sequence ($X_n$) has two $AA^S$ (e.g., Formula 11), which allows for the cargo peptide sequence to be cleaved from the CPP sequence after the compound enters the cytosol.

As used herein, "L" refers to a connection between J and $X_m$, $X_n$, or combinations thereof. For example, in embodiments, L may comprise a moiety which is formed between a functional group on a precursor of J and amine group on an amino acid (e.g., on $X_m$ or $X_n$). The amine group may be the N-terminus or it may be an amine group on a side chain of an amino acid, e.g., on $X_m$. In such embodiments, the precursor of J can include a carboxylic acid moiety or derivative thereof (e.g., a haloketone), which thereby forms an amide bond with the N-terminus on the amino acid or cargo. In other embodiments, L may comprise a moiety which is formed between a functional group on a precursor of J and a carboxylic acid group on an amino acid (e.g., on $X_m$ or $X_n$). The carboxylic group may be the C-terminus or it may be an carboxylic acid group on a side chain of an amino acid, e.g., on $X_m$. In such embodiments, the precursor of J includes an amine, which thereby forms an amide bond with the C-terminus of the amino acid or the cargo. Non-limiting examples of L include at least one amino acid, alkyl, alkenyl, alkynyl, carbonyl, amide, imine, enamine, alkene, alkyne, disulfide, thioketone, sulfonylketone, carbamoyl, carbonyloxy, disulfide, thioether, and triazole. In embodiments, L is absent, an amino acid,

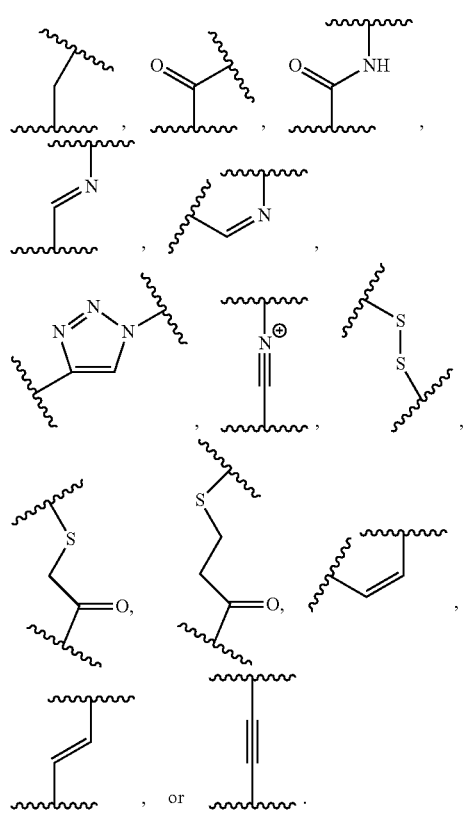

As defined above, in various embodiments, J may be an alkyl, N-alkyl, alkenyl, alkynyl, carbocyclyl, or heterocyclyl, each of which are independently substituted with at least two substituents which independently form a disulfide bond with $AA^S$ at each occurrence. In some embodiments, J comprises at least two substituents which independently form a disulfide bond with $AA^S$ at each occurrence. In other embodiments, J comprises at least three substituents which independently form a disulfide bond with $AA^S$ at each occurrence. In still other embodiments, J comprises at least four substituents which independently form a disulfide bond with $AA^S$ at each occurrence.

In some embodiments, L is absent, and J comprises three substituents which independently form a disulfide bond with $AA^S$ at each occurrence. Examples of such a bicyclic peptide are provided in Formulae 8 and 9.

In other embodiments, L is absent, and J comprises at four substituents which independently form a disulfide bond with $AA^S$ at each occurrence. An example of such a bicyclic peptide is provided in Formula 10.

In some embodiments, J is absent, and L links $X_m$ and $AA^1$.

In some embodiments, each of J and L are present. In some such embodiments, J and L can be located on the N-terminus of $X_n$ or $X_m$ and can represented by at least one of the following (prior to forming disulfide bonds):

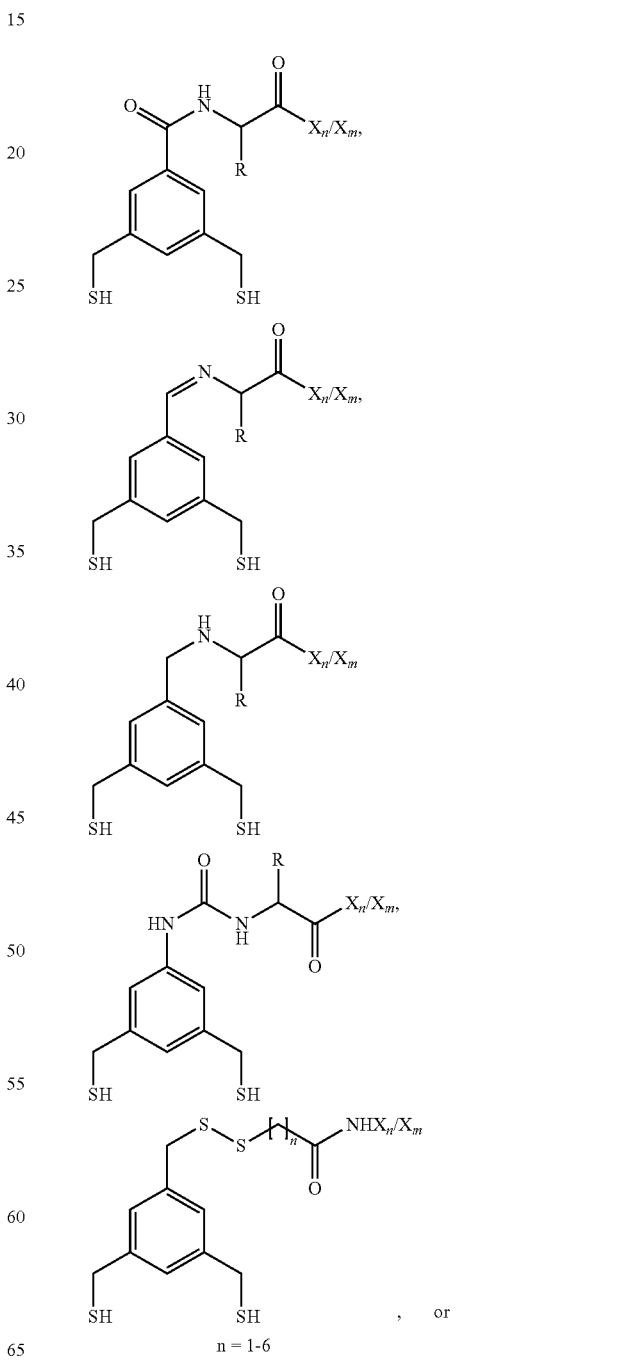

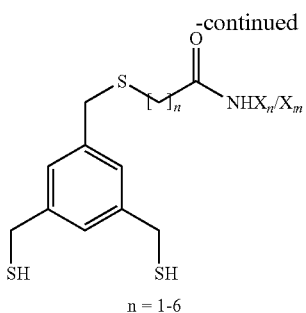

n = 1-6 wherein R represents the side of an amino acid which can be part of the peptide sequence comprising $X_m$ or $X_n$ which can be part of L.

In other such embodiments, J and L can be located between $X_n$ and $X_m$, between $X_m$ and $X_n$, or at the C-terminus of either of $X_n$ and $X_m$, and can be represented by one of the following (prior to forming disulfide bonds):

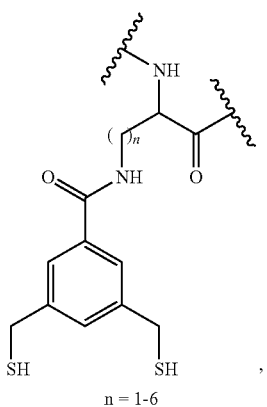

n = 1-6

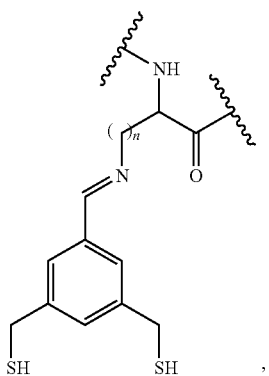

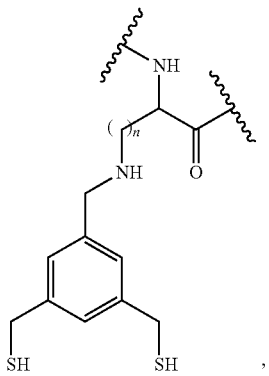

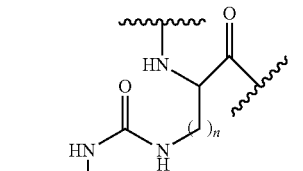

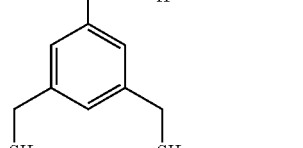

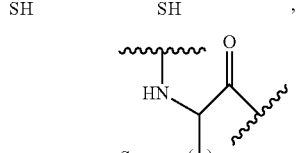

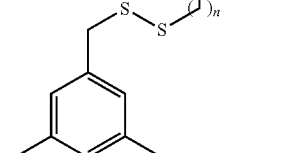

n = 0 or 1

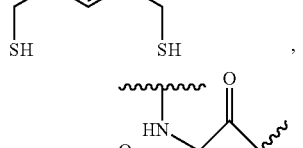

, or

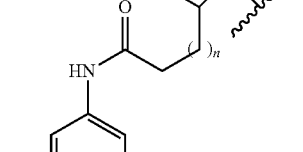

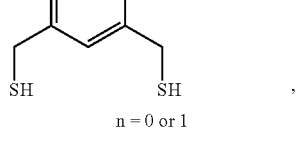

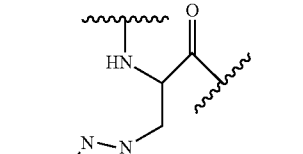

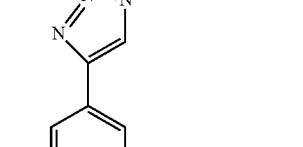

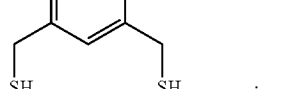

To form the bicyclic peptides of the present disclosure, the hydrogen on the thiol group of the above structures are independently replaced by a bond to a sulfur group.

In some embodiments, each $AA^1$ is independently an amino acid, or analog or derivative thereof, which is capable of forming a disulfide bond (e.g., an amino acid which has a thiol group prior to forming a disulfide bond). Non-limiting examples of such amino acids, or analogs or derivatives thereof, include:

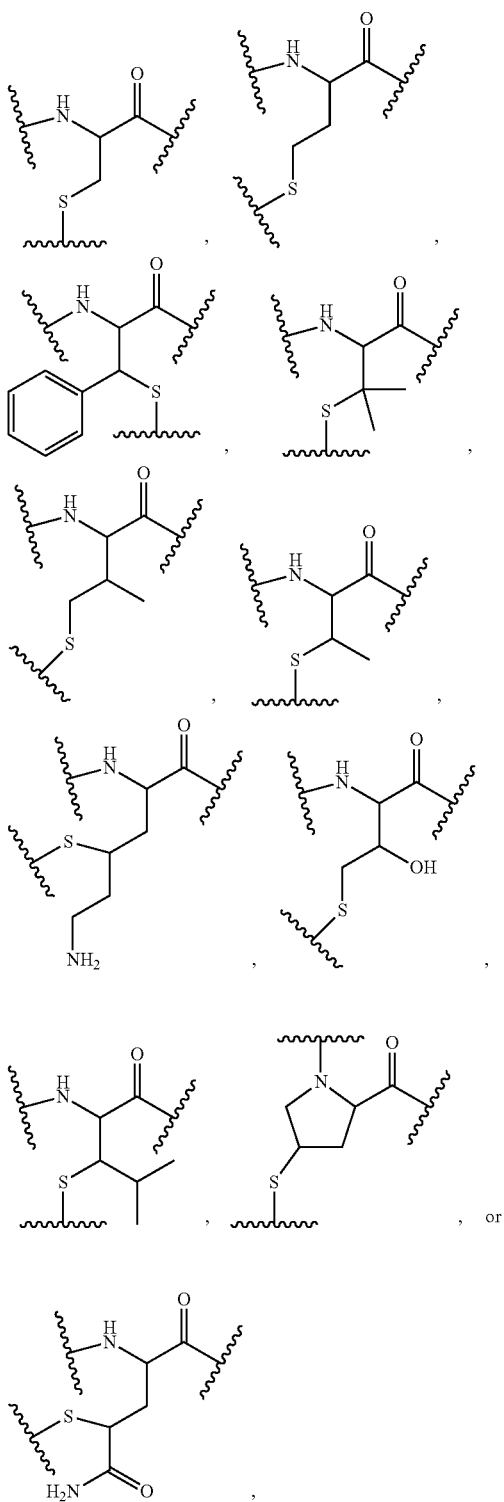

wherein the C-terminus of AA$^S$ forms an amide bond or R$^1$, wherein R$^1$ is OH, OR$^2$, NHR$^2$; and wherein R$^2$ is a alkyl, aryl, heteroaryl, amino acid residue, peptide sequence of 2 to 20 amino acid residues, detectable moiety, or solid support.

In some embodiments, a compound of Formula 9 has the following formula:

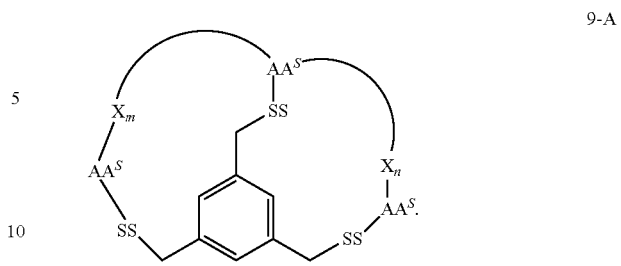

Figure 8:
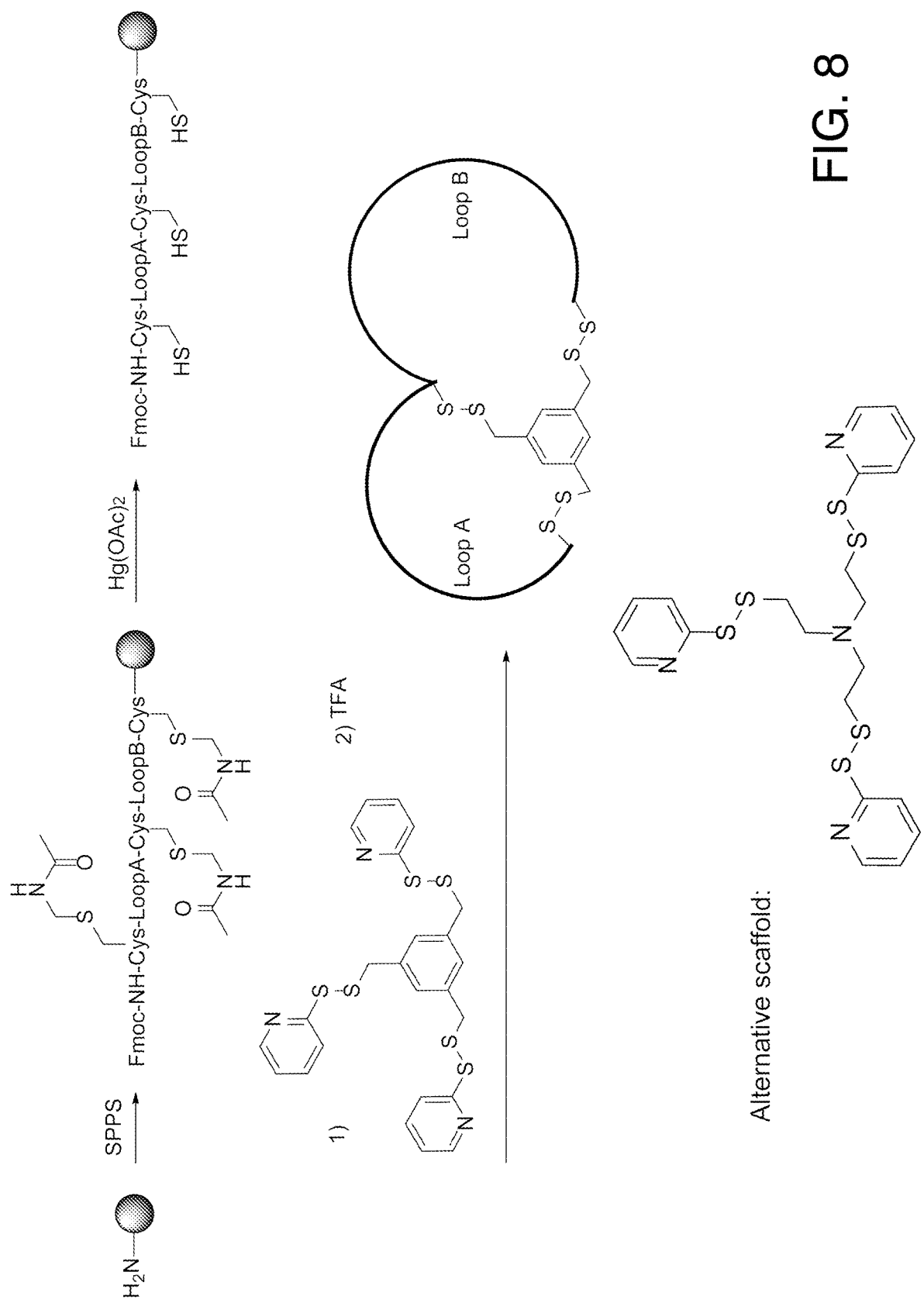
FIG. 8 is a schematic illustration of a tris-(disulfide) containing bicyclic peptide.
Figure 9:
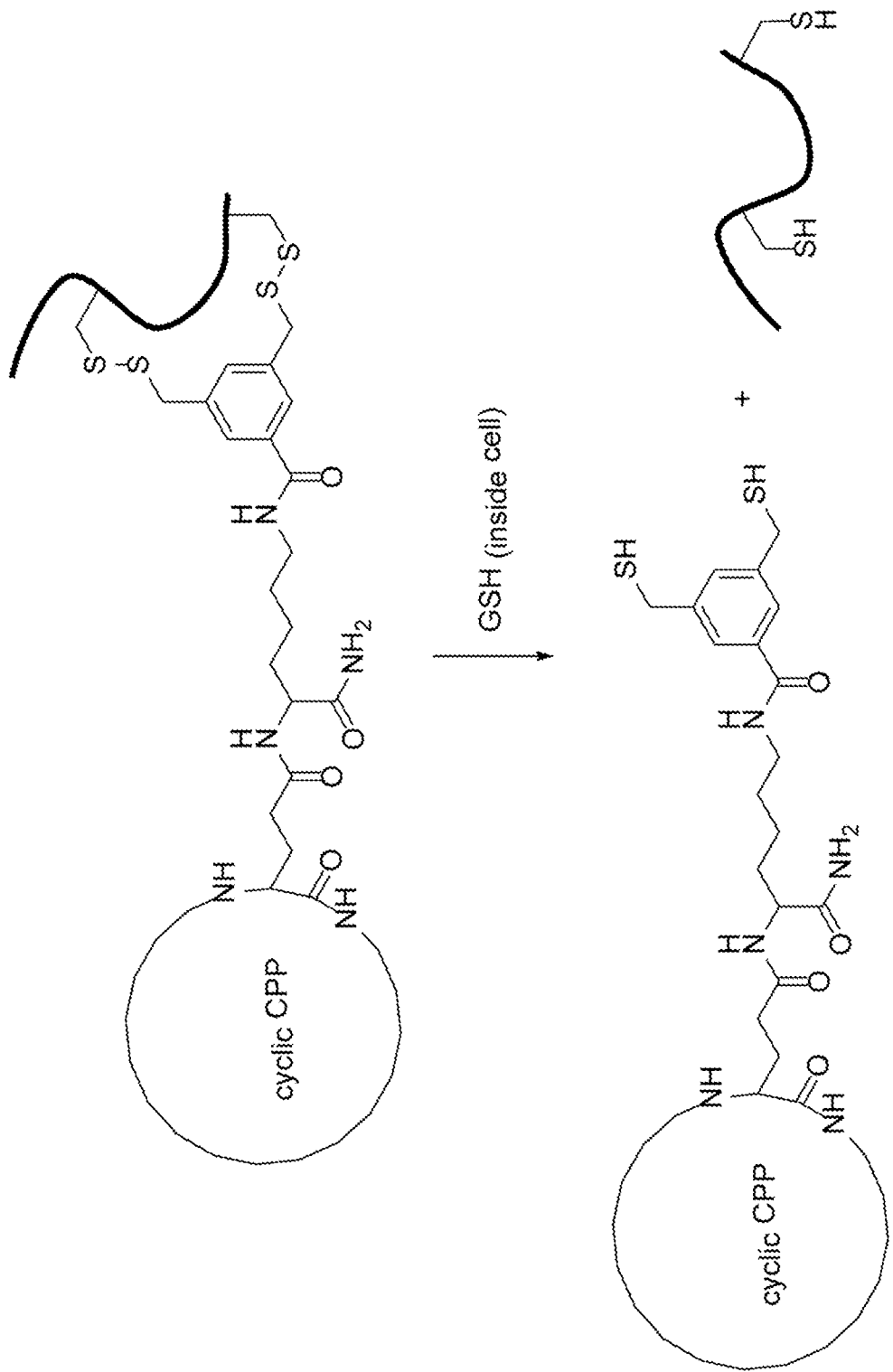
FIG. 9 is a schematic illustration of a bis-(disulfide) containing bicyclic peptide which releases the cargo from the cyclic cell-penetrating peptide upon entry into the cytosole of a cell.

FIG. 8 shows an embodiment of a tris-disulfide containing bicyclic peptide according to Formula 9-A.

In some embodiments, a compound of Formula 11 has the following formula:

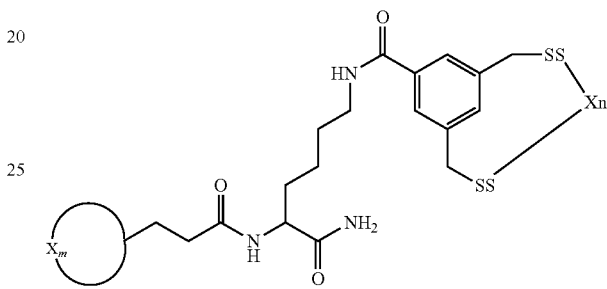

In some embodiments, a compound of Formula 12 has the following formula:

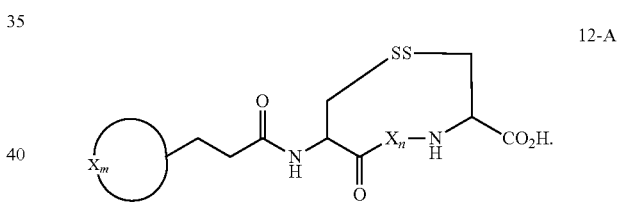

The Appendix attached herewith includes further illustrative formulae of the bicyclic peptides of the present disclosure.

In a particular aspect, disclosed herein are bicyclic peptides of Formula I.

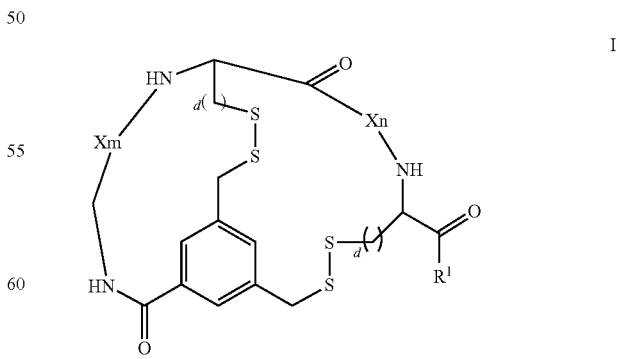

wherein R$^1$ is OH, OR$^2$, NHR$^2$, wherein R$^2$ is a C$_{1-20}$ alkyl, C$_{6-10}$ aryl or heteroaryl, amino acid residue, peptide sequence of 2 to 20 amino acid residues, detectable moiety, or solid support; and wherein each d is independently 1 or 2. The two peptide sequences $X_m$ and $X_n$ are coupled to a central 3,5-(bismercaptomethyl)benzoyl moiety, forming a bicyclic structure with a cell penetrating peptide loop of sequence $X_m$ and a cargo loop of sequence $X_n$ (see FIG. 2). As discussed above, $X_m$ and $X_n$ are used to represent peptide sequences in the bicyclic peptides described herein, and the N-terminus and C-terminus of the $X_m$ and $X_n$ may be included in various formulae provided herein (e.g., in Formula I above) to illustrate the connectivity of $X_m$ and $X_n$ in the bicyclic peptide. It is to be understood that when the terminal residues of $X_m$ and $X_n$ (e.g., —NH—, or —NH—C(O)—) are provided in a formula, such residues do not represent additional atoms that are required by the bicyclic peptide, but rather these residues are components of the amino acids contained in $X_m$ and/or $X_n$. When compounds of Formula I are in their uncyclized form, e.g., prior to forming the disulfide bridges or after entering the cell and being acted upon by GSH, they can be represented as Formula I-A.

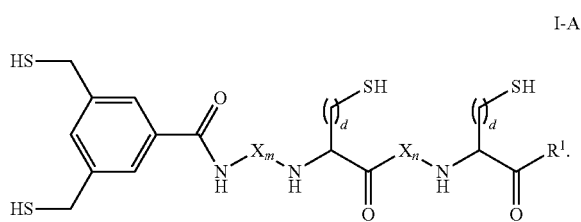

I-A

In an additional aspect, $X_m$ and $X_n$ can be coupled to the central 3,5-(bismercaptomethyl)benzoyl moiety in the opposite manner than that shown in Formula I. These compounds are also disclosed herein and are represented by Formula II.

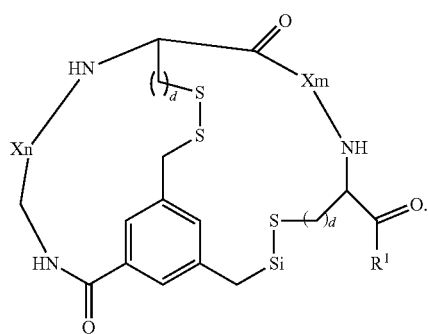

II

Also disclosed herein are peptide sequences of Formula III.

BMB-(AA$^n$)$_u$     III wherein:
u is an integer of from 4 to 20;
each AA$^n$ is, independently, a natural or non-natural amino acid residue, with at least two AA$^n$ residues independently selected from the group consisting of cysteine, homocysteine, an amino acid analog having a thiol group; and
BMB is a 3,5-bis(mercaptomethyl)benzoic acid residue.
$X_m$ and $X_n$
$X_m$ and $X_n$ can independently comprise any suitable number of amino acids which can be cyclized. In some embodiments, $X_m$ and $X_n$ can independently comprise a sequence of from 1-50 amino acid residues (e.g., 1-20 amino acids, including 1, 2, 3, 4, 5, 6, 7, 8, 9, 10, 11, 12, 13, 14, 15, 16, 18, 19, and 20, including all ranges therebetween). In some embodiments, the combined number of amino acids in $X_m$ and $X_n$ is at least 8 residues. In some examples, $X_m$ or $X_n$ can independently comprise 4 or more amino acid (e.g., 5 or more, 6 or more, 7 or more, 8 or more, or 9 or more). In some examples, $X_m$ or $X_n$ can independently comprise 20 or less amino acids (e.g., 19 or less, 18 or less, 17 or less, 16 or less, or 15 or less). In particular embodiments, $X_m$ or $X_n$ can independently comprise from 5 to 10 amino acids. Each amino acid can be a natural or non-natural amino acid, or an analog or derivative thereof. Thus, the term amino acid, when used herein, is inclusive of natural and non-natural amino acids, and analogs and derivatives thereof. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These are listed in the Table 1 along with their abbreviations used herein.

TABLE 1

Amino Acid Abbreviations

| Amino Acid | Abbreviations* L-amino acid | Abbreviations* D-amino acid |
| --- | --- | --- |
| Alanine | Ala (A) | ala (a) |
| Allosoleucine | AIle | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| glutamine | Gln(Q) | gln (q) |
| glycine | Gly (G) | gly (g) |
| histidine | His (H) | his (h) |
| Homoproline (aka pipecolic acid) | Pip (Θ) | pip (θ) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe(F) |
| phenylglycine | Phg(Ψ) | phg |
| 4-(phosphonodifluoromethyl) phenylalanine | F$_2$Pmp (Λ) | f$_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| Valine | Val (V) | val (v) |
| 2,3-diaminopropionic acid | Dap | dap |

*single letter abbreviations: when shown in capital letters herein it indicates the L-amino acid form, when shown in lower case herein it indicates the D-amino acid form As discussed above, non-natural amino acids and D-amino acids can be used herein. The disclosed methods and compositions are particularly well suited for incorporating non-natural and D-amino acids. The amino acids can be coupled by a peptide bond. Each amino acids can be coupled to an adjacent amino acid at the amino group, the carboxylate group, or the side chain.

$X_m$

The amino acid sequence $X_m$ can be a cell penetrating peptide sequence. In some embodiments, $X_m$ is from 4 to 20 (e.g., 5 to 10) amino acid residues in length. In some embodiments, at least one, at least two, or at least three amino acids in $X_m$ are arginine. In some examples, at least one, at least two, or at least three amino acids in $X_m$ have a hydrophobic side chain. Non-limiting examples of amino acids having a hydrophopbic side chain include glycine, alanine, valine, leucine, isoleucine, methionine, phenylalanine, tryptophan, proline, naphthylalanine, phenylglycine, homophenylalanine, tyrosine, cyclohexylalanine, or norleucine. In particular embodiments, the hydrophobic side chain is a hydrophobic aromatic aide chain. In some embodiments, amino acids having an aromatic hydrophobic side chain include naphthylalanine, phenylglycine, homophenylalanine, phenylalanine, tryptophan, and tyrosine. In particular embodiments, the amino acid having a hydrophobic is phenylalanine, naphthylalanine, tryptophan, or an analog or derivative thereof. In some examples, at least one amino acid in $X_m$ comprises phenylalanine, phenylglycine, or histidine, or analogs or derivatives thereof. In some examples, $X_m$ comprises at least one arginine or an analog or derivative thereof.

In some specific examples of Formula I or II, $X_m$ can independently selected from any of the sequences listed in Table 2. In some examples, the cell penetrating peptide can be the reverse of any of the sequences listed in Table 2.

TABLE 2

Example sequences for $X_m$.

| SEQ ID NO | CPP sequence |
|---|---|
| 64 | FΦRRR |
| 65 | FΦRRRC |
| 66 | FΦRRRU |
| 67 | RRRΦF |
| 68 | RRRRΦF |
| 69 | FΦRRRR |
| 70 | FφH-RrR |
| 71 | FφH-RrR |
| 72 | FΦRRRR |
| 73 | fΦRrRr |
| 74 | RRFRΦR |
| 75 | FRRRRΦ |
| 76 | rRFRΦR |
| 77 | RRΦFRR |
| 78 | CRRRRFW |
| 79 | FRΦRrRr |

TABLE 2-continued

Example sequences for $X_m$.

| SEQ ID NO | CPP sequence |
|---|---|
| 80 | FFΦRRRR |
| 81 | RFRFRΦR |
| 82 | URRRRFW |
| 83 | CRRRRFW |
| 84 | FΦRRRRQK |
| 85 | FΦRRRRQC |
| 86 | fΦRrRrR |
| 87 | FΦRRRRR |
| 88 | RRRRΦFDΩC |
| 89 | FΦRRR |
| 90 | FWRRR |
| 91 | RRRΦF |
| 92 | RRRWF |
| 93 | FΦRRRR |
| 94 | FFRRR |
| 95 | FFrRr |
| 96 | FFRrR |
| 97 | FRFRR |
| 98 | FRRFR |
| 99 | FRRRF |
| 100 | GΦRRR |
| 101 | FFFRA |
| 102 | FFFRR |
| 103 | FRRRR |
| 104 | FRRFRR |
| 105 | FRRRFR |
| 106 | RFFRRR |
| 107 | RFRRFR |
| 108 | FRFRRR |
| 109 | FFFRRR |
| 110 | FFRRRF |
| 111 | FRFFRR |
| 112 | RRFFFR |
| 113 | FFRFRR |
| 114 | FFRRFR |
| 115 | FRRFFR |
| 116 | FRRFRF |
| 117 | FRFRFR |

TABLE 2-continued

Example sequences for $X_m$.

| SEQ ID NO | CPP sequence |
|---|---|
| 118 | RFFRFR |
| 119 | GΦRRRR |
| 120 | FFFRRRR |
| 121 | RFFRRRR |
| 122 | RRFFRRR |
| 123 | RFFFRRR |
| 124 | RRFFFRR |
| 125 | FFRRFRR |
| 126 | FFRRRRF |
| 127 | FRRFFRR |
| 128 | FFFRRRRR |
| 129 | FFFRRRRRR |
| 130 | FΦRrRr |
| 131 | XXRRRR |
| 132 | PfFRrR |
| 133 | fFfrRr |
| 134 | fFfRrR |
| 135 | PfFrRr |
| 136 | fFφrRr |
| 137 | fΦfrRr |
| 138 | φFfrRr |
| 139 | FΦrRr |
| 140 | fΦrRr |
| 141 | Ac-Lys-fFRrRrD |
| 142 | Ac-Dap-fFRrRrD |
| 143 | WWWRRRR |
| 144 | WWWRRRRR |
| 145 | FWRRRR |
| 146 | WWWRRR |

Φ = L-naphthylalanine; φ = D-naphthylalanine; Ω = L-norleucine; r = D-arginine; F = L-phenylalanine; f = D-phenylalanine; q = D-glutamine; X = L-4-fluorophenylalanine; Dap =L-2,3-diaminopropionic acid.

In some examples, $X_m$ can by any of SEQ ID NO:64 to SEQ ID NO:146. In some examples, $X_m$ can be a variant of any of SEQ ID NO:64 to SEQ ID NO:146. Also disclosed herein are cyclic sequences of the peptides in Table 2. Sequences 64-146 can also be modified by having one or more cysteine residues (or other amino acid having a thiol group) internally or at one or both ends (i.e., at the C- and/or N-terminus), which allows for cyclization of the peptide by forming a disulfide bond with the cysteine (or other amino acid having a thiol group).

Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 3 and are referred to as conservative substitutions.

TABLE 3

Amino Acid Substitutions
Exemplary Conservative Substitutions

| | |
|---|---|
| Ala replaced by Ser | Leu replaced by Ile or Val |
| Arg replaced by Lys or Gln | Lys replaced by Arg or Gln |
| Asn replaced by Gln or His | Met replaced by Leu or Ile |
| Asp replaced by Glu | Phe replaced by Met, Leu, Nal, Phg, or Tyr |
| Cys replaced by Ser | Ser replaced by Thr |
| Gln replaced by Asn or Lys | Thr replaced by Ser |
| Glu replaced by Asp | Trp replaced by Tyr |
| Gly replaced by Pro | Tyr replaced by Trp or Phe |
| His replaced by Asn or Gln | Val replaced by Ile or Leu |
| Ile replaced by Leu or Val | |

Substantial changes in function are made by selecting substitutions that are less conservative than those in Table 3, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

It is understood that one way to define the variants of $X_m$ is through defining the variants in terms of homology/identity to specific known sequences. For example, SEQ ID NO:64 to SEQ ID NO:146 each sets forth a particular sequence. Specifically disclosed are variants of these peptide that have at least, 85%, 90%, 95%, 97%, or 99% homology to SEQ ID NO:64 to SEQ ID NO:146. Those of skill in the art readily understand how to determine the homology of two proteins. For example, the homology can be calculated after aligning the two sequences so that the homology is at its highest level.

In addition to variants of SEQ ID NO:64 to SEQ ID NO:146 are derivatives of these peptides which also function in the disclosed methods and compositions. Derivatives are formed by replacing one or more residues with a modified residue, where the side chain of the residue has been modified.

In particular examples, $X_m$ comprises at least one, at least two, or more specifically, at least three adjacent arginine (R or r) residues. Further, in these structures there are at least one, at least two, or at least three hydrophobic residues, for example, phenylalanine, naphthylalanine, tryptophan, or an analog or derivative thereof. For example, there can be 1 arginine and 5 hydrophobic residues like phenylalanine, naphthylalanine, tryptophan, or an analog or derivative thereof, 2 arginine and 4 hydrophobic residues like phenylalanine, naphthylalanine, tryptophan, or an analog or derivative thereof, 3 arginine and 3 hydrophobic residues like phenylalanine, naphthylalanine, tryptophan, or an analog or derivative thereof, 4 arginine and 2 hydrophobic residues like phenylalanine, naphthylalanine, tryptophan, or an analog or derivative thereof, or 4 arginine and 1 hydrophobic residue like phenylalanine, naphthylalanine, tryptophan, or an analog or derivative thereof. In a specific example, the cyclic compounds disclosed herein have 3 arginines and 3 hydrophobic residues like phenylalanine, naphthylalanine, tryptophan, or an analog or derivative thereof. Further the arginine residues can be clustered, e.g., an arginine is within 2 amino acids of another arginine residue. Likewise, the hydrophobic residues can be clustered, e.g., one hydrophobic residue is with 2 amino acids of another hydrophobic residue.

In a preferred example, $X_m$ is or comprises RRRRΦF, FΦRRRR, FfΦRrRr, fΦRrRr, fΦRrRr, FΦrRrR, or FΦrRrR.

In some embodiments, the amino acid sequence $X_m$ can be represented as or can comprise $AA^1\text{-}AA^2\text{-}AA^3\text{-}AA^4\text{-}AA^5\text{-}(AA^6)_m\text{-}(AA^7)_n\text{-}(AA^8)_p\text{-}(AA^9)_q$ wherein:

$AA^1$, $AA^2$, $AA^3$, $AA^4$, $AA^5$, $AA^6$, $AA^7$, $AA^8$, and $AA^9$ are each independently an amino acid;

at least three amino acids are arginine;

at least two amino acids comprise a hydrophobic side chain;

m, n, p, or q are independently selected from 0 and 1.

In some embodiments, $AA^1$, $AA^2$, $AA^3$, $AA^4$, $AA^5$, $AA^6$, $AA^7$, $AA^8$, and $AA^9$ corresponds to at least one amino acid sequence of SEQ ID NO:64 to SEQ ID NO:146.

Certain embodiments of the invention include amino acid sequences wherein at least four consecutive amino acids have alternating chirality. As used herein, chirality refers to the "D" and "L" isomers of amino acids. In particular embodiments of the invention, at least four consecutive amino acids have alternating chirality and the remaining amino acids are L-amino acids. In other embodiments, the peptides of the invention comprise a four amino acid sequence having D-L-D-L chirality. In still other embodiments, the peptides of the invention comprise a four amino acid sequence having L-D-L-D chirality.

In embodiments, peptides of the invention comprise two consecutive L-amino acids. In further embodiments, peptides of the invention comprise two consecutive L-amino acids separating two D-amino acids. In yet further embodiments, peptides of the invention comprise two consecutive L-amino acids separating two D-amino acids and at least four consecutive amino acids having alternating chirality, such as, but not limited to peptide sequences with D-L-L-D-L-D or L-D-L-L-D-L-D chirality. In even further embodiments, peptides of the invention comprise two consecutive L-amino acids separating two D-amino acids and at least five consecutive amino acid having alternating chirality, such as, but not limited to peptide sequences with D-L-L-D-L-D-L or L-D-L-L-D-L-D-L chirality.

In embodiments, peptides of the invention comprise two consecutive D-amino acids. In further embodiments, peptides of the invention comprise two consecutive D-amino acids separating two L-amino acids. In still further embodiments of the invention, peptides of the invention comprise two consecutive D-amino acids separating two L-amino acids and at least four consecutive amino acids having alternating chirality, such as, but not limited to peptide sequences with L-D-D-L-D-L. In even further embodiments of the invention, peptides of the invention comprise two consecutive D-amino acids separating two L-amino acids and at least five consecutive amino acids having alternating chirality, such as, but not limited to peptide sequences with L-D-D-L-D-L-D.

In some embodiments, the amino acid sequence with alternating chirality comprises about at least about 4 amino acids, at least about 5 amino acids, at least about 6 amino acids, at least about 7 amino acids, at least about 8 amino acids or at least about 9 amino acids. In embodiments, the amino acid sequence with alternating chirality comprises of from about 4 amino acids to about 9 amino acids, or about 5 amino acids to about 6 amino acids, or about 7 amino acids to about 9 amino acids, or about 8 amino acids to about 9 amino acids, or about 4 amino acids to about 8 amino acids, or about 4 amino acids to about 7 amino acids, or about 4 amino acids to about 6 amino acids, or about 4 amino acids to about 5 amino acids.

In certain embodiments, the peptides of the invention comprise at least one hydrophobic residue. In further embodiments, the peptides of the invention comprise two hydrophobic residues. In still further embodiments, the peptides of the invention comprise at least two hydrophobic residues. In certain embodiments, at least one hydrophobic residue is an aromatic hydrophobic residue. In particular embodiments, at least one hydrophobic residue is selected from the group consisting of naphthylalanine, phenylalanine, tryptophan, and tyrosine. In further embodiments, at least one hydrophobic residue is selected from the group consisting of naphthylalanine and phenylalanine. In certain embodiments, peptides of the invention comprise at least one naphthylalanine. In yet other embodiments, peptides of the invention comprise at least one phenylalanine. In still other embodiments, peptides of the invention comprise at least one phenylalanine and at least one naphthylalanine. In certain embodiments of the invention, the peptide comprises at least one hydrophobic residue in the $AA^1$, $AA^2$, or $AA^3$ position. In certain embodiments, the peptide comprises at least one aromatic hydrophobic residue in the $AA^1$, $AA^2$, or $AA^3$ position. In further embodiments of the invention, the peptide comprises at least one hydrophobic residue selected from the group consisting of naphthylalanine and phenylalanine in the $AA^1$, $AA^2$, or $AA^3$ position.

In certain aspects, disclosed herein are bicyclic peptides of Formula V, VI, VII, VIII, IX, X, and XII:

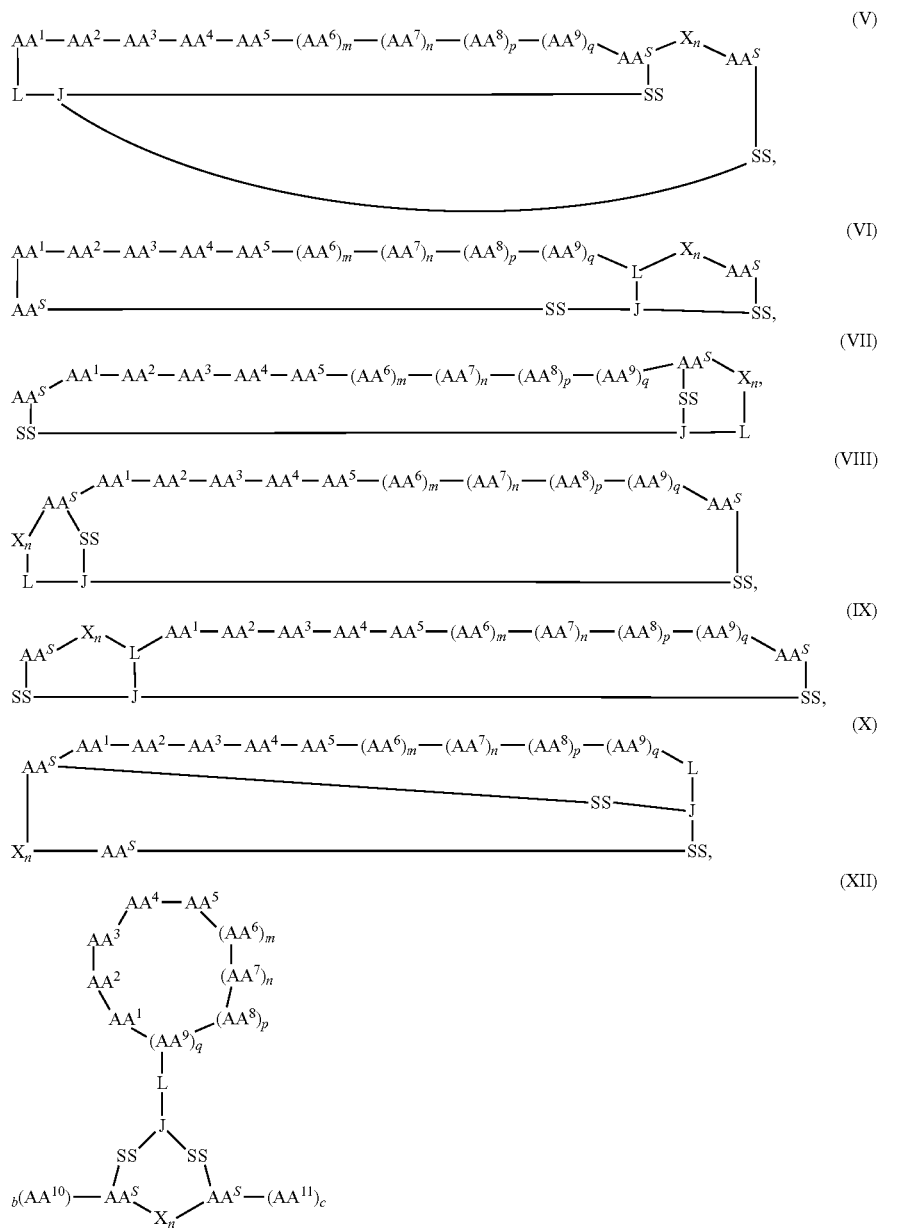

or a pharmaceutically acceptable salt thereof, wherein $AA^1$, $AA^2$, $AA^3$, $AA^4$, $AA^5$, $AA^6$, $AA^7$, $AA^9$, $AA^{10}$, and $AA^{11}$ are each independently an amino acid.

In some embodiments, at least three amino acids are arginine. In further embodiments, at least two amino acids comprise a hydrophobic residue. In some embodiments, $AA^S$ at each occurrence is independently a moiety which forms a disulfide bond with J.

In some embodiments, J is N-alkyl, aryl, or heteroaryl, each of which are independently substituted with at least two substituents which independently form a disulfide bond with $AA^S$ at each occurrence. In some embodiments J is selected from the group consisting of

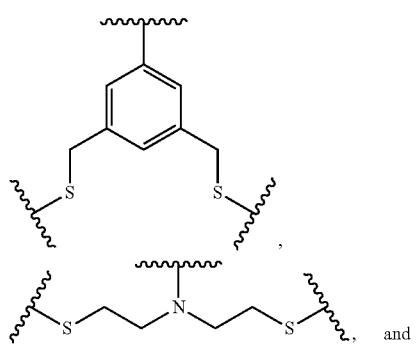

and

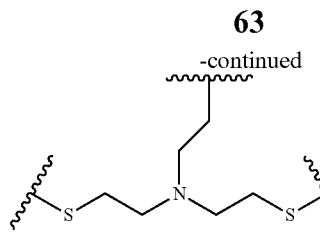
In some embodiments, L is selected from the group consisting of
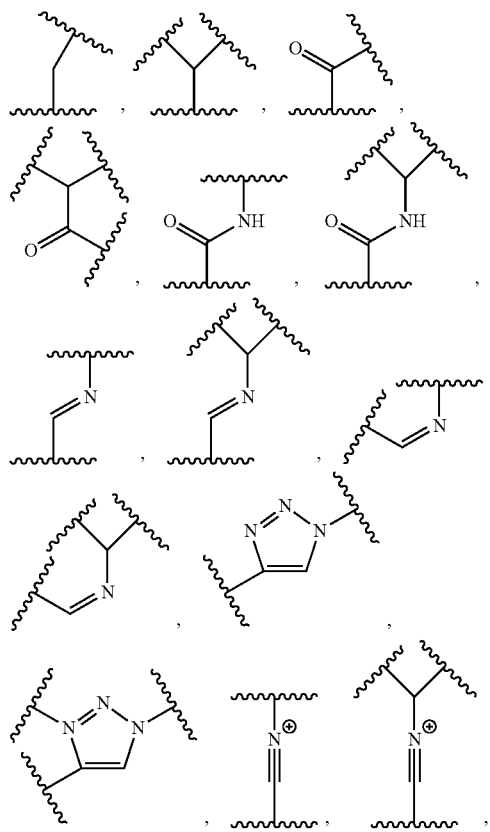
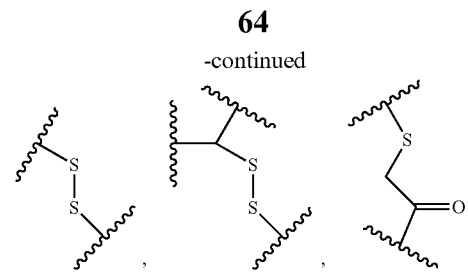
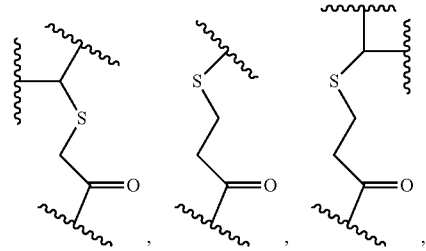
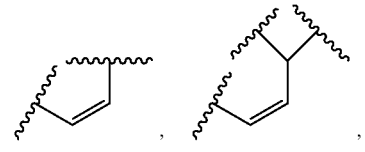
, and
In some embodiments, the compound is selected from the group consisting of:
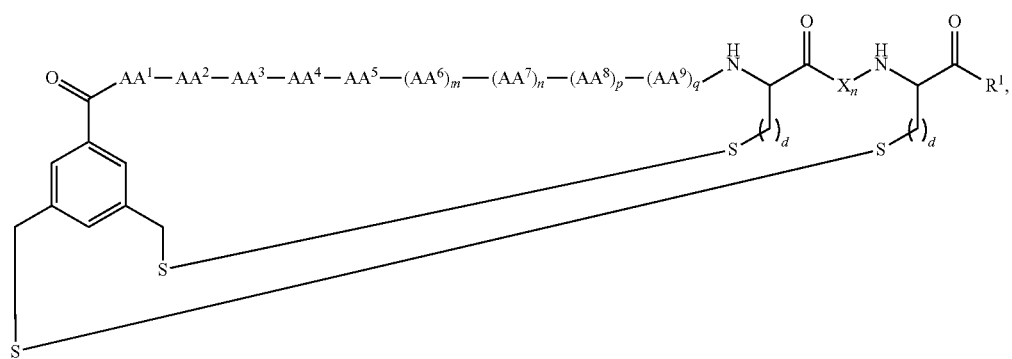

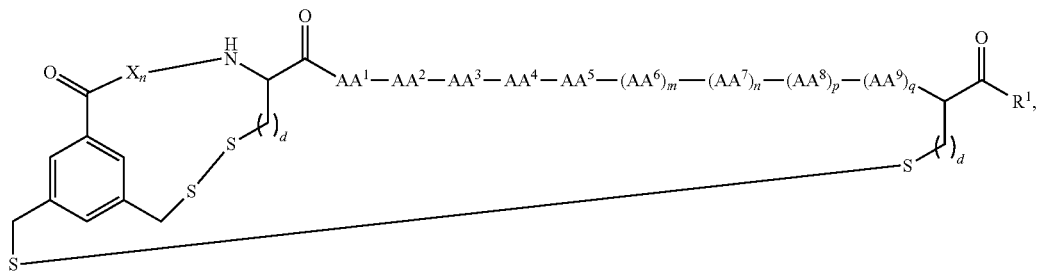
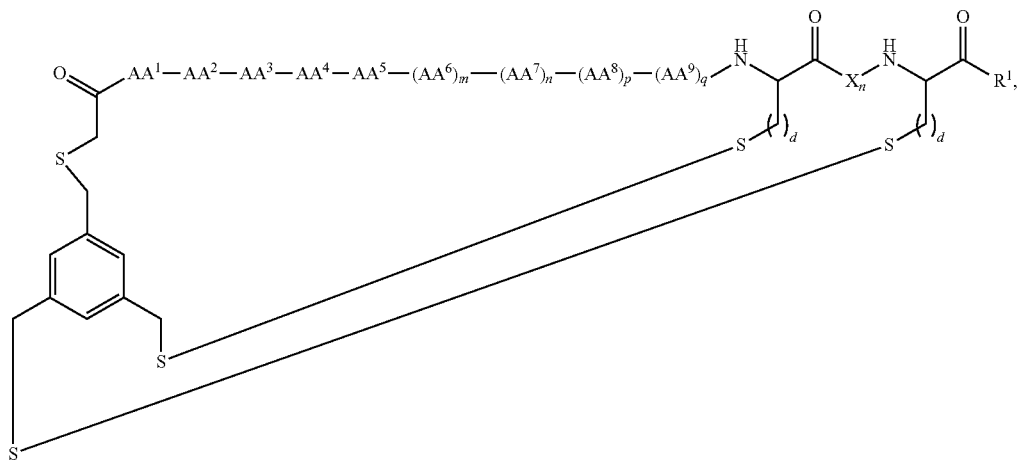
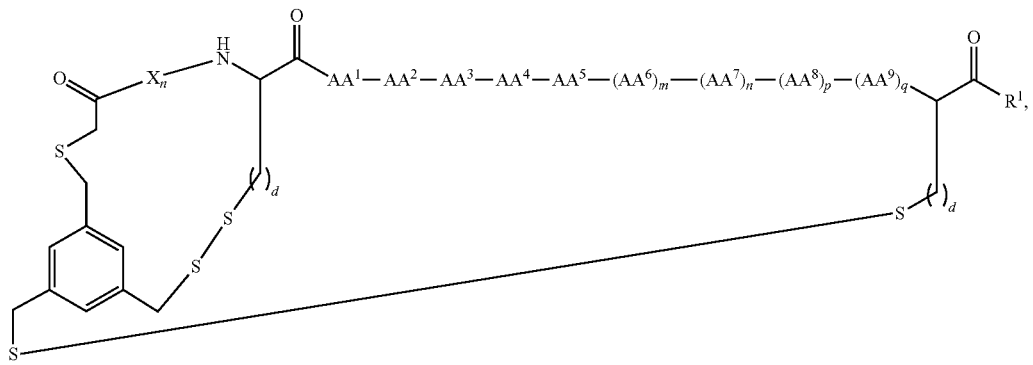
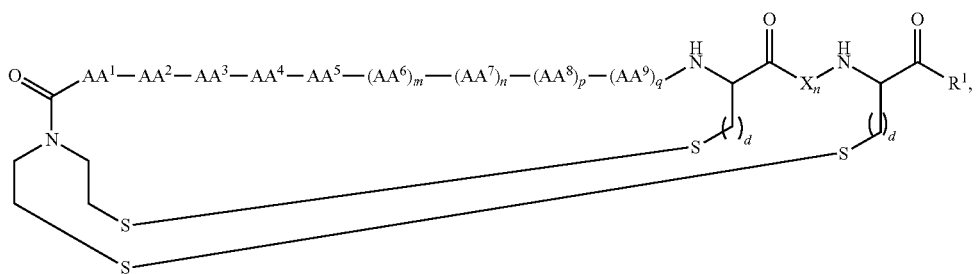
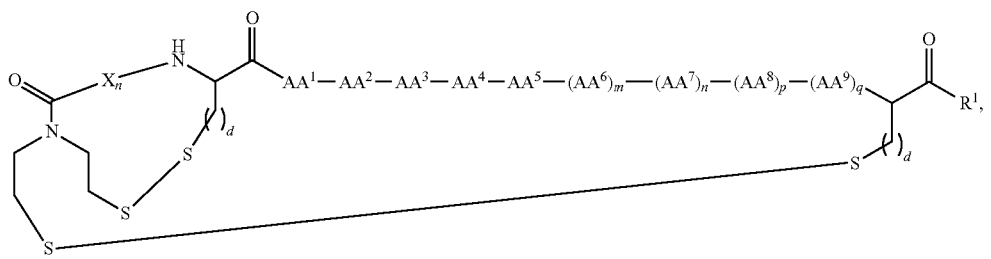

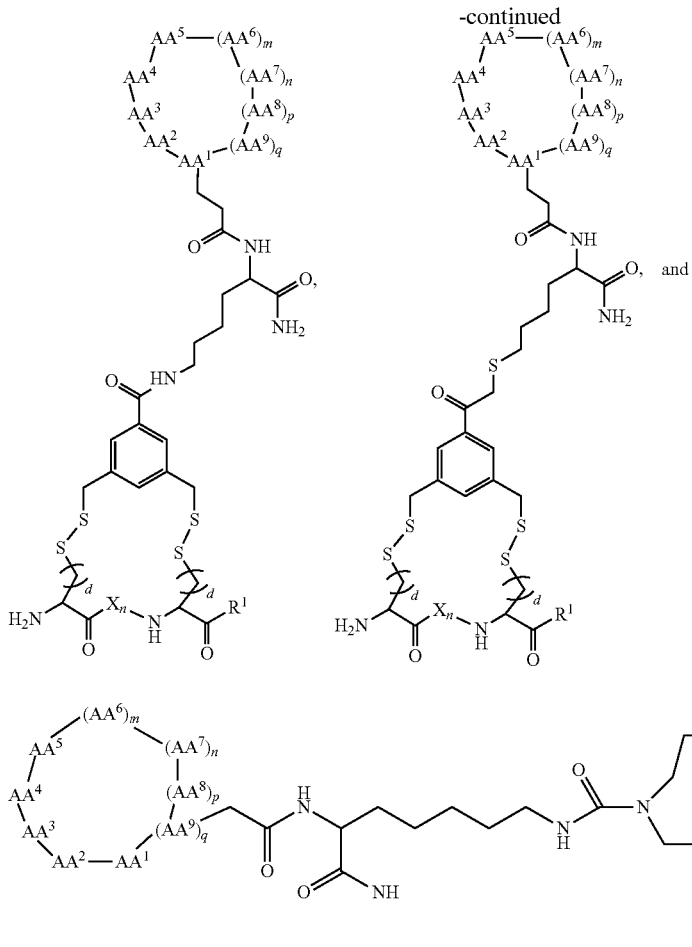

or pharmaceutically acceptable salt thereof, wherein each d is independently 1 or 2.

When compounds of Formula V, VI, VII, VIII, IX, or X are in their uncyclized form, e.g., prior to forming the disulfide bridges or after entering the cell and being acted upon by GSH, they can be represented as Formula I-A. Also disclosed are compounds according to Formula V-A, VI-A, VII-A, VIII-A, IX-A, and X-A:

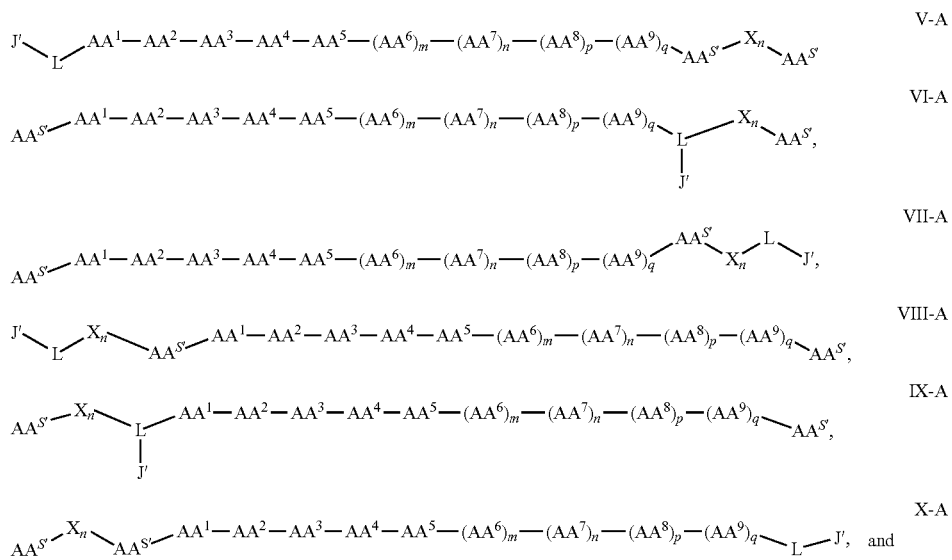

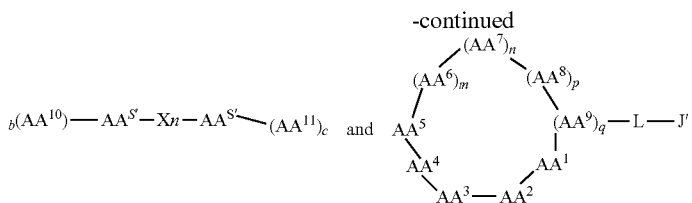

XII-A and XII-B or a pharmaceutically acceptable salt thereof,
wherein:
 $AA^{St}$ at each occurrence is independently a moiety which comprises a thiol;
 J' is an alkyl, N-alkyl, alkenyl, alkynyl, carbocyclyl, or heterocyclyl, each of which are independently substituted with at least two thiol substituents; and
 $X_n$ and L are defined herein.

In some embodiments, J is N-alkyl or aryl. In some embodiments, J' is

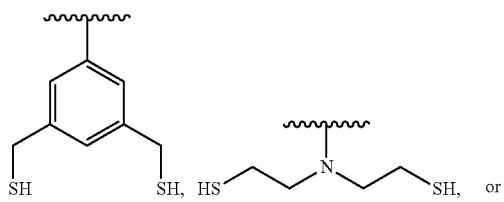

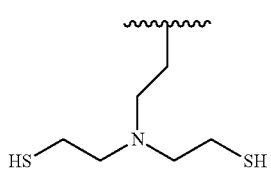

In some embodiments, each $AA^S$ is independently:

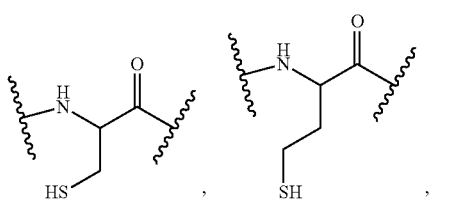

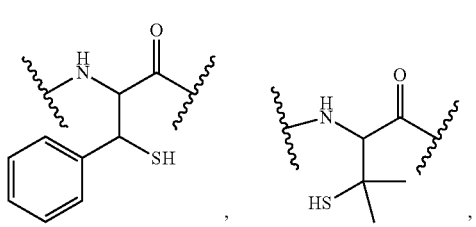

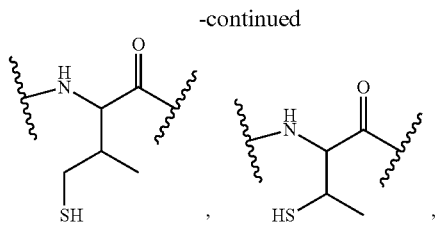

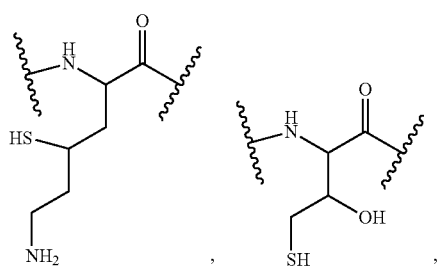

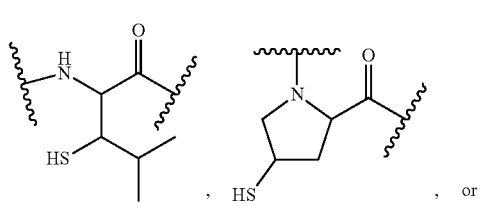

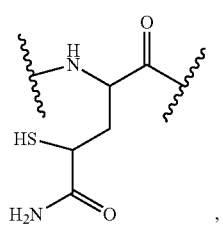

wherein the C-terminus of $AA^{St}$ forms an amide bond or is $R^1$, wherein $R^1$ is OH, $OR^2$, $NHR^2$; and wherein $R^2$ is a alkyl, aryl, heteroaryl, amino acid, peptide sequence of 2 to 20 amino acid, detectable moiety, or solid support.

In some embodiments, the compound has a structure selected from the group consisting of:
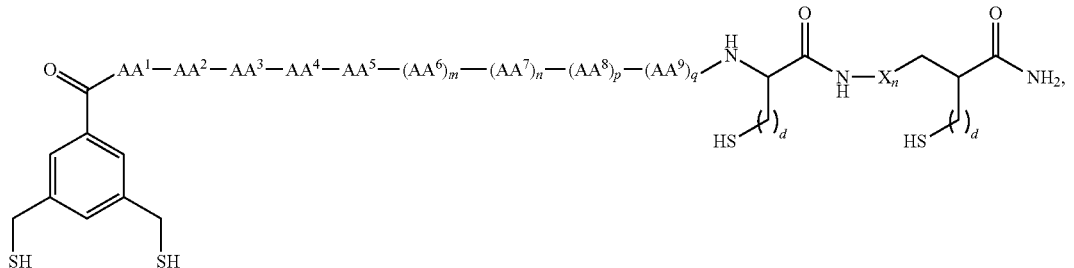
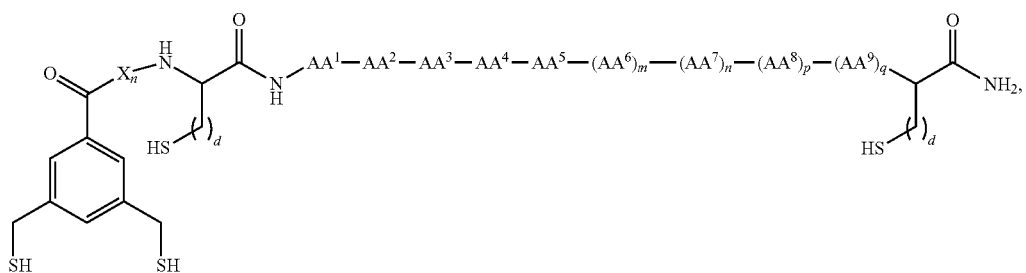
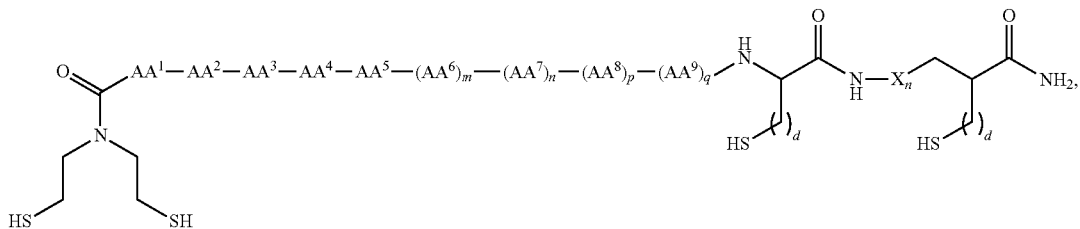
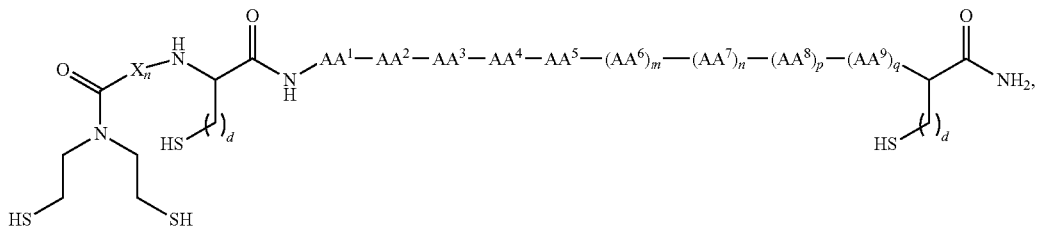
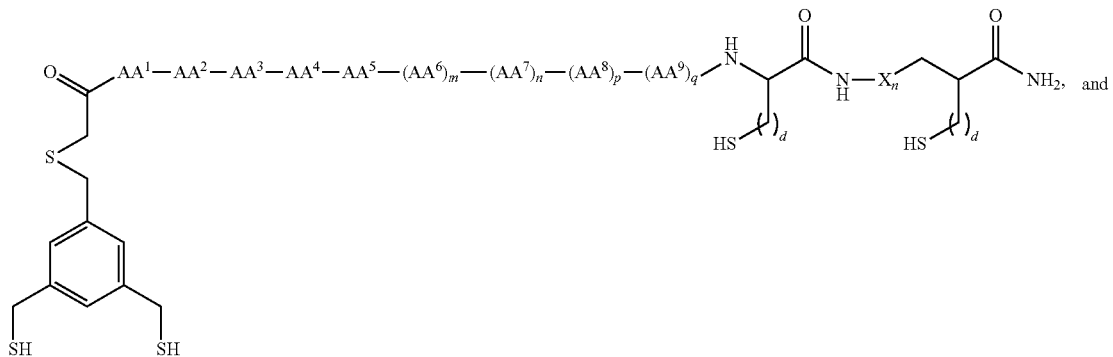

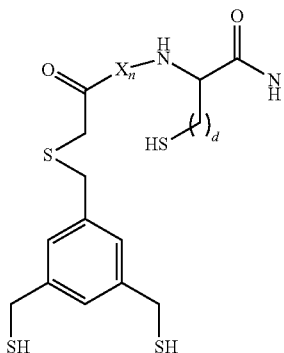

or a pharmaceutically acceptable salt thereof.

$X_n$

The amino acid sequence $X_n$ is a cargo peptide sequence. As discussed above, there is no limitation on the number of amino acids $X_n$. In some embodiments, $X_n$ may have from 1 to 50 amino acids, e.g., from 1 to 20, from 1 to 10, from 4 to 20, from 4 to 10, and all values and subranges therein. Examples of sequences for $X_n$ are those outlined above in Table 2 including variants or derivatives thereof. Additional examples of cargo peptide sequences can comprise any of those listed in Table 4 or Table 5, or derivatives or combinations thereof.

TABLE 4

Example Cargo Sequences

| SEQ ID NO | Sequence |
|---|---|
| 1 | HKGFY |
| 2 | AFWTG |
| 3 | HALΩ |
| 4 | ΨYAKYFGKH-Dap |
| 5 | AFVVTEKΩLAH-Dap |
| 6 | F-Dap-SVPYH-Dap |
| 7 | WFDKFNH-Dap |
| 8 | dΦ-SQ-dΦ-KFRVR-Dap |
| 9 | RRdΦ-R-fF-KFQG-Dap |
| 10 | OR-dΦ-R-fF-KFQG-Dap |
| 11 | RFZZFK |
| 12 | RDΨZNK |
| 13 | ZZPGAK |
| 14 | ZZASAK |
| 15 | ZZLPTK |
| 16 | ΨRNZIK |
| 17 | ZTEANK |
| 18 | Z-dΦ-VGQK |
| 19 | ZΨSZZK |
| 20 | ZΨMSZK |

TABLE 4-continued

Example Cargo Sequences

| SEQ ID NO | Sequence |
|---|---|
| 21 | ZSMZGK |
| 22 | ZSΨZZK |
| 23 | ZRVDAK |
| 24 | RDΨPra-N |
| 25 | ΦRRRR-Dap |
| 26 | ΨRN-Pra-I |
| 27 | Pra-SΨKK |
| 28 | Pra-RVDA |
| 29 | AΨRN-Pra-I |
| 30 | ΨRN-Pra-IA |
| 31 | AΨRN-Pra-IA |
| 32 | AAΨRN-Pra-IA |
| 33 | AFΨRN-Pra-I-A |
| 34 | A-AbuΨRN-Pra-I-Abu |
| 35 | ΨIΨRN-Pra-I-Abu-K |
| 36 | ΨΨRN-Pra-I-Abu |
| 37 | ALΨRN-Pra-ID |
| 38 | AQΨRN-Pra-ID |
| 39 | IEΨRN-Pra-ID |
| 40 | ASΨRN-Pra-IE |
| 41 | LΨRN-Pra-IE |
| 42 | AΨΨRN-Pra-IF |
| 43 | A-OrnΨRN-Pra-IF |
| 44 | A-AbuΨRN-Pra-IN |
| 45 | dA-AΨRN-Pra-IN |
| 46 | ΨNΨRN-Pra-II |
| 47 | A-AbuΨRN-Pra-I-Nle |

TABLE 4-continued

Example Cargo Sequences

| SEQ ID NO | Sequence |
|---|---|
| 48 | WΨRN-Pra-IΨ |
| 49 | ANΨRN-Pra-IR |
| 50 | R-ΩΨRN-Pra-IS |
| 51 | HΨRN-Pra-IYK-Φ |
| 52 | A-AbuΨRN-Pra-I-Abu |
| 53 | ΨIΨRN-Pra-I-Abu |
| 54 | ALΨRN-Pra-ID |
| 55 | AQΨRN-Pra-ID |
| 56 | A-OrnΨRN-Pra-IF |
| 57 | AΨΨRN-Pra-IF |
| 58 | A-AbuΨRN-Pra-I-Abu |
| 59 | AAΨRN-Pra-IA |
| 60 | AAFRN-Pra-IA |
| 61 | ALFRN-Pra-ID |
| 62 | ΨYAKYFGKH |
| 63 | AFWTEKΩLAH |

TABLE 5

Example cargo moieties

| SEQ ID NO | Abbreviation | Sequence* |
|---|---|---|
| 147 | R$_5$ | RRRRR |
| 148 | A$_5$ | AAAAA |
| 149 | F$_4$ | FFFF |
| 150 | PCP | DE(pCAP)LI |
| 151 | A$_7$ | AAAAAAA |
| 152 | | RARAR |
| 153 | | DADAD |
| 154 | | DΩUD |
| 155 | | UTRV |
| 156 | | SASAS |
| 157 | | ALDWSWLQ |
| 158 | | ALDASALQ |
| 159 | | SFAEYWALLS |

*pCAP, phosphocoumaryl amino propionic acid; Ω, norleucine; U, 2-aminobutyric acid.

It should be understood that when referring to Formula I, the sequence $X_n$ is coupled to a cysteine residue (C) at each end, and the amide bonds formed by said coupling are included in Formula I. Likewise, when referring to Formula II, $X_m$ is coupled to a cysteine residue at each end, and the amide bonds formed by said coupling are included in Formula II. For example, these sections can be represented as —C—$X_n$—C— or —C—$X_m$—C—, or sometimes as —C-(AA)$_n$-C—, where AA=an amino acid residue as defined herein and n is an integer of from 2 to 8, e.g., —C-AA$^1$-AA$^2$-C—, —C-AA$^1$-AA$^2$-AA$^3$-C—, —C-AA$^1$-AA$^2$-AA$^3$-AA$^4$-C—, —C-AA$^1$-AA$^2$-AA$^3$-AA$^4$-AA$^5$-C—, —C-AA$^1$-AA$^2$-AA$^3$-AA$^5$-AA$^6$-C—, —C-AA$^1$-AA$^2$-AA$^3$-AA$^5$-AA$^6$-AA$^7$-C—, and —C-AA$^1$-AA$^2$-AA$^3$-AA$^5$-AA$^6$-AA$^1$-AA$^8$-C—. When referring to Formula I, the two terminal cysteine residues attached to sequence $X_n$ are coupled to the 3,5-(bismercaptomethylbenzoyl) moeity of Formula I and one cysteine residue is also coupled to sequence $X_m$ (which is also coupled to the 3,5-(bismercaptomethylbenzoyl) moiety of Formula I). When referring to Formula II, the two terminal cysteine residues attached to sequence $X_m$ are coupled to the 3,5-(bismercaptomethylbenzoyl) moiety of Formula II and one cyctein residue is also coupled to sequence $X_n$ (which is also coupled to the 3,5-(bismercaptomethylbenzoyl) moiety of Formula II).

Specific Examples

Specific examples of bicyclic peptides disclosed herein are shown in Table 6.

TABLE 6

Sequences of peptides in this work$^a$

| Peptide | SEQ ID NO$^b$ | Sequence |
|---|---|---|
| 1 | 160 | RQIKIWFQNRRMKWKKGG-TALDWSWLQTE |
| 2 | 161 | BMB-RRRRΦF-C-SASAS-C-K 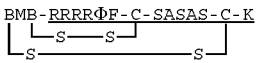 |
| 3 | 162 | BMB-SASAS-C-FΦRRRR-C-K 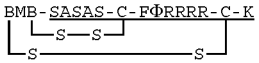 |
| 4 | 163 | BMB-RRRRΦF-C-ALDWSWLQ-C 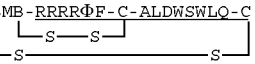 |
| 5 | 164 | BMB-RRRRΦF-C-ALDASALQ-C 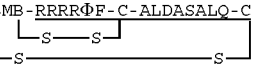 |
| 6 | 165 | MP-RRRRΦF-C-ALDWSWLQ 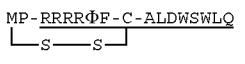 |
| 7 | 166 | BMB-RRRRΦF-C-SFAEYWALLS-C 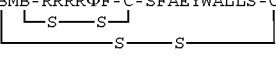 |
| 8 | 167 | BMB-SFAEYWALLS-C-RRRRΦF-C 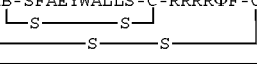 |

$^a$BMB, 3,5-bis(mercaptomethyl)benzoyl; Φ, L-2-naphthylalanine; MP, 3-mercaptopropionyl.
$^b$underlined portion only.

Detectable Moiety

The disclosed compounds can also comprise a detectable moiety, e.g., linked to a side chain of any amino acid in $X_m$ or $X_n$ or on $R^1$. The detectable moiety can comprise any detectable label. Examples of suitable detectable labels include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiments, the label is detectable without the addition of further reagents.

In some embodiments, the detectable moiety is a biocompatible detectable moiety, such that the compounds can be suitable for use in a variety of biological applications. "Biocompatible" and "biologically compatible", as used herein, generally refer to compounds that are, along with any metabolites or degradation products thereof, generally non-toxic to cells and tissues, and which do not cause any significant adverse effects to cells and tissues when cells and tissues are incubated (e.g., cultured) in their presence.

The detectable moiety can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru (dpp)$_3$); Ru (II) tris (1,10-phenanthroline) (Ru(phen)$_3$), tris(2,2'-bipyridine)ruthenium (II) chloride hexahydrate (Ru(bpy)$_3$); erythrosine B; fluorescein; fluorescein isothiocyanate (FITC); eosin; iridium (III) ((N-methyl-benzimidazol-2-yl)-7-(diethyl-amino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitirophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxyfluorecsein; carboxynaphthofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; dioctadecylcycloxacarbocyanine; fluorenylmethyloxycarbonyl chloride; 7-amino-4-methylcourmarin (Amc); green fluorescent protein (GFP); and derivatives or combinations thereof.

In some examples, the detectable moiety can comprise Rhodamine B (Rho), fluorescein isothiocyanate (FITC), 7-amino-4-methylcourmarin (Amc), green fluorescent protein (GFP), or derivatives or combinations thereof.

The detectible moiety can be attached to the cell penetrating peptide moiety at the amino group, the carboxylate group, or the side chain of any of the amino acids of the cell penetrating peptide moiety or cargo moiety (e.g., at the amino group, the carboxylate group, or the side chain or any of $X_m$ or $X_n$ or $R^1$).

Therapeutic Moiety

The disclosed compounds can also comprise a therapeutic moiety. In some examples, the cargo moiety comprises a therapeutic moiety. The detectable moiety can be linked to a therapeutic moiety or the detectable moiety can also serve as the therapeutic moiety. Therapeutic moiety refers to a group that when administered to a subject will reduce one or more symptoms of a disease or disorder.

The therapeutic moiety can comprise a wide variety of drugs, including antagonists, for example enzyme inhibitors, and agonists, for example a transcription factor which results in an increase in the expression of a desirable gene product (although as will be appreciated by those in the art, antagonistic transcription factors can also be used), are all included. In addition, therapeutic moiety includes those agents capable of direct toxicity and/or capable of inducing toxicity towards healthy and/or unhealthy cells in the body. Also, the therapeutic moiety can be capable of inducing and/or priming the immune system against potential pathogens.

The therapeutic moiety can, for example, comprise an anticancer agent, antiviral agent, antimicrobial agent, anti-inflammatory agent, immunosuppressive agent, anesthetics, or any combination thereof.

The therapeutic moiety can comprise an anticancer agent. Example anticancer agents include 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The therapeutic moiety can also comprise a biopharmaceutical such as, for example, an antibody.

In some examples, the therapeutic moiety can comprise an antiviral agent, such as ganciclovir, azidothymidine (AZT), lamivudine (3TC), etc.

In some examples, the therapeutic moiety can comprise an antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

In some examples, the therapeutic moiety can comprise an anti-inflammatory agent.

In some examples, the therapeutic moiety can comprise dexamethasone (Dex).

In other examples, the therapeutic moiety comprises a therapeutic protein. For example, some people have defects in certain enzymes (e.g., lysosomal storage disease). It is disclosed herein to deliver such enzymes/proteins to human cells by linking to the enzyme/protein to one of the disclosed cell penetrating peptides. The disclosed cell penetrating peptides have been tested with proteins (e.g., GFP, PTP1B, actin, calmodulin, troponin C) and shown to work.

Targeting Moieties

The disclosed compounds can also comprise a targeting moiety. In some examples, the cargo moiety comprises a targeting moiety. The targeting moiety can comprise, for example, a sequence of amino acids that can target one or more enzyme domains. In some examples, the targeting moiety can comprise an inhibitor against an enzyme that can play a role in a disease, such as cancer, cystic fibrosis, diabetes, obesity, or combinations thereof. For example, the targeting moiety can comprise any of the sequences listed in Table 7.

TABLE 7

Example targeting moieties

| SEQ ID NO | Abbreviation* | Sequence |
|---|---|---|
| 168 | PΘGΛYR | Pro-Pip-Gly-F$_2$Pmp-Tyr- |
| 169 | SΘIΛΛR | Ser-Pip-Ile-F$_2$Pmp-F$_2$Pmp- |
| 170 | IHIΛIR | Ile-His-Ile-F$_2$Pmp-Ile- |
| 171 | AaIΛΘR | Ala-(D-Ala)-Ile-F$_2$Pmp-Pip- |
| 172 | ΣSΘΛvR | Fpa-Ser-Pip-F$_2$Pmp-(D-Val)- |
| 173 | ΘnPΛAR | Pip-(D-Asn)-Pro-F$_2$Pmp-Ala- |
| 174 | TΨAΛGR | Tyr-Phg-Ala-F$_2$Pmp-Gly- |
| 175 | AHIΛaR | Ala-His-Ile-F$_2$Pmp-(D-Ala)- |
| 176 | GnGΛpR | Gly-(D-Asn)-Gly-F$_2$Pmp-(D-Pro)- |
| 177 | fQΘΛIR | (D-Phe)-Gln-Pip-F$_2$Pmp-Ile- |
| 178 | SPGΛHR | Ser-Pro-Gly-F$_2$Pmp-His- |
| 179 | ΘYIΛHR | Pip-Tyr-Ile-F$_2$Pmp-His- |
| 180 | SvPΛHR | Ser-(D-Val)-Pro-F$_2$Pmp-His- |
| 181 | AIPΛnR | Ala-Ile-Pro-F$_2$Pmp-(D-Asn)- |
| 182 | ΣSIΛQF | Fpa-Ser-Ile-F$_2$Pmp-Gln- |
| 183 | AaΨΛfR | Ala-(D-Ala)-Phg-F$_2$Pmp-(D-Phe)- |
| 184 | ntΨΛΨR | (D-Asn)-(D-Thr)-Phg-F$_2$Pmp-Phg- |
| 185 | IPΨΛΩR | Ile-Pro-Phg-F$_2$Pmp-Nle- |
| 186 | QΘΣΛΘR | Gln-Pip-Fpa-F$_2$Pmp-Pip- |
| 187 | nAΣΛGR | (D-Asn)-Ala-Fpa-F$_2$Pmp-Gly- |
| 188 | ntYΛAR | (D-Asn)-(D-Thr)-Tyr-F$_2$Pmp-Ala- |
| 189 | eAΨΛvR | (D-Glu)-Ala-Phg-F$_2$Pmp-(D-Val)- |

TABLE 7-continued

Example targeting moieties

| SEQ ID NO | Abbreviation* | Sequence |
|---|---|---|
| 190 | IvΨΛAR | Ile-(D-Val)-Phg-F$_2$Pmp-Ala- |
| 191 | YtΨΛAR | Tyr-(D-Thr)-Phg-F$_2$Pmp-Ala- |
| 192 | nΘΨΛIR | (D-Asn)-Pip-Phg-F$_2$Pmp-Ile- |
| 193 | ΘnWΛHR | Pip-(D-Asn)-Trp-F$_2$Pmp-His- |
| 194 | YΘvΛIR | Tyr-Pip-(D-Val)-F$_2$Pmp-Ile- |
| 195 | nSAΛGR | (D-Asn)-Ser-(D-Ala)-F$_2$Pmp-Gly- |
| 196 | tnvΛaR | (D-Thr)-(D-Asn)-(D-Val)-F$_2$Pmp-(D-Ala)- |
| 197 | ntvΛtR | (D-Asn)-(D-Thr)-(D-Val)-F$_2$Pmp-(D-Thr)- |
| 198 | SItΛYR | Ser-Ile-(D-Thr)-F$_2$Pmp-Tyr- |
| 199 | nΣnΛIR | (D-Asn)-Fpa-(D-Asn)-F$_2$Pmp-(D-Leu)- |
| 200 | YnnΛΩR | Tyr-(D-Asn)-(D-Asn)-F$_2$Pmp-Nle- |
| 201 | nYnΛGR | (D-Asn)-Tyr-(D-Asn)-F$_2$Pmp-Gly- |
| 202 | AWnΛAR | Ala-Trp-(D-Asn)-F$_2$Pmp-Ala- |
| 203 | vtHΛYR | (D-Val)-(D-Thr)-His-F$_2$Pmp-Tyr- |
| 204 | PΨHΛΘR | Pro-Phg-His-F$_2$Pmp-Pip- |
| 205 | nΨHΛGR | (D-Asn)-Phg-His-F$_2$Pmp-Gly- |
| 206 | PAHΛGR | Pro-Ala-His-F$_2$Pmp-Gly- |
| 207 | AYHΛIR | Ala-Tyr-His-F$_2$Pmp-Ile- |
| 208 | nΘeAYR | (D-Asn)-Pip-(D-Glu)-F$_2$Pmp-Tyr- |
| 209 | vSSΛtR | (D-Val)-Ser-Ser-F$_2$Pmp-(D-Thr)- |
| 210 | aΞt'ϑΦ'YNK | ((D-Ala)-Sar-(D-pThr)-Pp-Nal-Tyr-Gln)-Lys |
| 211 | Tm(aΞt'ϑΦ'RA)Dap | Tm((D-Ala)-Sar-(D-pThr)-Pp-Nal-Arg-Ala)-Dap |
| 212 | Tm(aΞt'Φ'RAa)Dap | Tm((D-Ala)-Sar-(D-pThr)-Pp-Nal-Arg-Ala-(D-Ala))-Dap |
| 213 | Tm(aΞtϑΦ'RAa)Dap | Tm((D-Ala)-Sar-(D-Thr)-Pp-Nal-Arg-Ala-(D-Ala))-Dap |
| 214 | Tm(aΞtaΦ'RAa)Dap | Tm((D-Ala)-Sar-(D-Thr)-(D-Ala)-Nal-Arg-Ala-(D-Ala))-Dap |

*Fpa, Σ =L-4-fluorophenylalanine; Pip, Θ =L-homoproline; Nle, Ω =L-norleucine; Phg, Ψ L-phenylglycine; F$_2$Pmp, Λ =L-4-(phosphonodifluoromethyl)phenylalanine; Dap =L-2,3-diaminopropionic acid; Nal, Φ' = L-β-naphthylalanine; Pp, ϑ =L-pipecolic acid; Sar, Ξ = sarcosine; Tm =trimesic acid.

In some examples, the targeting moiety can by any of SEQ ID NO:168 to SEQ ID NO:214. In some examples, the targeting moiety can be a variant of any of SEQ ID NO:168 to SEQ ID NO:214.

The targeting moiety and cell penetrating peptide moiety can overlap, that is residues that form the cell penetrating peptide moiety can also be part of the sequence that forms the targeting moiety, and vice a versa.

The therapeutic moiety can be attached to the cell penetrating peptide moiety at the amino group, the carboxylate group, or the side chain of any of the amino acids of the cell penetrating peptide moiety or cargo moiety (e.g., at the amino group, the carboxylate group, or the side chain or any of $X_m$, $X_n$ or $R^1$). In some examples, the therapeutic moiety can be attached to the detectable moiety.

In some examples, the therapeutic moiety can comprise a targeting moiety that can act as an inhibitor against Ras (e.g., K-Ras), PTP1B, Pin1, Grb2 SH2, CAL PDZ, and the like, or combinations thereof.

Ras is a protein that in humans is encoded by the RAS gene. The normal Ras protein performs an essential function in normal tissue signaling, and the mutation of a Ras gene is implicated in the development of many cancers. Ras can act as a molecular on/off switch, once it is turned on Ras recruits and activates proteins necessary for the propagation of growth factor and other receptors' signal. Mutated forms of Ras have been implicated in various cancers, including lung cancer, colon cancer, pancreatic cancer, and various leukemias.

Protein-tyrosine phosphatase 1B (PTP1B) is a prototypical member of the PTP superfamily and plays numerous roles during eukaryotic cell signaling. PTP1B is a negative regulator of the insulin signaling pathway, and is considered a promising potential therapeutic target, in particular for the treatment of type II diabetes. PIP1B has also been implicated in the development of breast cancer.

Pin1 is an enzyme that binds to a subset of proteins and plays a role as a post phosphorylation control in regulating protein function. Pin1 activity can regulate the outcome of proline-directed kinase signaling and consequently can regulate cell proliferation and cell survival. Deregulation of Pin1 can play a role in various diseases. The up-regulation of Pin1 may be implicated in certain cancers, and the down-regulation of Pin1 may be implicated in Alzheimer's disease. Inhibitors of Pin1 can have therapeutic implications for cancer and immune disorders.

Grb2 is an adaptor protein involved in signal transduction and cell communication. The Grb2 protein contains one SH2 domain, which can bind tyrosine phosphorylated sequences. Grb2 is widely expressed and is essential for multiple cellular functions. Inhibition of Grb2 function can impair developmental processes and can block transformation and proliferation of various cell types.

It was recently reported that the activity of cystic fibrosis membrane conductance regulator (CFTR), a chloride ion channel protein mutated in cystic fibrosis (CF) patients, is negatively regulated by CFTR-associated ligand (CAL) through its PDZ domain (CAL-PDZ) (Wolde, M et al. *J. Biol. Chem.* 2007, 282, 8099). Inhibition of the CFTR/CAL-PDZ interaction was shown to improve the activity of ΔPhe508-CFTR, the most common form of CFTR mutation (Cheng, S H et al. *Cell* 1990, 63, 827; Kerem, B S et al. *Science* 1989, 245, 1073), by reducing its proteasome-mediated degradation (Cushing, P R et al. *Angew. Chem. Int. Ed.* 2010, 49, 9907). Thus, disclosed herein is a method for treating a subject having cystic fibrosis by administering an effective amount of a compound or composition disclosed herein. The compound or composition administered to the subject can comprise a therapeutic moiety that can comprise a targeting moiety that can act as an inhibitor against CAL PDZ. Also, the decompositions or compositions disclosed herein can be administered with a molecule that corrects the CFTR function.

In some examples the targeting moiety can comprise E-T-G-E-F-L (SEQ ID NO:215) or LDPETGE (SEQ ID NO:216).

Linking Moiety

The disclosure provides for a compound according to Formula IV':

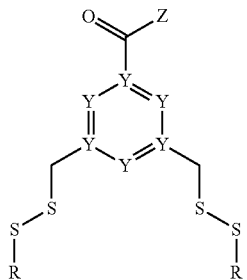

IV' wherein:
each Y is independently CH or N, provided no more than four Y are N;
Z is OR$_a$, hydrogen, halogen, carbocyclyl, herterocyclyl, or an amino acid;
each R is independently an alkyl, alkenyl, alkynyl, carbocyclyl, heterocyclyl, or an amino acid; and
R$_a$ is independently H, C(O)alkyl, alkyl, alkenyl, alkynyl, carbocyclic, or heterocyclyl.

In embodiments, the compound of Formula IV has a structure according to Formula IV'a:

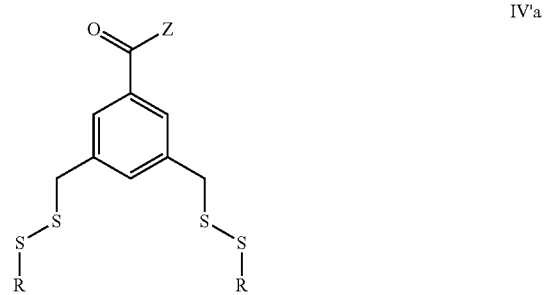

IV'a

In some embodiments, wherein Z is OH. In some embodiments, R is independently aryl or hetereoaryl.

In some embodiments, the compound of Formula IV has a structure according to Formula IV'b

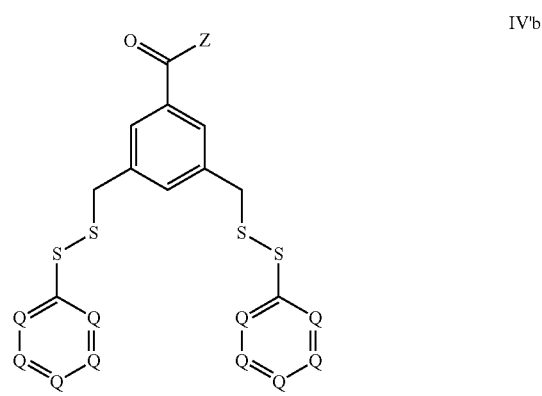

IV'b wherein Q at each instance is independently CH or N.

In some embodiments, the compound has the following structure

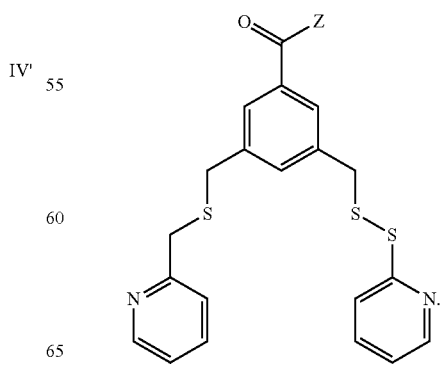

Methods of Making

The compounds described herein can be prepared using synthetic techniques known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or 0-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxyacetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxyacetamidoethyl resin is O-benzotriazol-1-yl-N,N, N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

In a specific method disclosed herein are methods of making a bicyclic peptide comprising, contacting a compound of Formula IV:

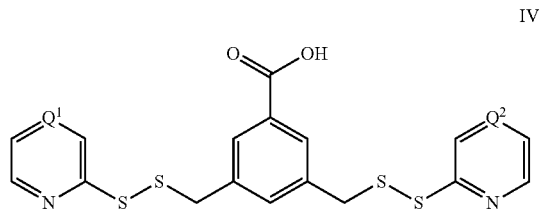

IV wherein $Q^1$ and $Q^2$ are, independent of one another, chosen from CH or N; with a solid supported peptide having from 8 to 20 amino acid residues, wherein at least two residues are cysteine residues; and cleaving the peptide from the solid support. Examples of suitable solid supports are polystyrene, polyacrylamide, polyethylene glycol supports. Rink, Wang, or Tentagel resins are suitable examples of solid supports that can be used. Cleaving the peptide from the solid supports can typically be accomplished with mild acid or base.

Methods of Use

Also provided herein are methods of use of the compounds or compositions described herein. Also provided herein are methods for treating a disease or pathology in a subject in need thereof comprising administering to the subject an effective amount of any of the compounds or compositions described herein.

Also provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Further examples of cancers treatable by the compounds and compositions described herein include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. Further examples of cancers treatable by the disclosed compounds are p53 cancers, e.g., by using compounds where the cargo moiety is SEQ ID NO.: 156, e.g., SEQ ID NO.:166 and SEQ ID NO.:167.

The methods of treatment or prevention of cancer described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent.

The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation.

An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples of the methods of treating of treating, preventing, or ameliorating cancer or a tumor in a subject, the compound or composition administered to the subject can comprise a therapeutic moiety that can comprise a targeting moiety that can act as an inhibitor against Ras (e.g., K-Ras), PTP1B, Pin1, Grb2 SH2, or combinations thereof.

The disclosed subject matter also concerns methods for treating a subject having a metabolic disorder or condition. In one embodiment, an effective amount of one or more compounds or compositions disclosed herein is administered to a subject having a metabolic disorder and who is in need of treatment thereof. In some examples, the metabolic disorder can comprise type II diabetes. In some examples of the methods of treating of treating, preventing, or ameliorating the metabolic disorder in a subject, the compound or composition administered to the subject can comprise a therapeutic moiety that can comprise a targeting moiety that can act as an inhibitor against PTP1B. In one particular example of this method the subject is obese and the method comprises treating the subject for obesity by administering a composition as disclosed herein.

The disclosed subject matter also concerns methods for treating a subject having an immune disorder or condition. In one embodiment, an effective amount of one or more compounds or compositions disclosed herein is administered to a subject having an immune disorder and who is in need of treatment thereof. In some examples of the methods of treating of treating, preventing, or ameliorating the immune disorder in a subject, the compound or composition administered to the subject can comprise a therapeutic moiety that can comprise a targeting moiety that can act as an inhibitor against Pin1.

The disclosed subject matter also concerns methods for treating a subject having cystic fibrosis. In one embodiment, an effective amount of one or more compounds or compositions disclosed herein is administered to a subject having cystic fibrosis and who is in need of treatment thereof. In some examples of the methods of treating the cystic fibrosis in a subject, the compound or composition administered to the subject can comprise a therapeutic moiety that can comprise a targeting moiety that can act as an inhibitor against CAL PDZ.

Compositions, Formulations and Methods of Administration

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively, or an immunotherapeutic such as ipilimumab and bortezomib.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The disclosed compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1. Synthesis of Bicyclizatoin Scaffold

Reagents for peptide synthesis were purchased from Chem-Impex (Wood Dale, Ill.), NovaBiochem (La Jolla, Calif.), or Anaspec (San Jose, Calif.). Rink amide resin LS (100-200 mesh, 0.2 mmol/g) was purchased from Advanced ChemTech. Cell culture media, fetal bovine serum, penicillin-streptomycin, 0.25% trypsin-EDTA, and DPBS were purchased from Invitrogen (Carlsbad, Calif.). Methyl 3,5-dimethylbenzoate, N-bromosuccinimide, diethyl phosphite, 2,2'-dipyridyl disulfide, and other organic reagents/solvents were purchased from Sigma-Aldrich (St. Louis, Mo.). Anti-GST-Tb and streptavidin-d2 were purchased from Cisbio (Bedford, Mass.). The NF-κB reporter (Luc)-HEK293 cell line and One-Step™ luciferase assay system were purchased from BPS Bioscience (San Diego, Calif.).

Scheme 2. Synthesis of the Bicyclization Scaffold.

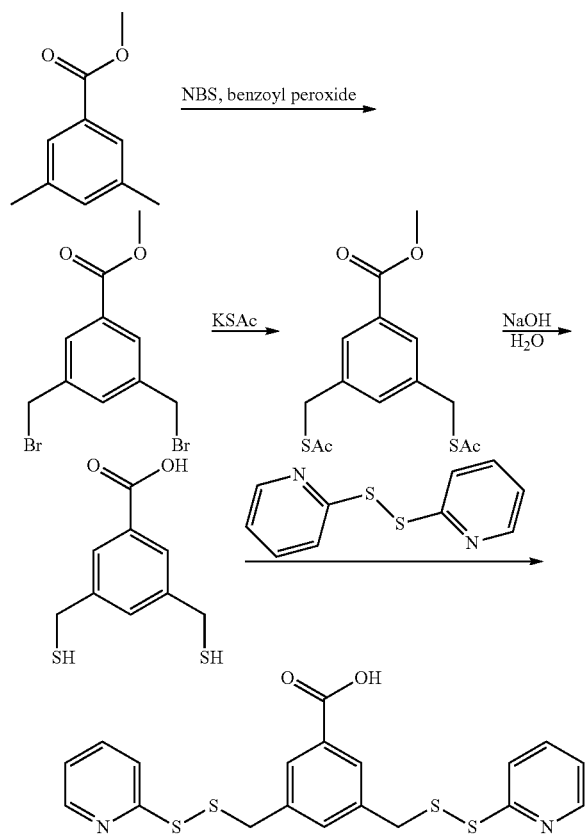

Synthesis of Methyl 3,5-bis(bromomethyl)benzoate

The overall synthetic plan for the bicyclization scaffold is shown in Scheme 2. To a 50-mL round-bottom flask charged with methyl 3,5-dimethylbenzoate (2.0 g, 12.2 mmol) in carbon tetrachloride (20 mL, sparged with nitrogen) was added N-bromosuccinimide (4.25 g, 23.9 mmol) and benzoyl peroxide (~60 mg) as an initiator. The reaction was refluxed for 3 h under nitrogen atmosphere. The reaction mixture was cooled, and filtered. The filtrate was washed with water (20 mL), dried with $MgSO_4$, and concentrated in vacuo. The crude product was recrystallized in petroleum ether to yield the title compound (1.2 g, 3.8 mmol) in 30% yield. $^1H$ NMR (300 MHz, $CDCl_3$): δ 7.99 (s, 2H), 7.62 (s, 1H), 4.50 (s, 4H), 3.94 (s, 3H).

Synthesis of Methyl 3,5-bis((acetylthio)methyl)benzoate

To a 50-mL round-bottom flask charged with crude methyl 3,5-bis(bromomethyl)benzoate (1.0 g, 3.1 mmol) from above was added acetone (20 mL) and potassium thioacetate (0.86 g, 7.52 mmol). The reaction was refluxed for 3 h under nitrogen atmosphere and allowed to cool. 20 mL water was added to quench the reaction and the mixture was extracted with ethyl acetate. The combined organic layer was dried with $MgSO_4$, concentrated, and purified by silica gel chromatography to afford 0.72 g of an orange-brown solid (74.2% yield). $^1H$ NMR (300 MHz, $CDCl_3$): δ 7.83 (s, 2H), 7.41 (s, 1H), 4.12 (s, 4H), 3.90 (s, 3H), 2.36 (s, 6H).

Synthesis of 3,5-bis((pyridin-2-yldisulfanyl)methyl)benzoic acid

A 50-mL round-bottom flask under nitrogen atmosphere was charged with methyl 3,5-bis((acetylthio)methyl)benzoate (0.5 g, 1.6 mmol) dissolved in MeOH (15 mL). A solution of NaOH (832 mg, 20.8 mmol) in $H_2O$ (3 mL) was added and the reaction was allowed to react overnight at room temperature. The reaction solution was acidified with AcOH (2.38 mL, 41.6 mmol) and 2, 2'-dipyridyl disulfide (1.41 g, 6.4 mmol) was added. The reaction mixture was filtered to remove the orange precipitate formed and allowed to stir for 1 h at room temperature. After the reaction was complete, the methanol was removed by evaporation in vacuo and the residue was quickly loaded onto a silica gel column. The column was first eluted with 20% to 50% EtOAc in hexanes to remove any low polarity species, after which the desired product was eluted with 1:1 (v/v) EtOAc in hexanes containing 1% AcOH. Evaporation of the solvents gave a brown solid (222 mg, 32% yield over two steps). $^1H$ NMR (400 MHz, $CDCl_3$): δ 8.43 (m, 2H), 7.83 (s, 2H), 7.53-7.43 (m, 5H), 7.04 (m, 2H), 3.97 (s, 4H). HRMS (ESI+): calcd for $C_{19}H_{17}N_2O_2S_4$ $(M+H^+)$: 433.0173; Found: 433.0176.

Example 2. Synthesis of Bicyclic Peptides

Peptide Preparation and Characterization. Peptides were synthesized on Rink amide resin LS (0.2 mmol/g) using standard Fmoc chemistry. A typical coupling reaction contained 5 equiv of Fmoc-amino acid, 5 equiv of 2-(7-aza-1H-benzotriazole-1-yl)-1,1,3,3-tetramethyluronium hexafluorophosphate (HATU), and 10 equiv of diisopropylethylamine (DIPEA) and was allowed to proceed for 45 min with gentle mixing. The peptides were deprotected and released from the resin by treatment with 90:2.5:2.5:2.5:2.5 (v/v) TFA/1,2-ethanedithiol/water/phenol/triisopropylsilane (TIPS) for 2 h. The peptides were triturated with cold ethyl ether (3×) and purified by reversed-phase HPLC equipped with a $C_{18}$ column. Peptide labeling with fluorescein isothiocyanate (FITC) was performed by dissolving the purified peptides (~1 mg each) in 300 μL of 1:1:1 DMSO/DMF/150 mM sodium bicarbonate (pH 8.5) and mixing with 10 μL of FITC in DMSO (100 mg/mL). After 20 min at room temperature, the reaction mixture was purified again by reversed-phase HPLC to isolate the FITC-labeled peptide.

Figure 5A:
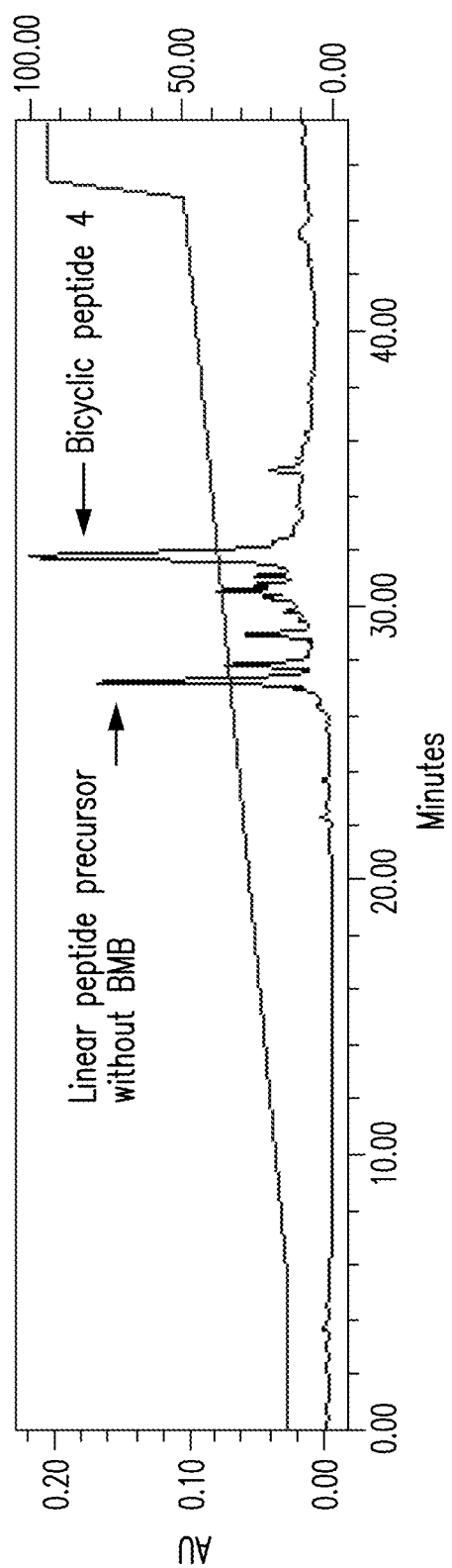
FIG. 5A is a preparative reversed-phase HPLC chromatogram showing the purification of crude peptide 4 following solid-phase synthesis and trituration with diethyl ether.
Figure 5B:
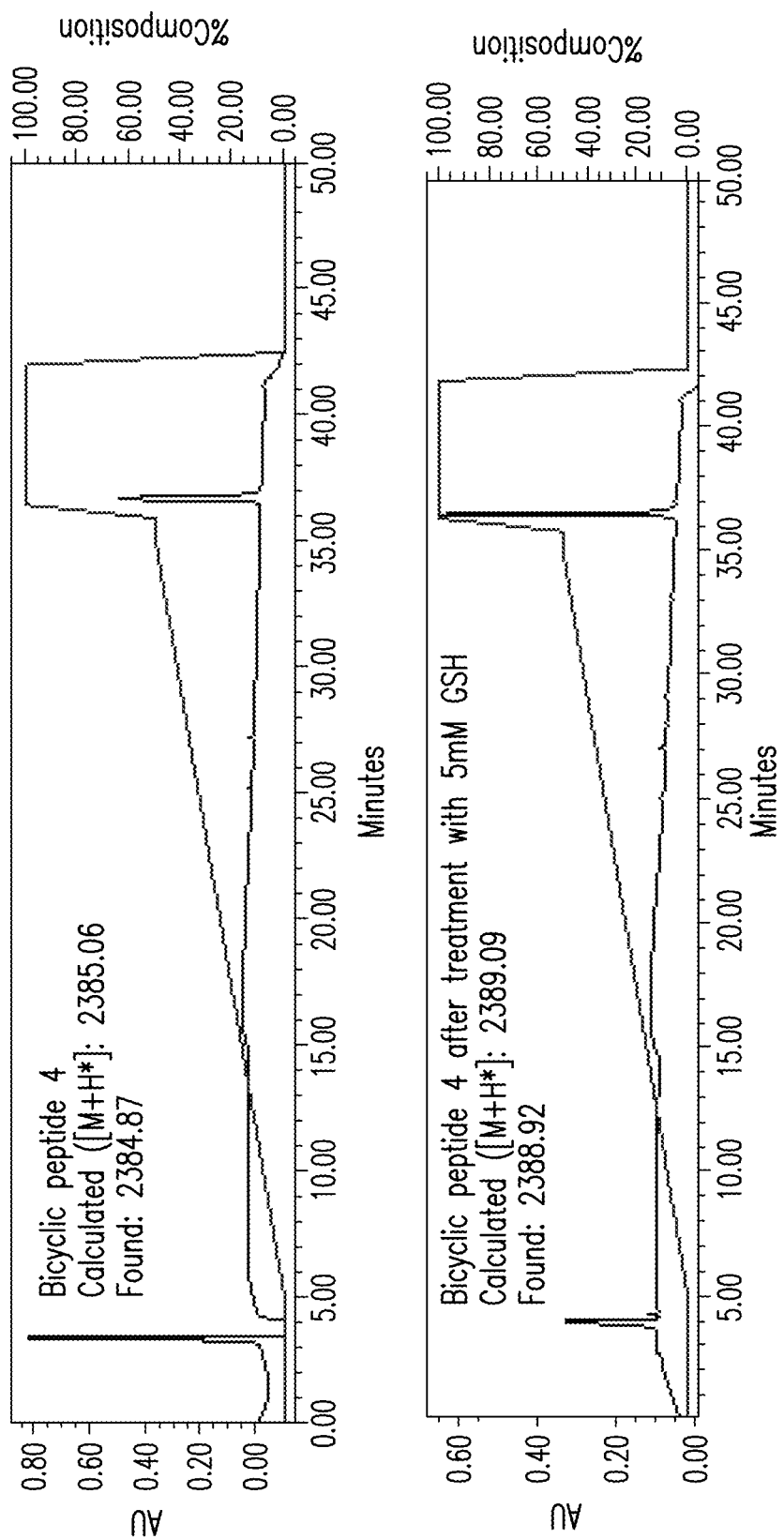
FIG. 5B is an analytical reversed-phase HPLC and MALDI-TOF MS analysis of purified peptide 4 before and after incubation with 5 mM glutathione in phosphate buffer (pH 7.4) at RT for 2 h.
Figure 5B:
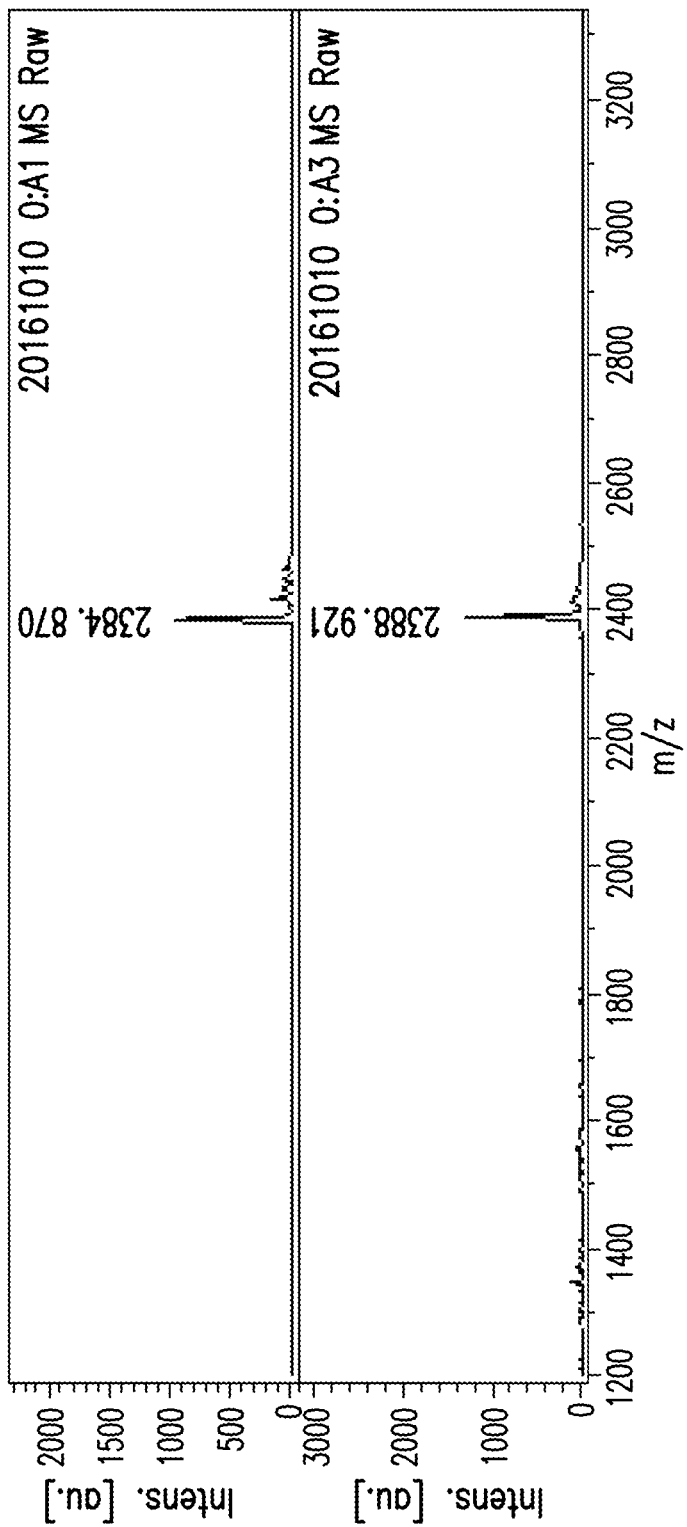
Figure 7:
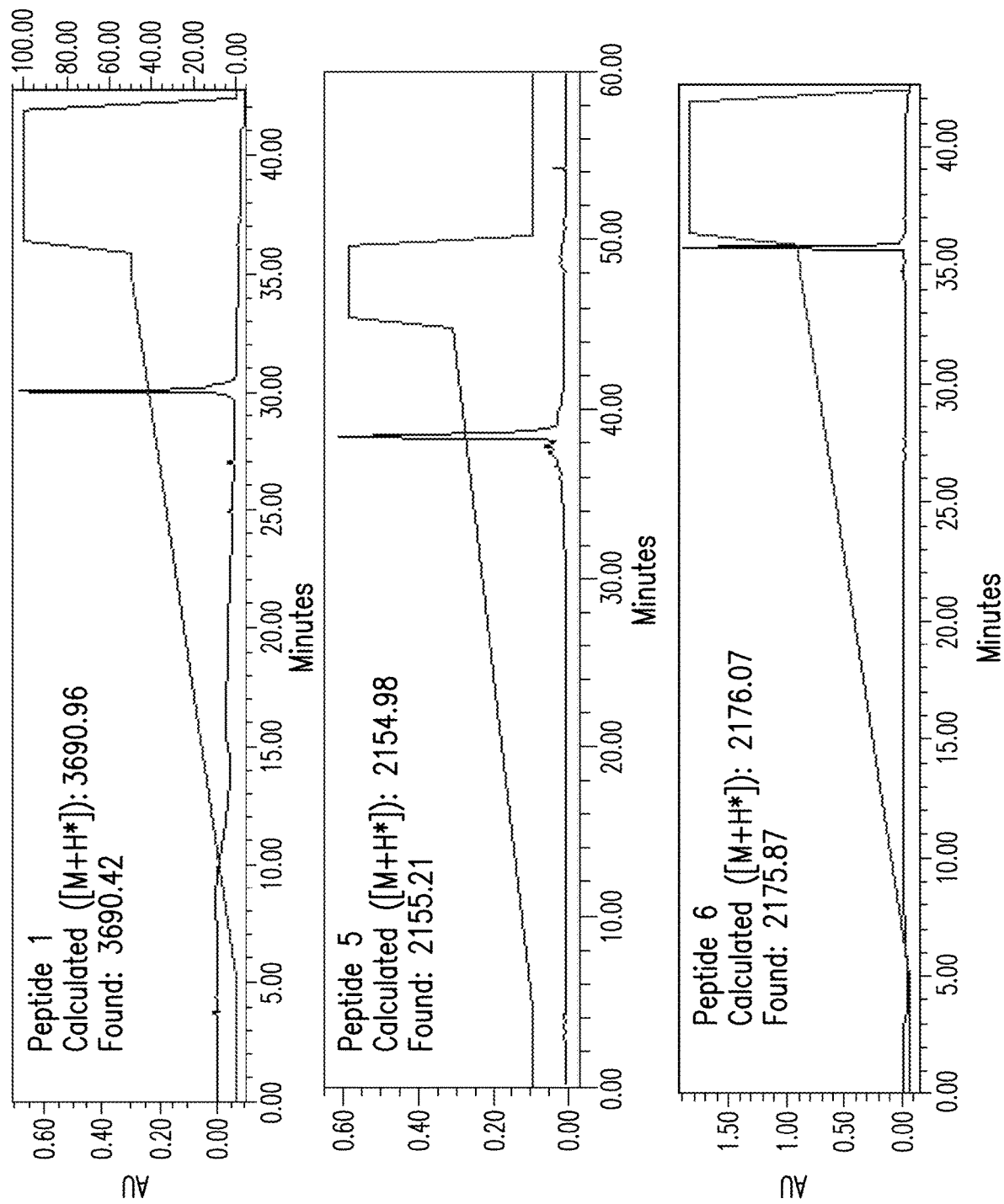
FIG. 7 is an analytical reversed-phase HPLC showing the purity of other peptides used in this work. The authenticity of the peptides was confirmed by MALDI-TOF MS analysis.

To synthesize the disulfide-mediated bicyclic peptides, the corresponding linear peptides containing two Acm-protected Cys residues were first prepared using standard Fmoc/HATU chemistry. The Acm groups were removed by treating the resin with 2 M mercury(II) acetate in DMF overnight. The resin was then incubated in 20% β-mercaptoethanol in DMF for 2 h (twice) to release the free thiol. After exhaustive washing with DMF to remove all of the reducing agents, the resin was incubated overnight with 1 equiv. of 3,5-bis((pyridin-2-yldisulfanyl)methyl)benzoic acid in methanol containing 1% (v/v) acetic acid. The reaction progress was monitored by removing a small portion of the resin and analyzing the deprotected/released peptide product by MALDI-TOF MS. Peptide deprotection and release were achieved by treating the resin with 85:10:2.5:2.5 (v/v) TFA/DCM/water/TIPS for 2 h, followed by ether trituration and HPLC purification as described above (FIG. 5A). All of the final peptides used in this work had >95% purity as judged by analytical HPLC (FIG. 5B and FIG. 7). The authenticity of the peptides was confirmed by MALDI-TOF MS analysis. To further characterize the biologically active peptide 4, the peptide was be dissolved in H$_2$O/D$_2$O (9:1, 500 µL; final sample concentration 2 mM). NMR spectra were recorded on a Bruker Ascend 700 MHz spectrometer at 298 K.

Example 3. Cell-Based Assays

Cell Culture.

HeLa cells were maintained in media consisting of DMEM, 10% fetal bovine serum (FBS) and 1% penicillin/streptomycin. The NF-κB reporter (Luc)-HEK293 cells were maintained in media consisting of DMEM, 10% FBS, 1% penicillin/streptomycin, and 100 µg/ml of hygromycin B. Cells were cultured in a humidified incubator at 37° C. in the presence of 5% CO$_2$.

Protein Expression and Purification.

*Escherichia coli* BL21(DE3) cells were transformed with a pGEX4T3-GST-NEMO(1-196) plasmid and grown at 37° C. in Luria broth supplemented with 0.05 mg/mL ampicillin to an OD$_{600}$ of 0.4. Expression was induced by the addition of isopropyl β-D-1-thiogalactopyranoside (150 µM final concentration). After five hours at 30° C., the cells were harvested by centrifugation. The cell pellet was suspended in 40 mL of lysis buffer (50 mM Tris-HCl, 100 mM NaCl, 0.5 mM MgCl$_2$, 5 mM β-mercaptoethanol, 0.1% Triton-X-100, pH 8.0), 100 µg/mL lysozyme, 100 µl DNAse I (New England BioLabs), and 100 µl of Halt Protease Inhibitor cocktail (EDTA-free) (Thermo Scientific). This mixture was stirred at 4° C. for 30 min and briefly sonicated (2×10 s pulses). The crude lysate was centrifuged to yield a clear supernatant, which was directly loaded onto a glutathione-Sepharose 4B column (GE Healthcare). The bound protein was eluted from the column with 10 mM Glutathione in 50 mM Tris-HCl (pH 8.0) (40 mL), concentrated to 0.5 mL with the use of Amicon Ultra-15 centrifugal filter units (MWCO 10 kDa), and dialyzed against PBS (2.67 mM potassium chloride, 1.47 mM potassium phosphate monobasic, 137 mM sodium chloride, and 8.06 mM sodium phosphate dibasic). To generate NEMO without the GST tag, the protein was treated with thrombin (GE Healthcare) for 16 h at 4° C. prior to concentration. Protein concentration was determined using Bradford assay with bovine serum albumin as the standard. The protein was quickly frozen and stored at −80° C.

An engineered prokaryotic expression plasmid pJCC04a,1 which encodes a fusion protein containing an N-terminal six-histidine tag, thioredoxin, a TEV protease cleavage site, and the K703R/K704R mutant form of IKKβ C-terminal fragment (amino acids 701-745) [His-thx-IKKβ$_{KK/RR}$(701-745)], was kindly provided by Dr. Maria Pellegrini (Dartmouth College). His-thx-IKKβ$_{KK/RR}$(701-745) was similarly expressed in *E. coli* BL21 (DE3) cells and purified by affinity chromatography using a HisTrap FF column (GE Healthcare). The fusion protein was eluted with 50 mM Tris-HCl (pH 8.0), 300 mM NaCl, 250 mM Imadizole, 2 mM β-mercaptoethanol and treated with TEV protease (150 units for 1 mg of fusion protein) for 16 h at 4° C. to remove the thioredoxin (thx). The resulting protease digestion mixture was re-loaded onto the HisTrap column. The flow-through fraction was collected and concentrated to ~2 mg/mL using Amicon Ultra-15 centrifugal filter units (MWCO 10 kDa). The IKKβ$_{KK/RR}$(701-745) protein was biotinylated by treatment with a 10-fold molar excess of biotin-NHS at 4° C. overnight. The biotinylated IKKβ$_{KK/RR}$(701-745) was purified by reversed-phase HPLC equipped with a C18 column and stored frozen at −80° C.

Flow Cytometry.

HeLa cells were cultured in six-well plates (5×10$^5$ cells per well) for 24 h. On the day of experiment, the cells were incubated with 5 µM FITC-labeled peptide in clear DMEM with 1% FBS at 37° C. for 2 h. The cells were washed with DPBS, detached from plate with 0.25% trypsin, diluted into clear DMEM containing 10% FBS, pelleted at 250 g for 5 min, washed once with DPBS and resuspended in DPBS containing 1% bovine serum albumin, and analyzed on a BD LSR II flow cytometer. Data were analyzed with Flowjo software (Tree Star).

Serum Stability Test.

The stability tests were carried by modifying a previously reported procedure.[2] Diluted human serum (25%) was centrifuged at 15,000 rpm for 10 min, and the supernatant was collected. A peptide stock solution was diluted into the supernatant to a final concentration of 5 µM and incubated at 37° C. At various time points (0-20 h), 200-µL aliquots were withdrawn and mixed with 50 µL of 15% trichloroacetic acid and 200 µL of acetonitrile, and the mixture was incubated at 4° C. overnight. The final mixture was centrifuged at 15,000 rpm for 10 min in a microcentrifuge, and the supernatant was analyzed by reversed-phase HPLC equipped with an analytical C$_{18}$ column (Waters). The amount of remaining peptide (%, relative to the time zero control) was determined by integrating the area underneath the peptide peak (monitored at 214 nm).

HTRF Assay.

Recombinant GST-NEMO (30 nM), biotin-IKKβ$_{KK/RR}$ (701-745) (50 nM), streptavidin labeled with d2 acceptor (2.5 µg/mL), anti-GST monoclonal antibody labeled with Tb donor (2.5 µg/mL), and varying concentrations of peptide (0-100 µM) were mixed in PBS containing 5 mM TCEP and 0.01% Triton X-100 (total volume 20 µL) in a 384-well plate. The plate was incubated for 2 h at room temperature. The HTRF signals were measured on a Tecan infinite M1000 Pro microplate reader and plotted as a function of the peptide concentration. The data was analyzed using GraphPad Prism 6.0 and IC$_{50}$ values were obtained by fitting the data to the dose-response inhibition curves.

NF-κB Luciferase Assay.

NF-κB reporter (Luc)-HEK293 cells were seeded in 96-well microplate in 45 µL of assay medium (DMEM, 10% FBS, and 1% penicillin/streptomycin, 1500 cells per well) and cultured overnight. Five µL of NEMO inhibitor in assay medium was added to cells and the cells were incubated for 2 h. Recombinant TNFα[3] in 5 µL of assay medium was added to the wells at the final concentration of 5 ng/mL. After 4 h of incubation, 55 µL of ONE-Step luciferase assay reagent was added to each well. Luminescence was measured after 10 min of incubation using a Tecan Infinite M1000 Pro microplate reader. Luciferase activities of TNFα unstimulated and stimulated cells were recorded as AU" and AU$^+$, respectively. Luciferase activities of TNFα stimulated cells after incubating with different concentrations of NEMO inhibitors were recorded as AU$^{pep}$. The inhibition of NF-κB signaling activation is calculated by the percentage of luciferase activity induction based on the equation:

Inhibition of TNFα Activation (%)=(AU$^{pep}$−AU$^-$)/(AU$^+$−AU$^-$)×100%

Results.

Figure 3:
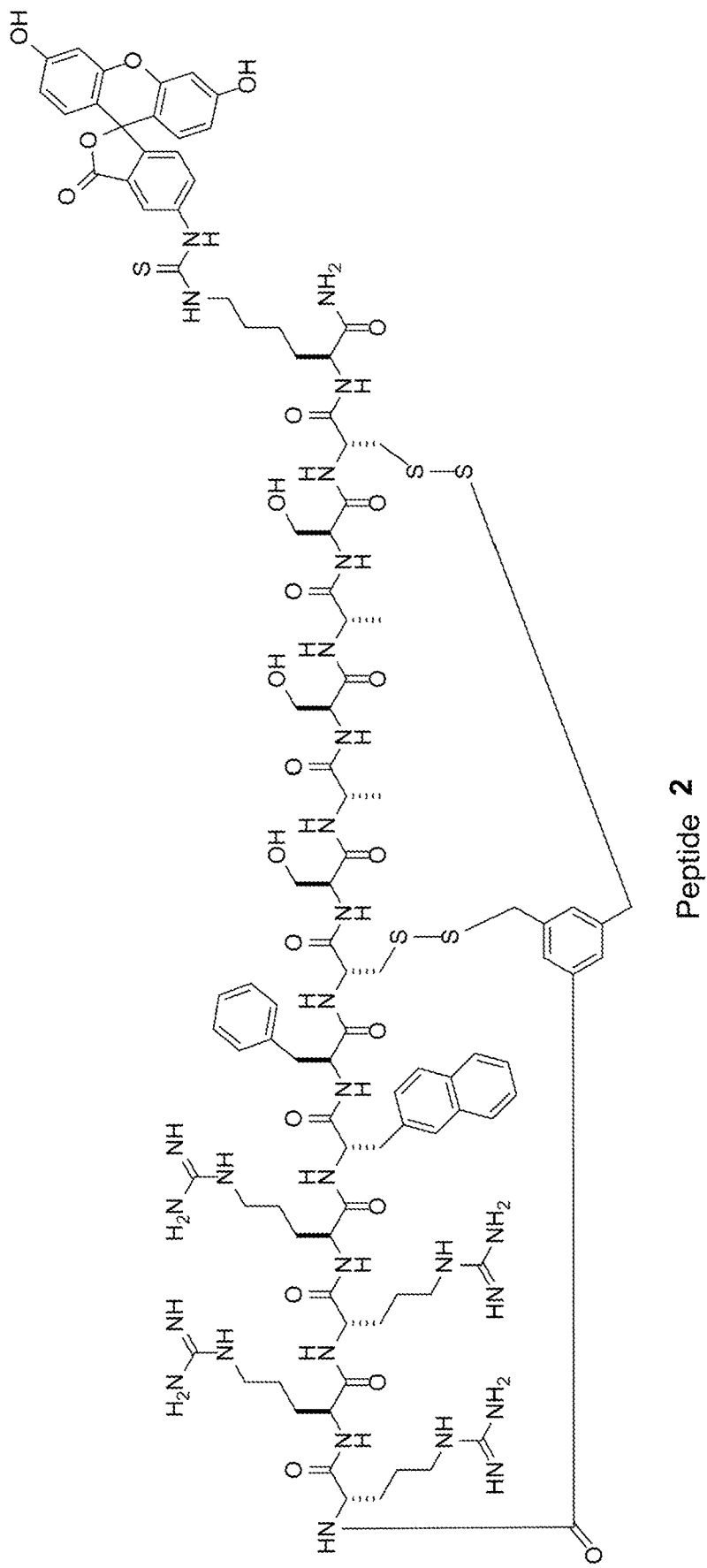
FIG. 3 shows the structures of FITC-labeled peptides 2 and 3.
Figure 3:
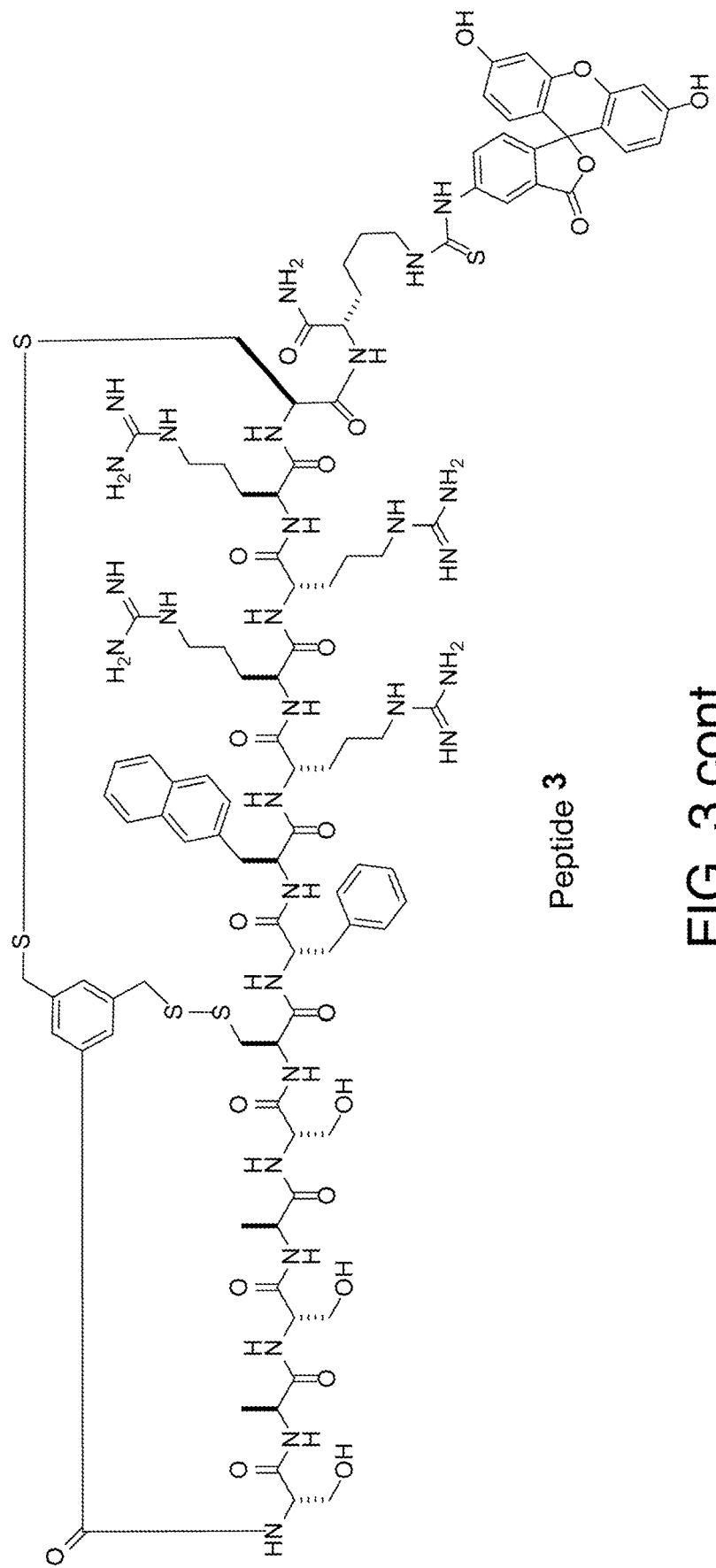

To test the validity of the reversible bicyclization strategy, two model peptides comprising the CPP motif (RRRRΦF (SEQ ID NO.:68) or FΦRRRR (SEQ ID NO.:69) and a mock cargo motif (SASAS ((SEQ ID NO.:156)) fused to its N- or C-terminus (Table 6, peptides 2 and 3, FIG. 3 for detailed structures) were designed. Two cysteine residues were also incorporated into the sequences for later cyclization, one at the junction between the CPP and cargo motifs and one at the C-terminus. The linear peptides were synthesized by standard Fmoc solid-phase peptide synthesis (SPPS) chemistry on Rink amide resin (Scheme 1). The acetamidomethyl (Acm) groups on the two cysteine side chains were selectively removed by treatment with Hg(OAc)$_2$ and the exposed free thiols were then reacted on-resin with 3,5-bis((pyridin-2-yldisulfanyl)methyl)benzoic acid, which was readily prepared from commercially available starting materials (Scheme 2). Formation of two disulfide bonds between the cysteine side chains and the 3,5-bis(mercaptomethyl)benzoic acid (BMB) scaffold resulted in cyclization of the peptide. Next, the N-terminal Fmoc group was removed by 1,8-diazabicyclo[5.4.0]undec-7-ene (DBU) and the peptide was bicyclized by forming a lactam between the carboxyl group of BMB and the N-terminal amine (Scheme 1). BMB is ideally suited as the scaffold, because its structural symmetry ensures that a single bicyclic product is formed following the disulfide exchange reactions. Additionally, the rigidity of the scaffold prevents the formation of any intramolecular disulfide bond, simplifying both the synthesis of the scaffold and its reaction with the cysteine-containing peptides.

To monitor their cellular uptake, peptides 2 and 3 were labeled with fluorescein isothiocyanate (FITC) on the side chain of a C-terminal lysine. Flow cytometry analysis of HeLa cells treated with 5 μM peptides cFΦR4 (SEQ ID NO.:72), 2 and 3 for 2 h showed mean fluorescence intensity (MFI) values of 3020, 5180, and 4100, respectively (FIG. 1A). Thus, bicyclic peptides 2 and 3 entered HeLa cells with 72% and 36% higher efficiencies, respectively, than cFΦR4 (SEQ ID NO.:72).

Figure 4:
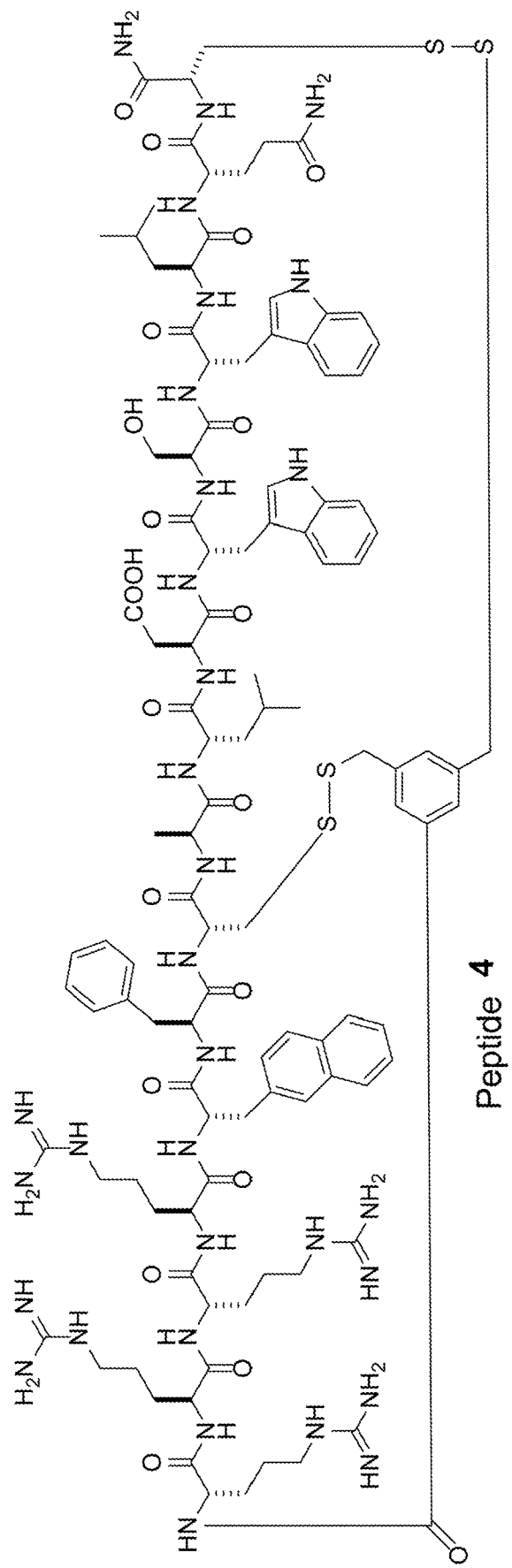
FIG. 4 shows the structures of peptides 4, 5, and 6.
Figure 4:
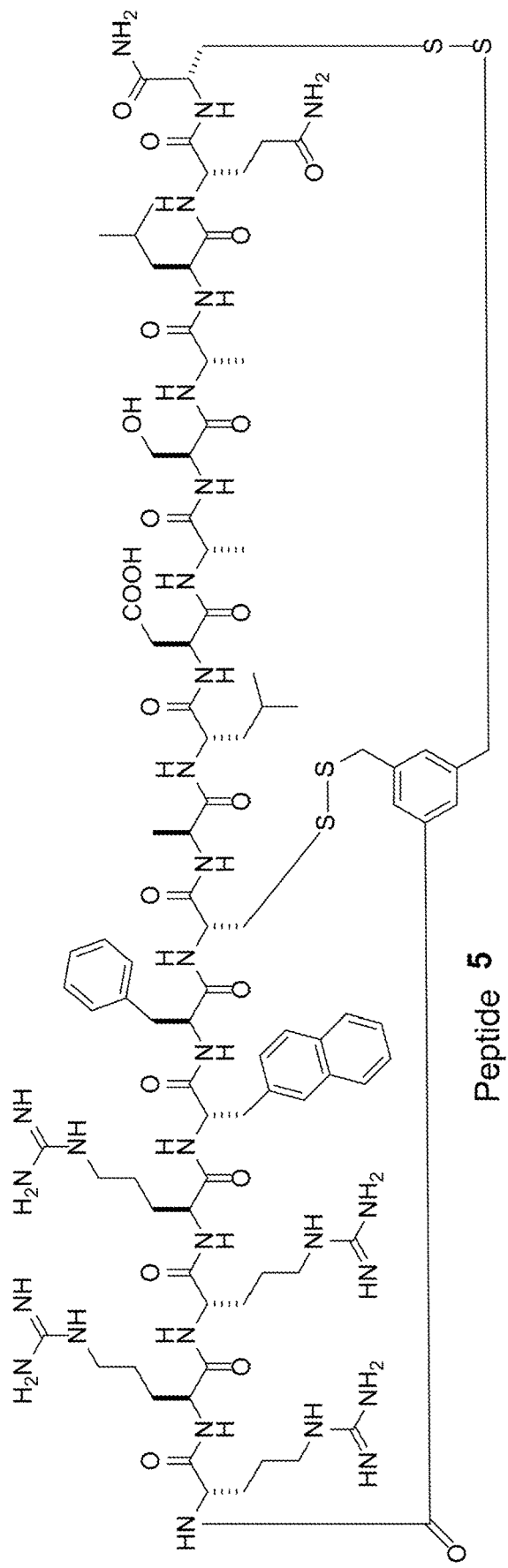
Figure 4:
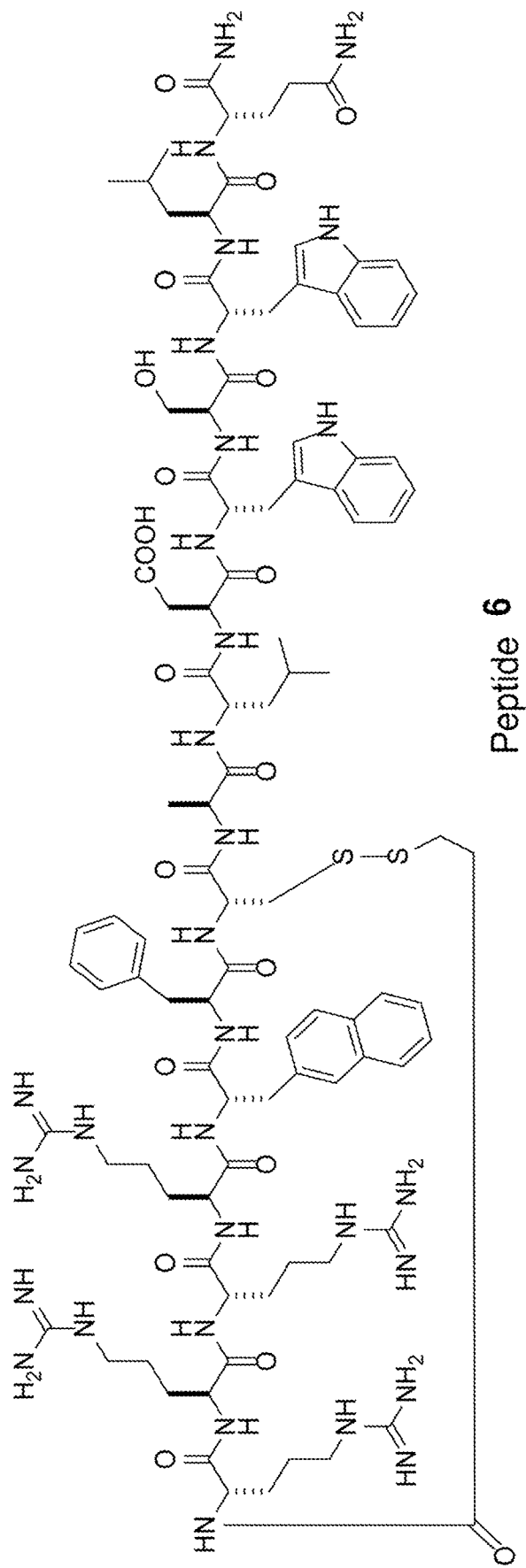

The reversible bicyclization strategy was applied to generate a cell-permeable, biologically active peptidyl inhibitor against the NEMO-IKK interaction. Despite of its in vivo efficacy, the linear Antp-NBD peptide has poor pharmacokinetics, due to rapid proteolytic degradation in serum ($t_{1/2}$~15 min). Conversion of Antp-NBD into a conformationally constrained bicyclic structure was envisioned to substantially increase its proteolytic stability. The CPP motif RRRRΦF (SEQ ID NO.:68) was fused to the N-terminus of NBD and the N- and C-terminal threonine residues were replaced with two cysteines (Table 6, peptide 4, FIG. 4 for detailed structure ((SEQ ID NO.:216). The peptide fusion was bicyclized around the BMB scaffold via two disulfide bonds as described above, to give bicyclic peptide 4 as the predominant product (FIG. 5A). As a control, peptide 5 (FIG. 4 for detailed structure) was also prepared, which is structurally similar to peptide 4 but contains two Ala residues in place of the two Trp residues. It was previously shown that replacement of the Trp residues with alanine largely abolished NEMO binding (M. J. May, et al., *Science* 2000, 289, 1550).

Scheme 1. Solid-phase synthesis of disulfide-mediated bicyclic peptides

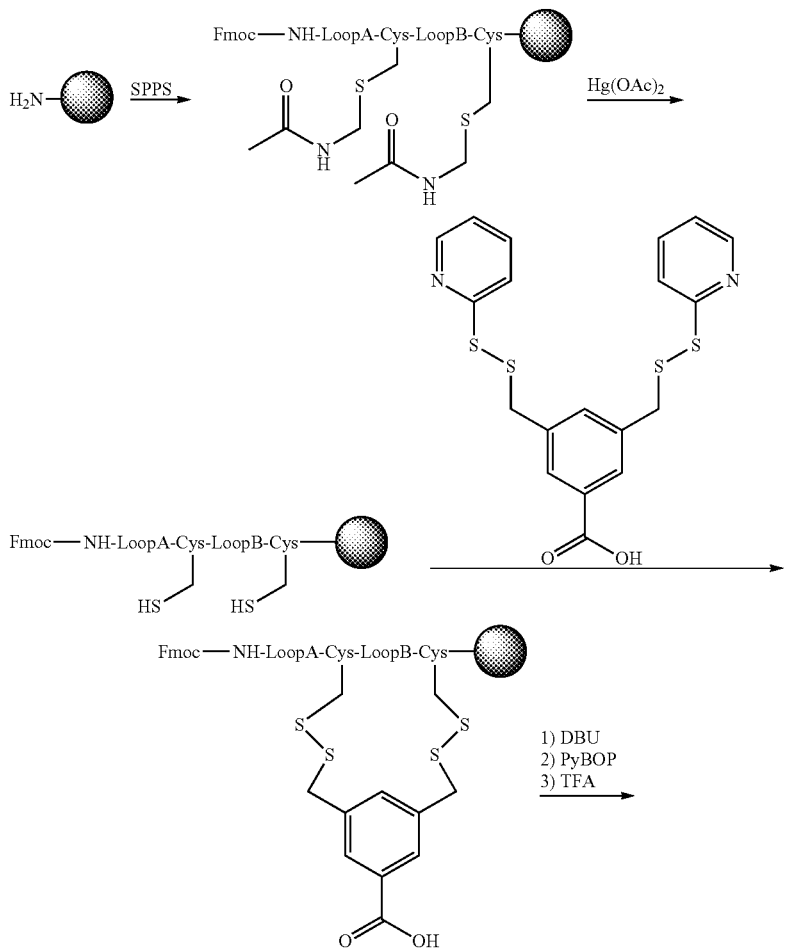

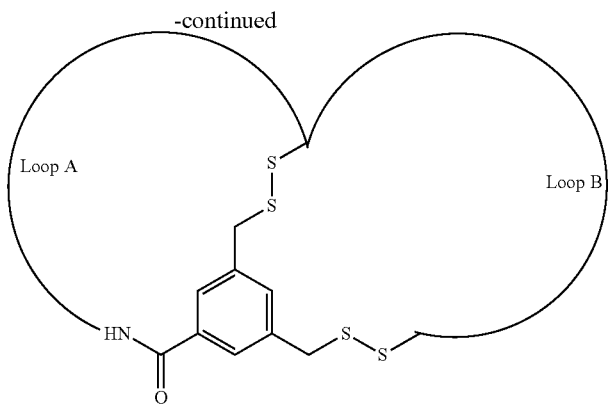

Figure 6:
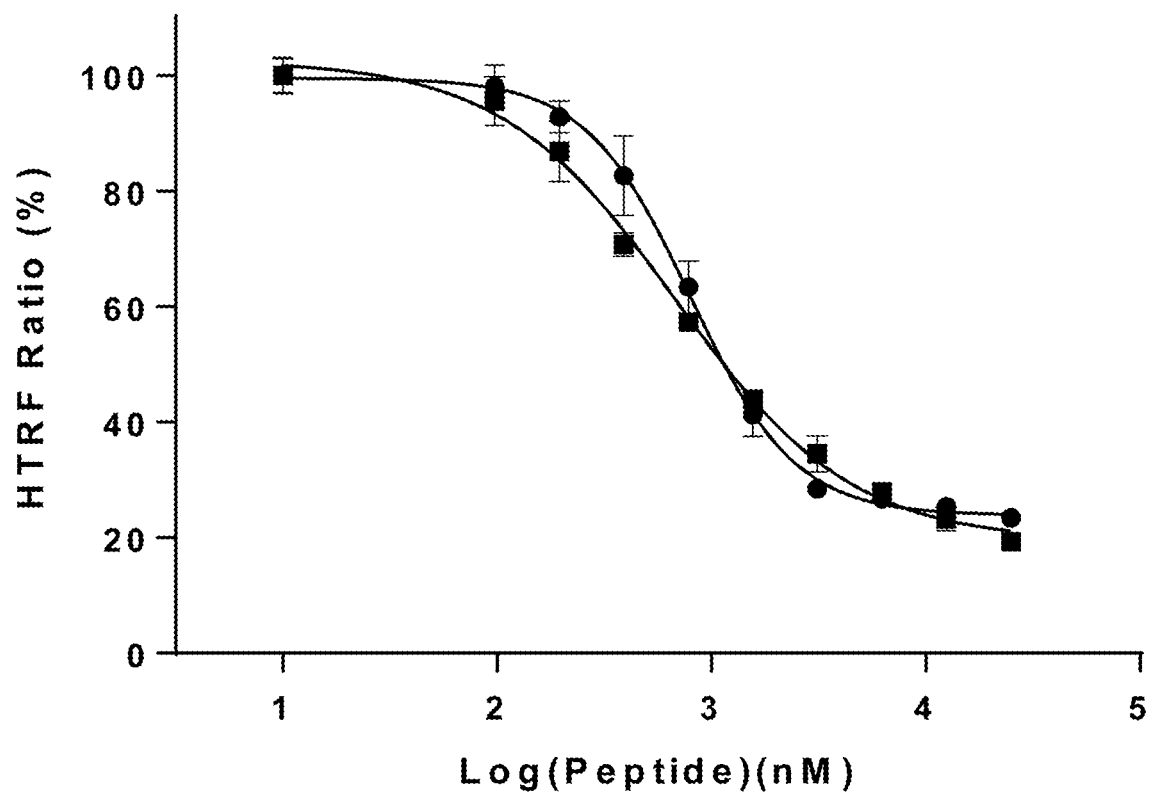
FIG. 6 shows the inhibition of the NEMO-IKKγ interaction by peptides RRRRΦFCALDWSWLQC (IC$_{50}$=1.4 µM) (SEQ ID NO.:215) and RRRRΦFTALDWSWLQT (IC$_{50}$=1.6 µM) (SEQ ID NO.:216) as monitored by the HTRF assay.

Peptides 4 and 5 were labeled with FITC at the side chain of a lysine added to their C-termini and their cellular entry was assessed by flow cytometry. Both peptides entered HeLa cells efficiently, exhibiting MFI values that were 3- and 2-fold higher than that of cFΦR[4], respectively (FIG. 1A). The NEMO-binding affinity of peptides 4 and 5 was determined using a homogenous time-resolved fluorescence (HTRF) assay (M. Rushe, et al., *Structure* 2008, 16, 798; Y. Gotoh, et al., *Anal. Biochem.* 2010, 405, 19). Briefly, in the presence of an anti-glutathione-S-transferase (GST) antibody labeled with a fluorescence donor (Tb) and streptavidin labeled with a fluorescence acceptor (d2), binding of GST-NEMO to a biotinylated IKKβ fragment (amino acids 701-745) (B. Gao, et al., *Biochemistry* 2014, 53, 677) results in a resonance energy transfer. Addition of a NEMO inhibitor blocks the NEMO-IKKβ interaction and reduces the HTRF signal. In the presence of 5 mM tris(carboxylethyl)phosphine (TCEP), which is expected to completely reduce the disulfide bonds in peptides 4 and 5, peptide 4 inhibited the NEMO-IKKβ interaction in a concentration-dependent manner, with a half-maximal inhibitory concentration ($IC_{50}$) value of 3.5±0.2 μM (FIG. 1B). Under the same conditions, Antp-NBD showed an $IC_{50}$ value of ~50 μM, in agreement with the previously reported binding affinity (M. Rushe, et al., *Structure* 2008, 16, 798; Y. Gotoh, et al., *Anal. Biochem.* 2010, 405, 19). As expected, up to 100 μM peptide 5 caused only minor inhibition of the interaction. Since substitution of the two cysteine residues for threonine did not significantly change the NEMO binding affinity (FIG. 6), the enhanced NEMO binding of peptide 4 relative to Antp-NBD is likely caused by additional interactions between the phenylalanine of the CPP motif (RRRRΦF (SEQ ID NO.:68)) and the NEMO protein surface. IKKβ contains a phenylalanine at the same position (Phe-734). The crystal structure of the NEMO-IKKβ complex shows that the side chain of Phe-734 inserts into a hydrophobic pocket on the NEMO surface (Id.). Thus, the phenylalanine in peptide 4 likely plays dual roles of cellular entry and NEMO binding.

The ability of the bicyclic peptides to modulate the NEMO-IKK interaction inside the cell was assessed by monitoring the TNFα-induced activation of NF-κB. HEK293 cells transfected with a luciferase reporter gene under the control of NF-κB were first treated with varying concentrations of a peptide for 2 h and then TNFα (M. J. May, et al., *Science* 2000, 289, 1550; A. Gaurnier-Hausser, et al., *Clin. Cancer Res.* 2011, 17, 4661). In the absence of any inhibitory peptide, treatment with 5 ng/mL TNFα increased the luciferase activity from a basal level of 177 arbitrary units (AU) to 715 AU. Peptide 4 reduced the TNFα-induced luciferase activity in a dose-dependent manner, with an $IC_{50}$ value of ~20 μM (FIG. 1C). In contrast, the control peptide 5 had no significant effect on NF-κB signaling at 20 μM and resulted in ~10% inhibition at the highest concentration tested (40 μM). Consistent with the earlier report (M. J. May, et al., *Science* 2000, 289, 1550), Antp-NBD (peptide 1) also caused concentration-dependent inhibition, but showed an $IC_{50}$ value of 140 μM. The higher potency of bicyclic peptide 4 relative to Antp-NBD in the cellular assay is likely the results of both improved cellular entry efficiency (FIG. 1A) and greater NEMO-binding affinity (FIG. 1B). In vitro treatment of bicyclic peptide 4 with 5 mM glutathione for 2 h completely reduced the disulfide bonds (FIG. 5B), suggesting that peptides 2-5 should undergo complete reduction upon cytosolic entry.

Finally, the proteolytic stability of peptide 4 and Antp-NBD was tested by incubating the peptides in human serum for varying lengths of time and the remaining amounts of intact peptides were quantitated by analytical HPLC. For comparison, a control peptide (Table 6, peptide 6) was synthesized, which has the same sequence as peptide 4 but only its CPP motif was cyclized. In agreement with the previous reports (E. Jimi, et al., *Nat. Med.* 2004, 10, 617; S. Dai, et al., *J. Biol. Chem.* 2004, 279, 37219; W. Shibata, et al., *J. Immunol.* 2007, 179, 2681; S. H. Dave, et al., *J. Immunol.* 2007, 179, 7852; A. Gaurnier-Hausser, et al., *Clin. Cancer Res.* 2011, 17, 4661; J. M. Peterson, et al., *Mol. Med.* 2011, 17, 508; D. A. Delfin, et al., *J. Transl. Med.* 2011, 9, 68; D. P. Reay, et al., *Neurobiol. Dis.* 2011, 43, 598; J. N. Kornegay, et al., *Skelet. Muscle* 2014, 4, 18; G. Habineza Ndikuyeze, et al., *PLoS One,* 2014, 9, e95404), Antp-NBD was rapidly degraded by human serum, with a half-life of ~15 min (FIG. 1D). In contrast, bicyclic peptide 4 showed a half-life of ~10 h, and 23% of the peptide remained intact after 20 h of incubation at 37° C. The monocyclic control peptide 6 was also rapidly degraded (with a half-life of ~30 min), likely due to proteolysis of the linear NBD sequence. It was previously shown that linear peptidyl cargos attached to the Gln side chain of cFΦR$_4$ were rapidly degraded in human serum (Z. Qian, et al., *Angew. Chem. Int. Ed.* 2015, 54, 5874; *Angew. Chem.* 2015, 127, 5972).

In conclusion, a simple method has been developed to efficiently deliver peptidyl ligands into mammalian cells, by fusing the peptide with a short CPP motif and reversibly cyclizing the fusion peptide through disulfide bonds. The resulting bicyclic peptide has greatly enhanced cellular uptake as well as proteolytic stability. This strategy should be applicable to delivering any linear peptides.

Example 4. Synthesis of Bicyclic Peptide that Releases Peptidyl Cargo from the Cyclic Cell-Penetrating Peptide in the Cytosol As shown below in Scheme 2, the desired cyclic CPP was first synthesized by standard solid-phase peptide synthesis using the Fmoc/HATU chemistry and anchored to the support through a Lys(Mtt) linker. While still on resin, the Mtt group is removed with 2% TFA and the exposed Lys side chain is coupled to the bis(mercaptomethyl)benzoic acid scaffold by using HATU. The cyclic CPP is then cleaved off the resin and deprotected by TFA. The free thiols are protected/activated by reacting the peptide in solution (pH 5) with dithiodipyridine to generate the CPP-scaffold. Finally, the desired CPP-peptide cargo conjugate is prepared by simply mixing the CPP-scaffold and a thiol-containing peptide in an aqueous buffer at pH 8.

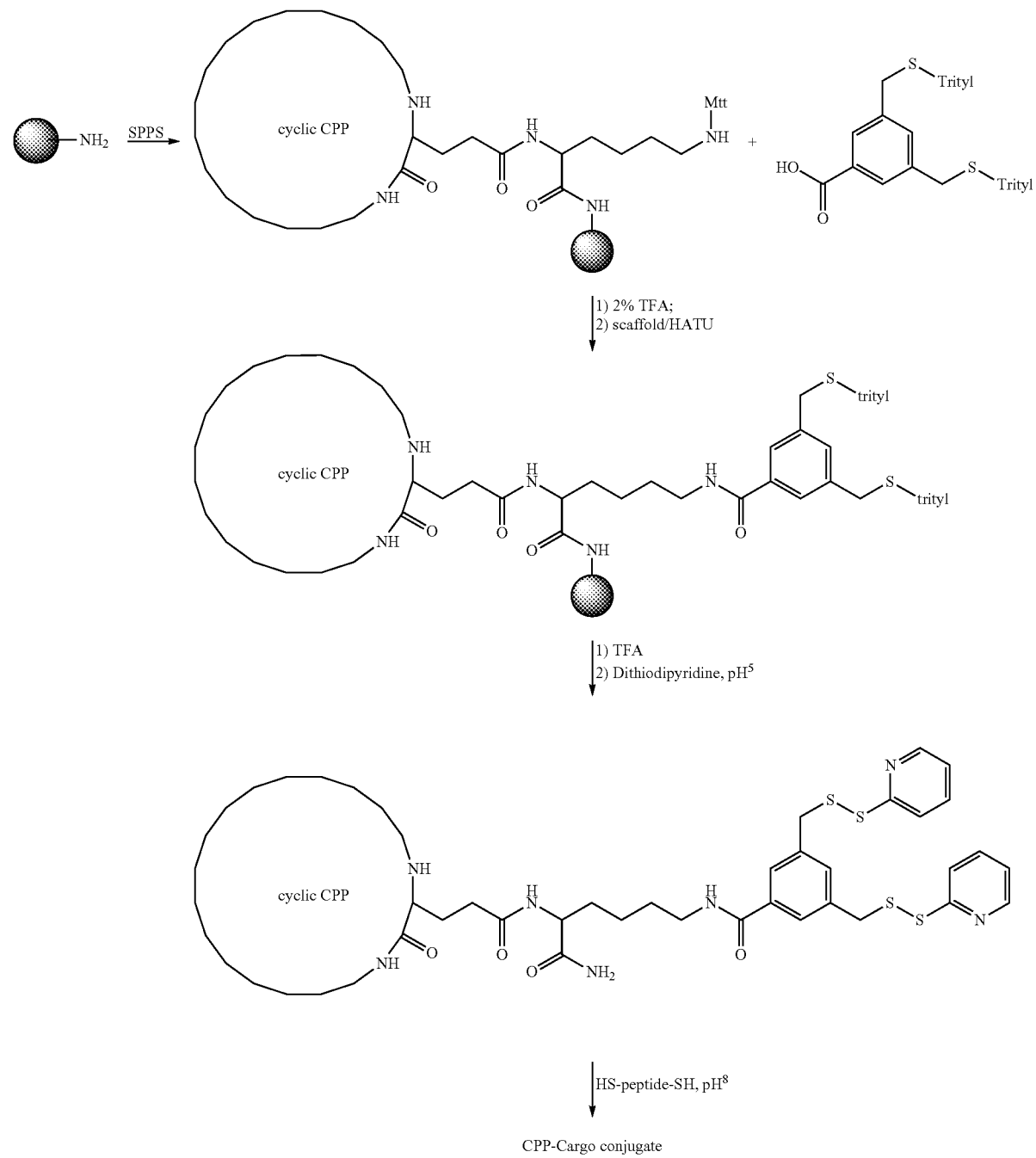

Scheme 2. Solid-phase synthesis of disulfide-mediated bicyclic peptides

Figure 10A:
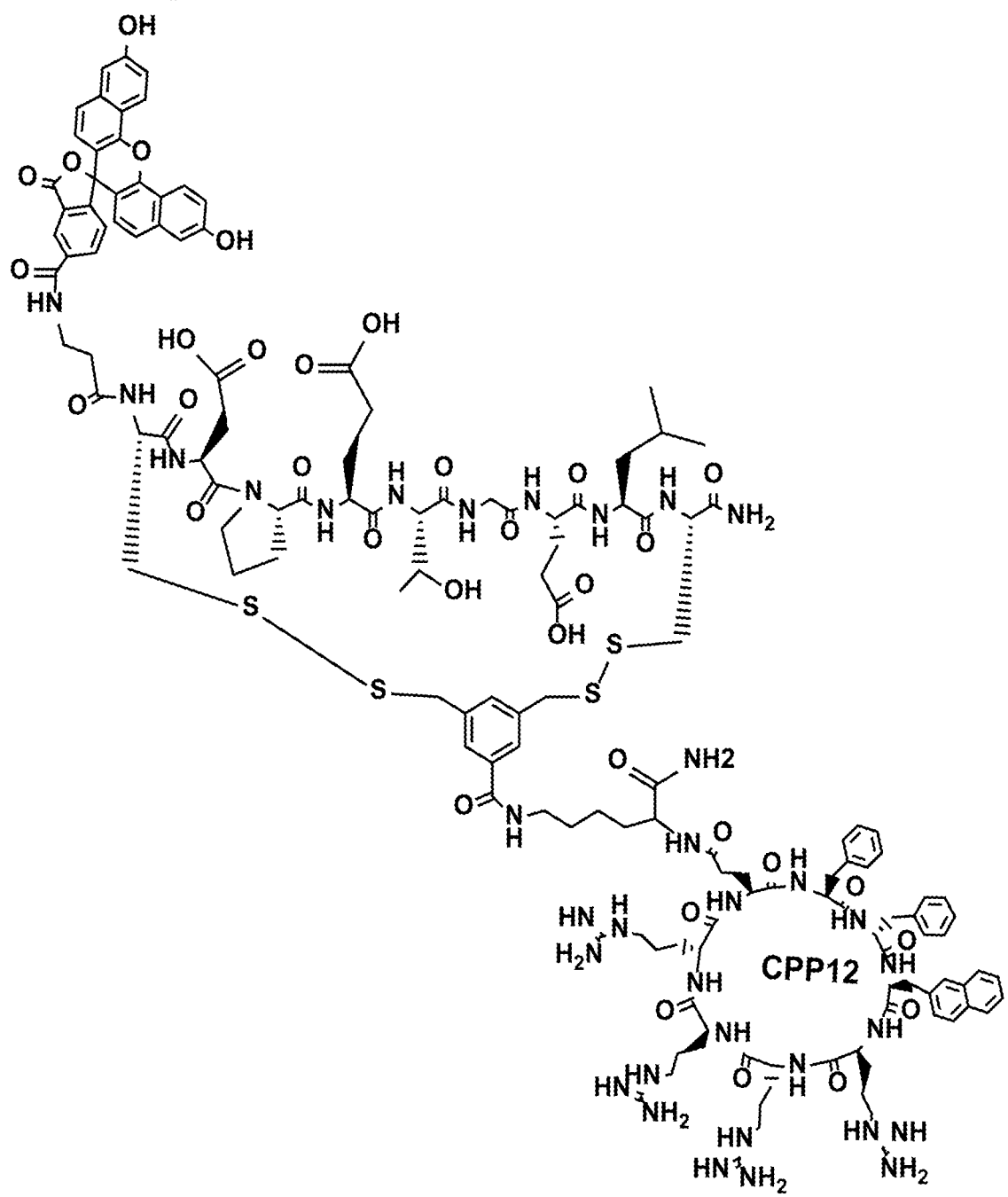
FIG. 10A shows the structure of a bicyclic peptide comprising cyclic comprising CPP12 (FfΦRrRr) conjugated to a peptidyl inhibitor against Keap1-Nrf2, having a fluorescent label (NFL).
Figure 10B:
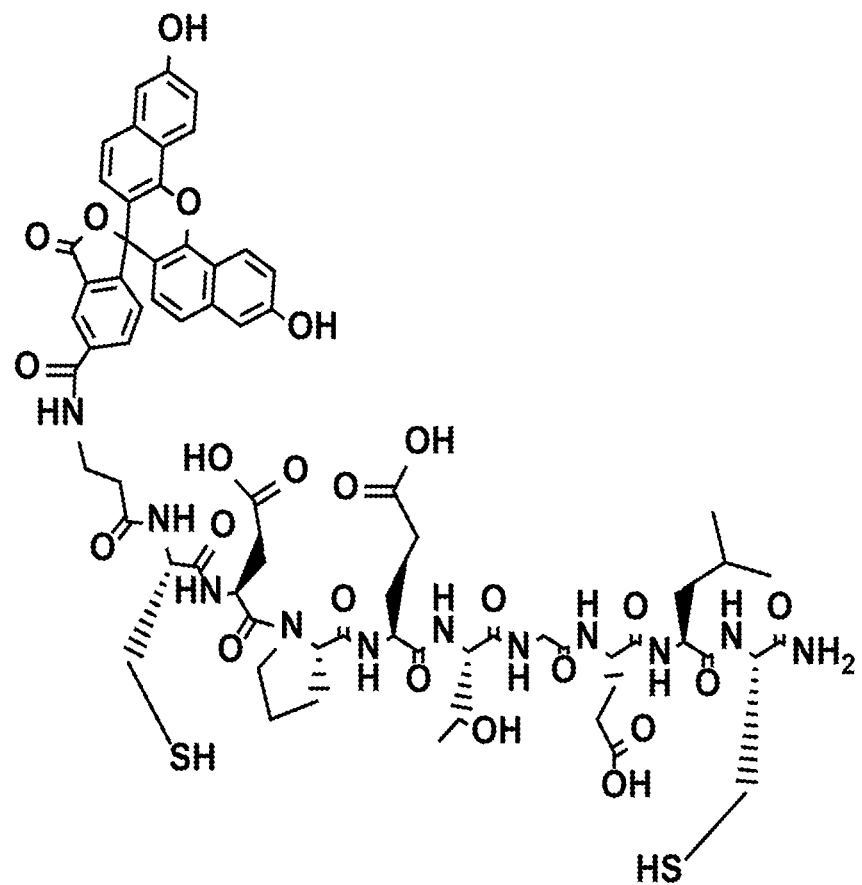
FIG. 10B shows a structure of the linear peptidyl inhibitor against Keap1-Nrf2, having a fluorescent label (NFL) in the absence of a cyclic CPP.
Figure 11:
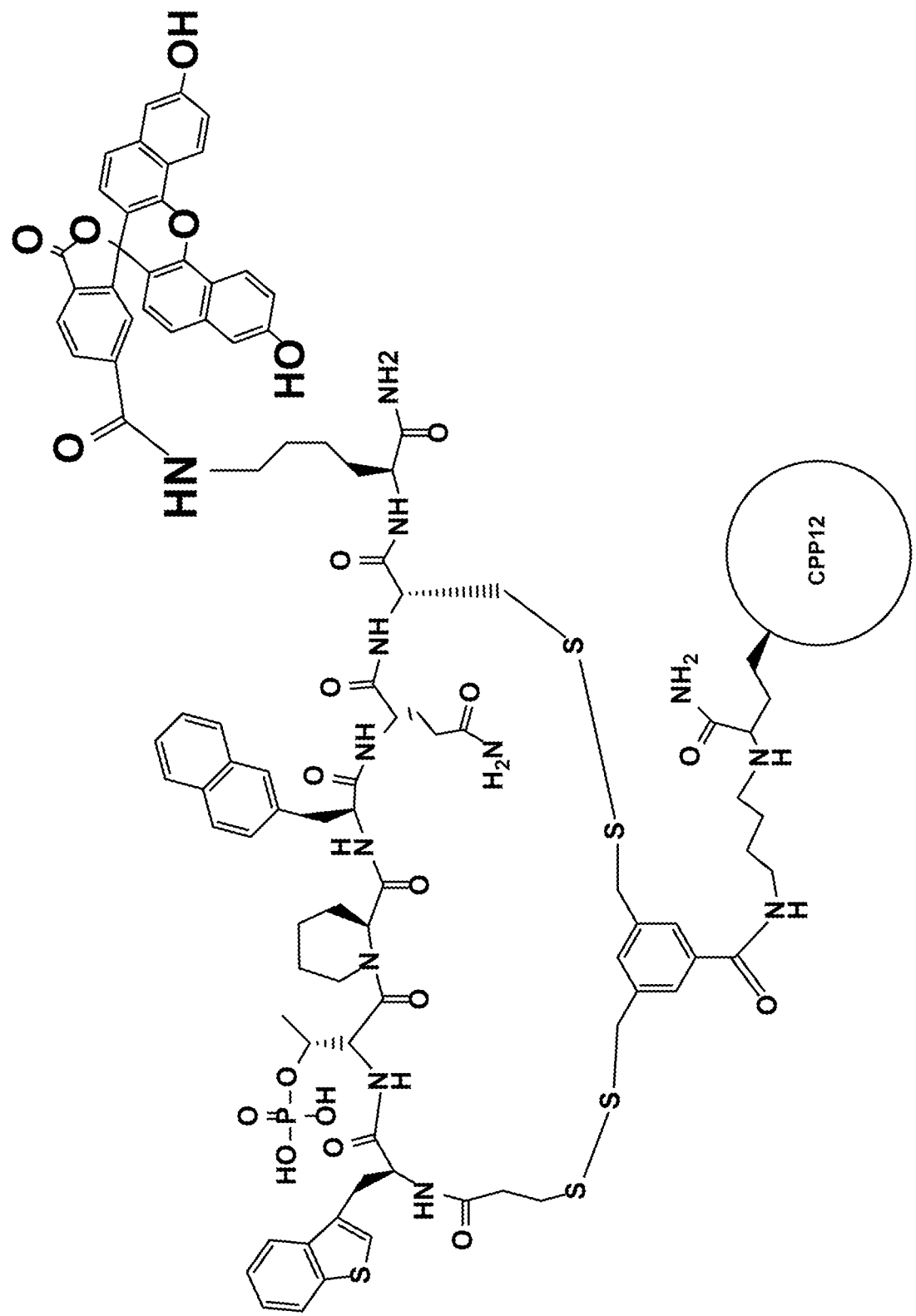
FIG. 11 shows the structure of a bicyclic peptide comprising cyclic comprising a cyclic CPP12 (FfΦRrRr) conjugated to a peptidyl inhibitor against Pin1, having a fluorescent label (NFL).
Figure 12A:
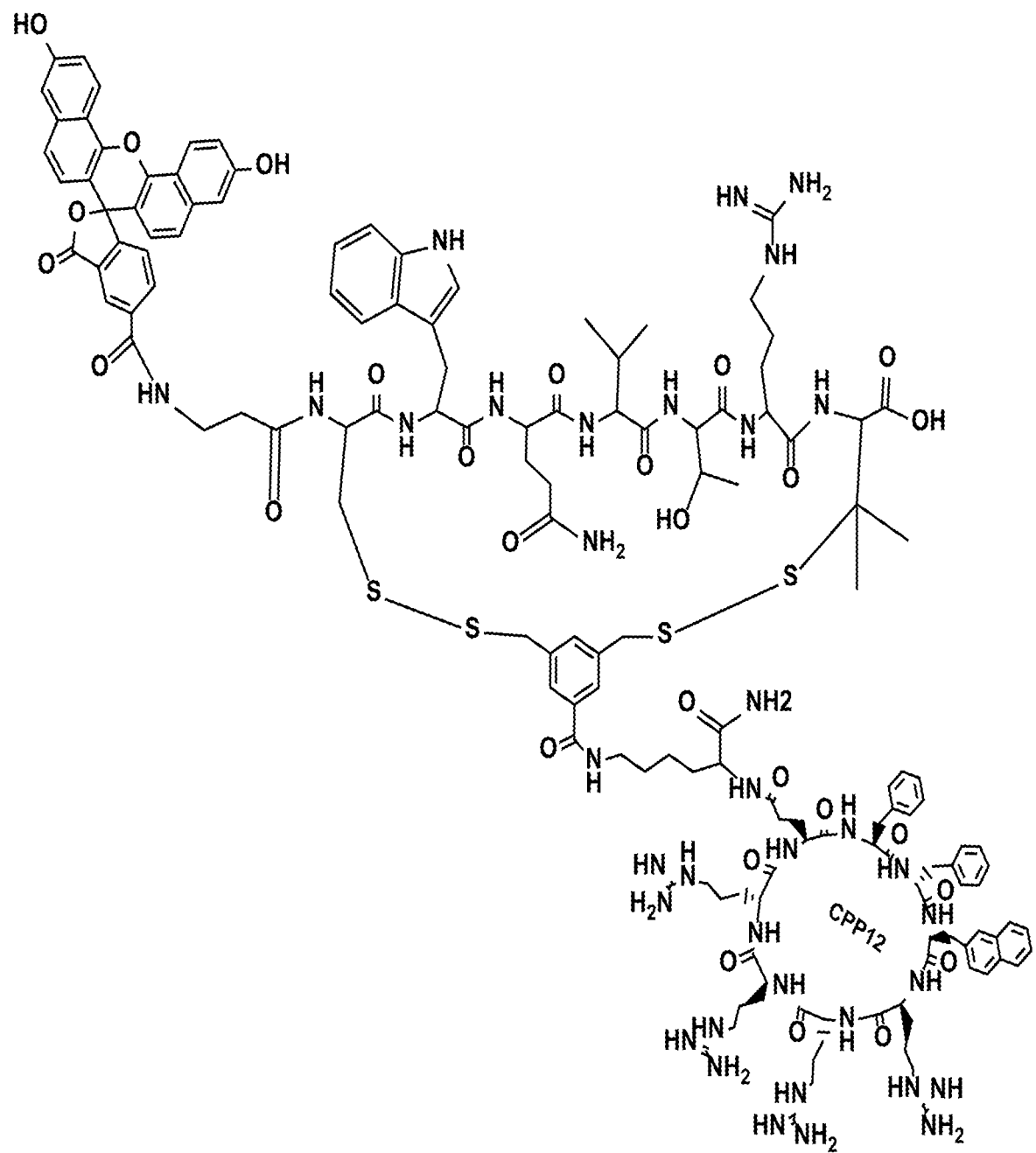
FIG. 12A shows the structure of a bicyclic peptide comprising cyclic comprising a cyclic CPP12 (FfΦRrRr) conjugated to a peptidyl inhibitor against the CAL PDZ-CFTR interaction, having a fluorescent label (NFL).
Figure 12B:
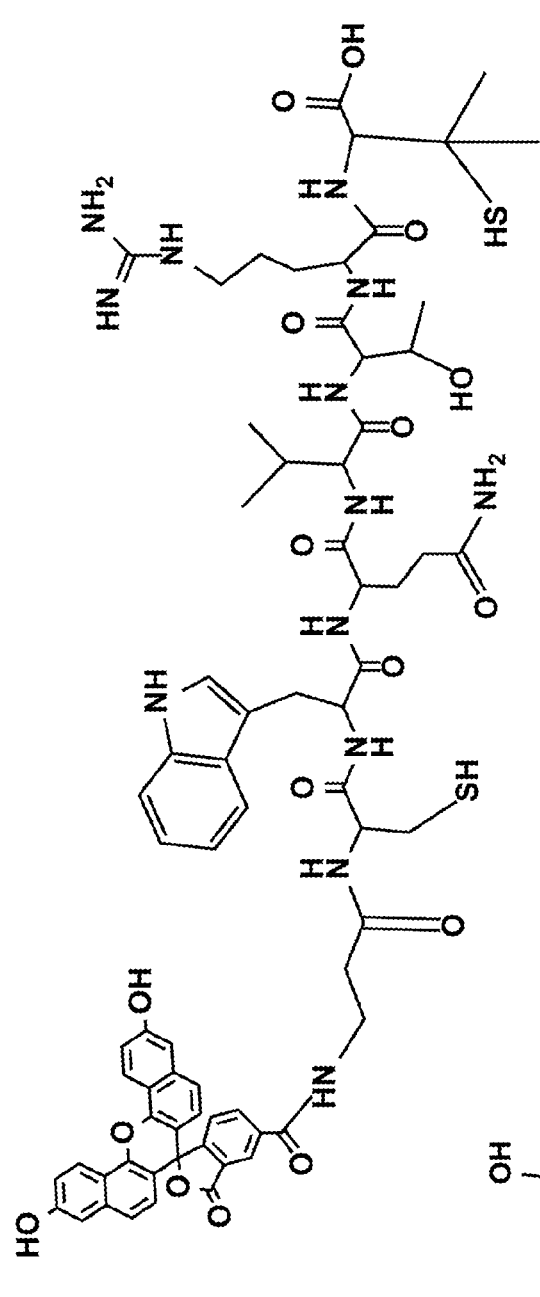
FIG. 12B shows a structure of the linear peptidyl inhibitor against the CAL PDZ-CFTR interaction, having a fluorescent label (NFL) in the absence of a cyclic CPP.
Figure 13A:
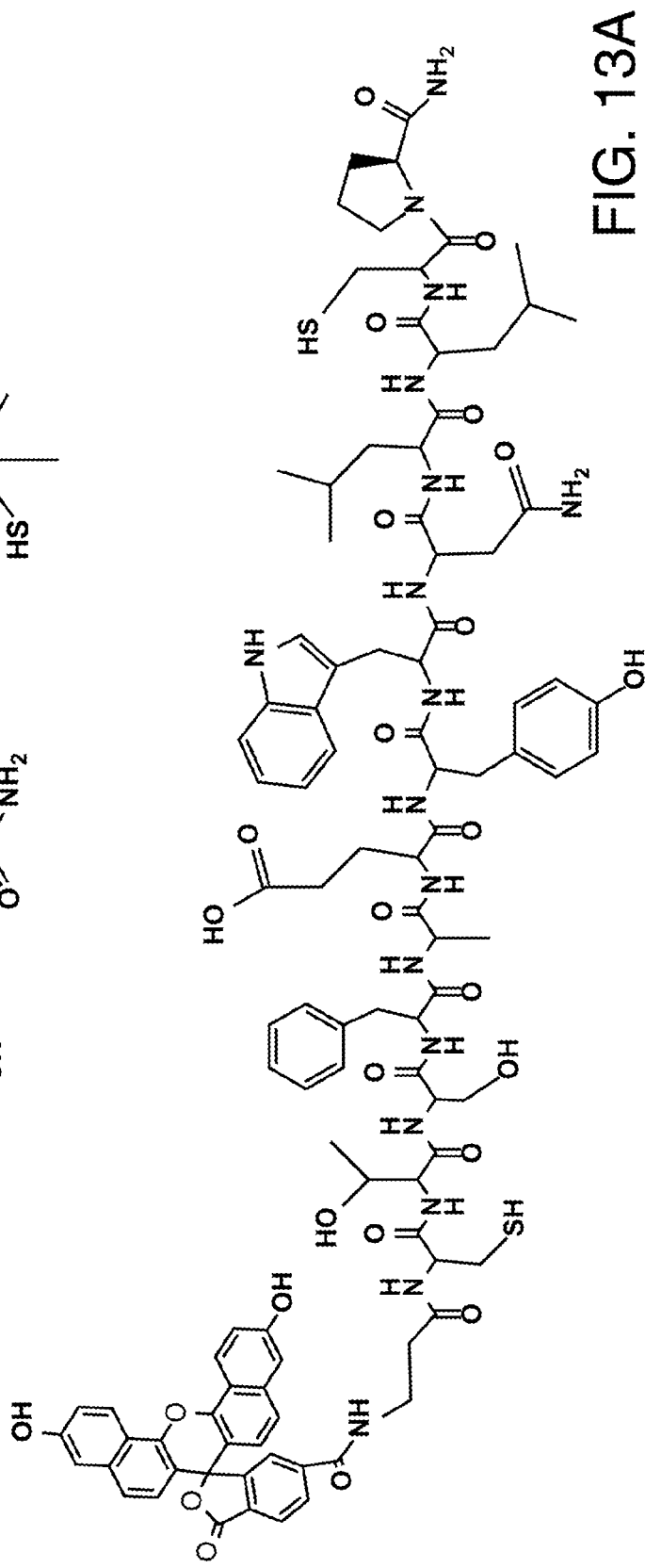
FIG. 13A shows the structure of a bicyclic peptide comprising cyclic comprising a cyclic CPP12 (FfΦRrRr) conjugated to a peptidyl inhibitor against the MDM2-p53 interaction (PMI), having a fluorescent label (NFL).
Figure 13B:
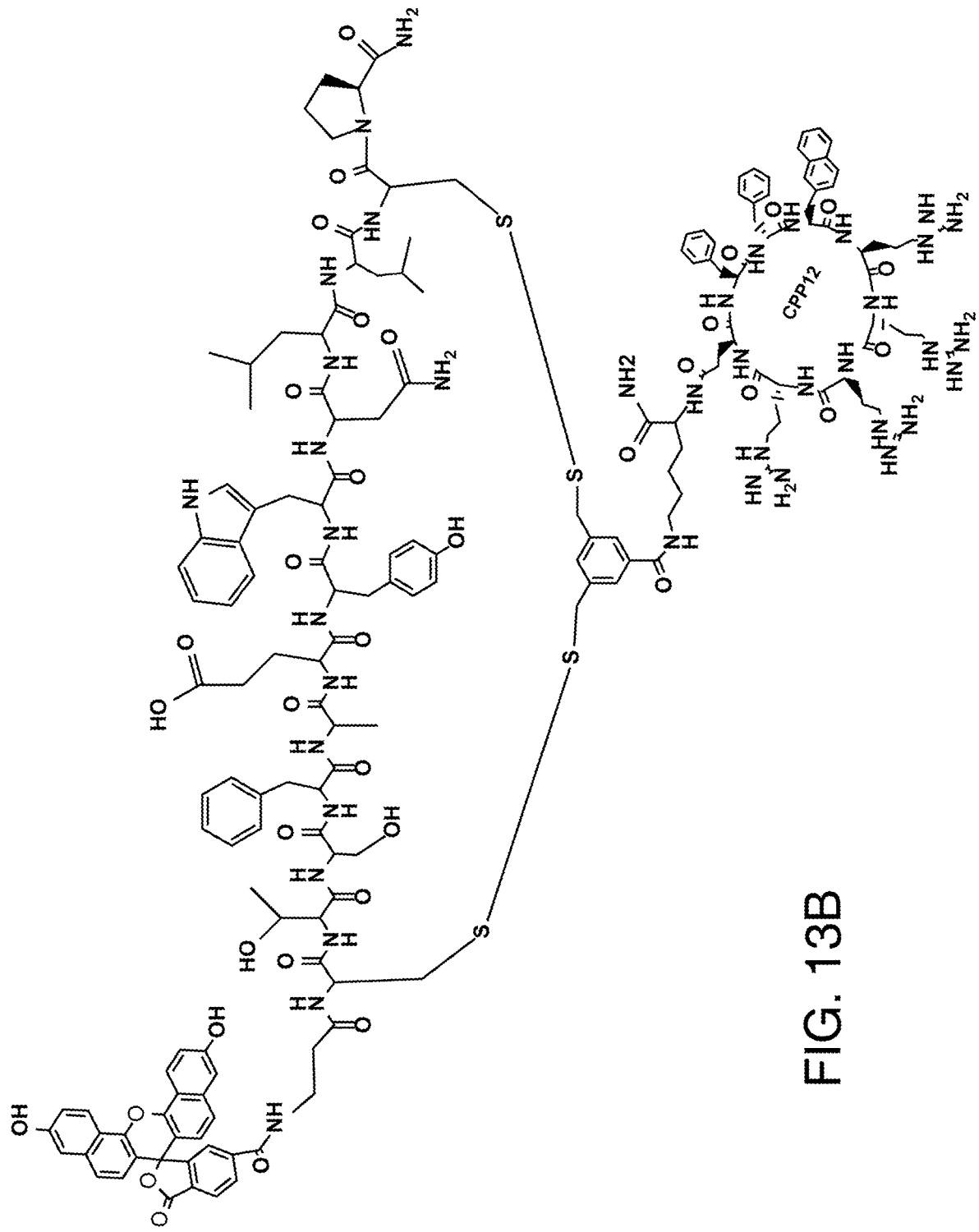
FIG. 13B shows a structure of the linear peptidyl inhibitor against the PMI, having a fluorescent label (NFL) in the absence of a cyclic CPP.
Figure 14:
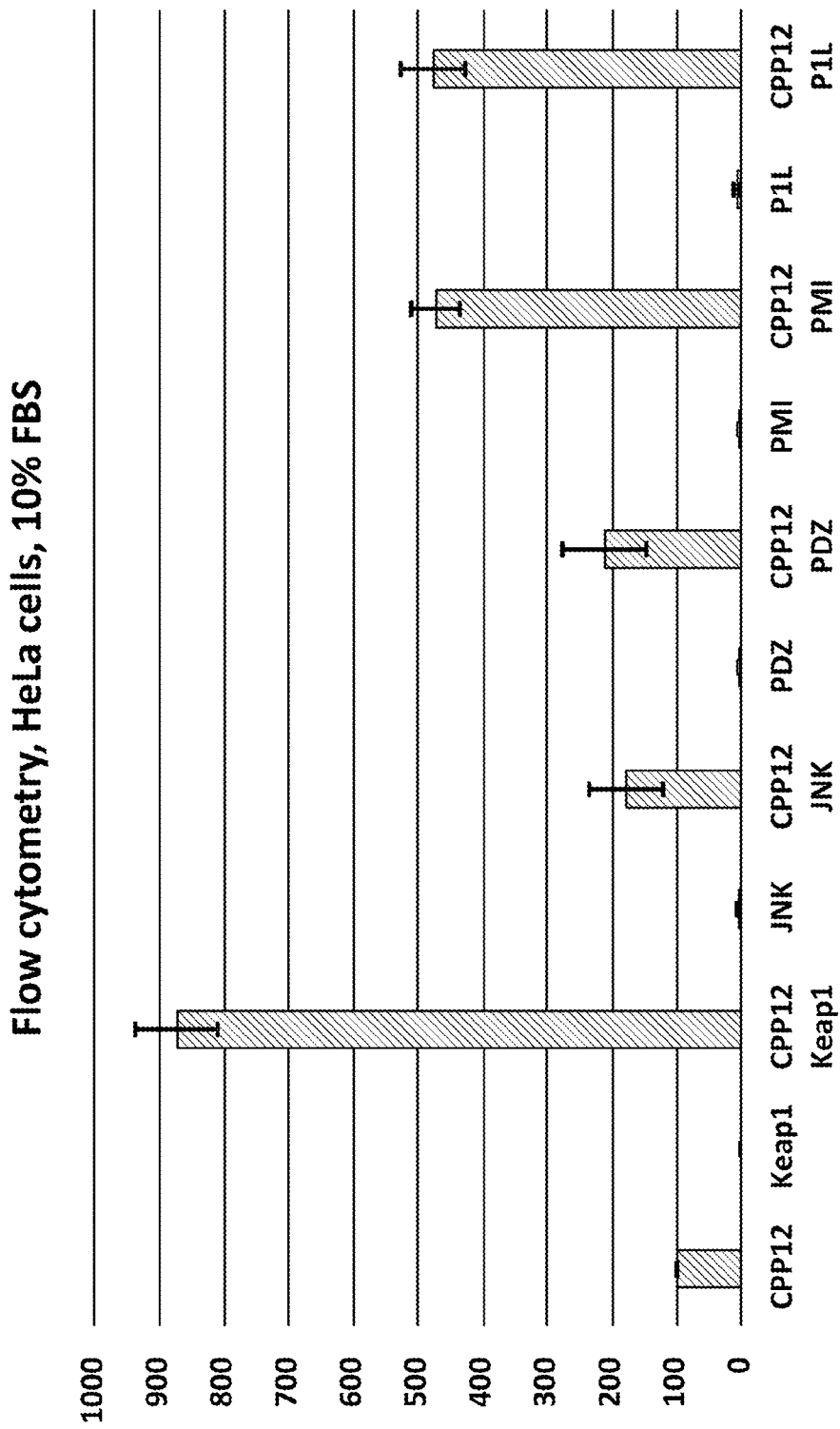
FIG. 14 graphically illustrates the cytosolic uptake efficiency of unconjugated peptidyl inhibitors compared to the cyclic CPP-peptide conjugates (i.e., the bicyclic peptides of the present disclosure).
Figures 15A, 15B:
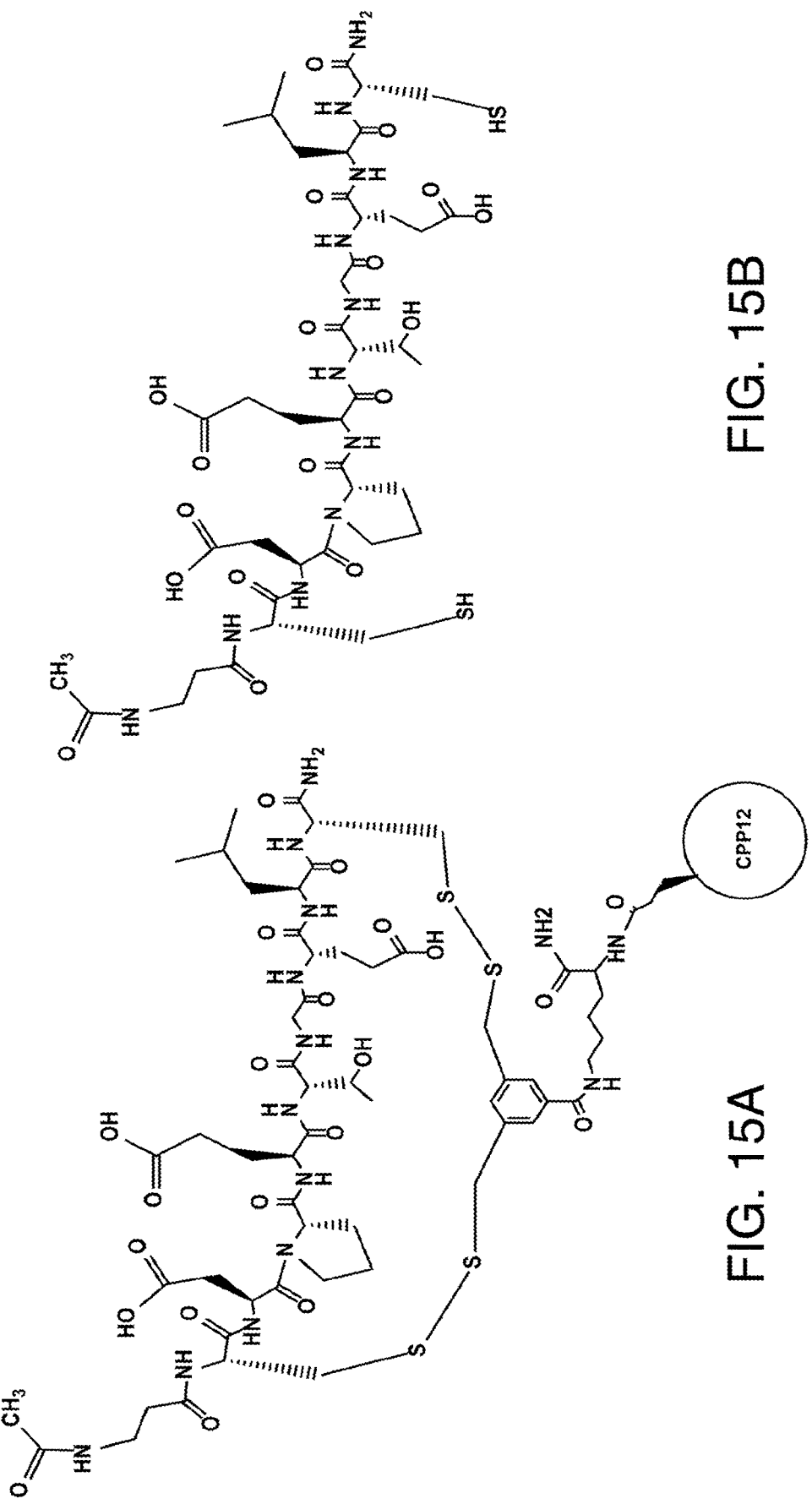
FIG. 15A shows the structure of a bicyclic peptide comprising cyclic comprising a cyclic CPP12 (FfΦRrRr) conjugated to a peptidyl inhibitor against Keap1-Nrf2.
FIG. 15B shows a structure of the linear peptidyl inhibitor against Keap1-Nrf2 in the absence of a cyclic CPP.
Figure 16:
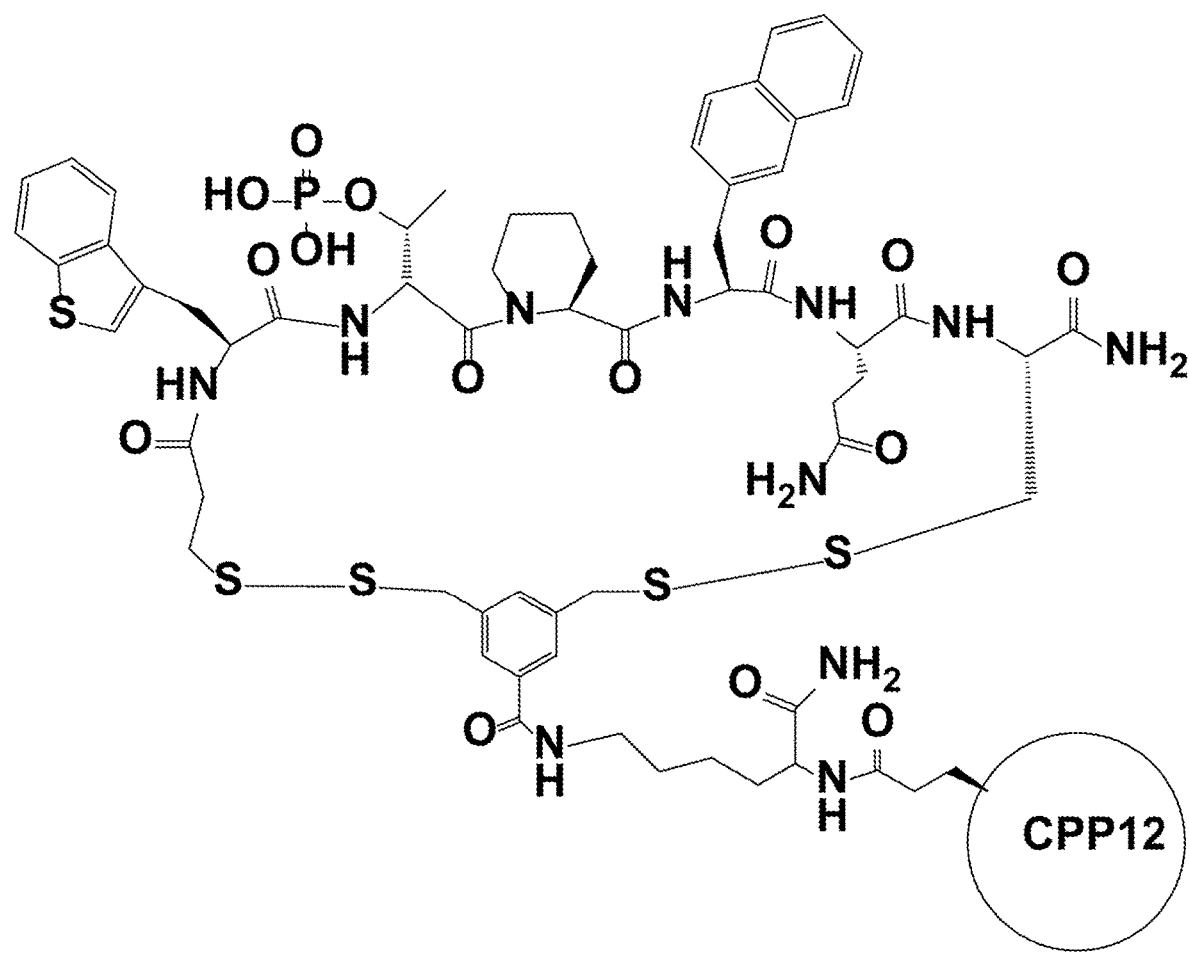
FIG. 16 shows the structure of a bicyclic peptide comprising cyclic comprising a cyclic CPP12 (FfΦRrRr) conjugated to a peptidyl inhibitor against Pin1.

Various bicyclic peptides synthesized according to Scheme 2. Specifically, cyclic CPP12 (FfΦRrRr) was conjugated to a peptidyl inhibitor against Keap1-Nrf2 (FIG. 10A), a peptidyl inhibitor against Pin1 (FIG. 11), peptidyl inhibitor against the CAL PDZ-CFTR (PDZ) interaction (FIG. 12A), and a peptidyl inhibitor against the MDM2-p53 interaction (PMI) (FIG. 13A). Fluorescent labels were attached using methods known in the art as necessary to quantify cellular uptake efficiency.

Cellular Uptake Assay.

The various bicyclic peptides (cyclic CPP+peptidyl cargo) synthesized according to Scheme 2 were assayed for cellular uptake efficiency using flow cytometry and compared to cellular uptake efficiency of linear peptidyl cargo (without the cyclic CPP).

All measurements were performed in triplicates and in the presence of 10% fetal bovine serum (FBS). Attachment of a cargo peptide (e.g., a negatively charged peptide such as the Keap1 peptide) increases the cellular uptake (relative to CPP12).

Serum Stability.

Figure 17:
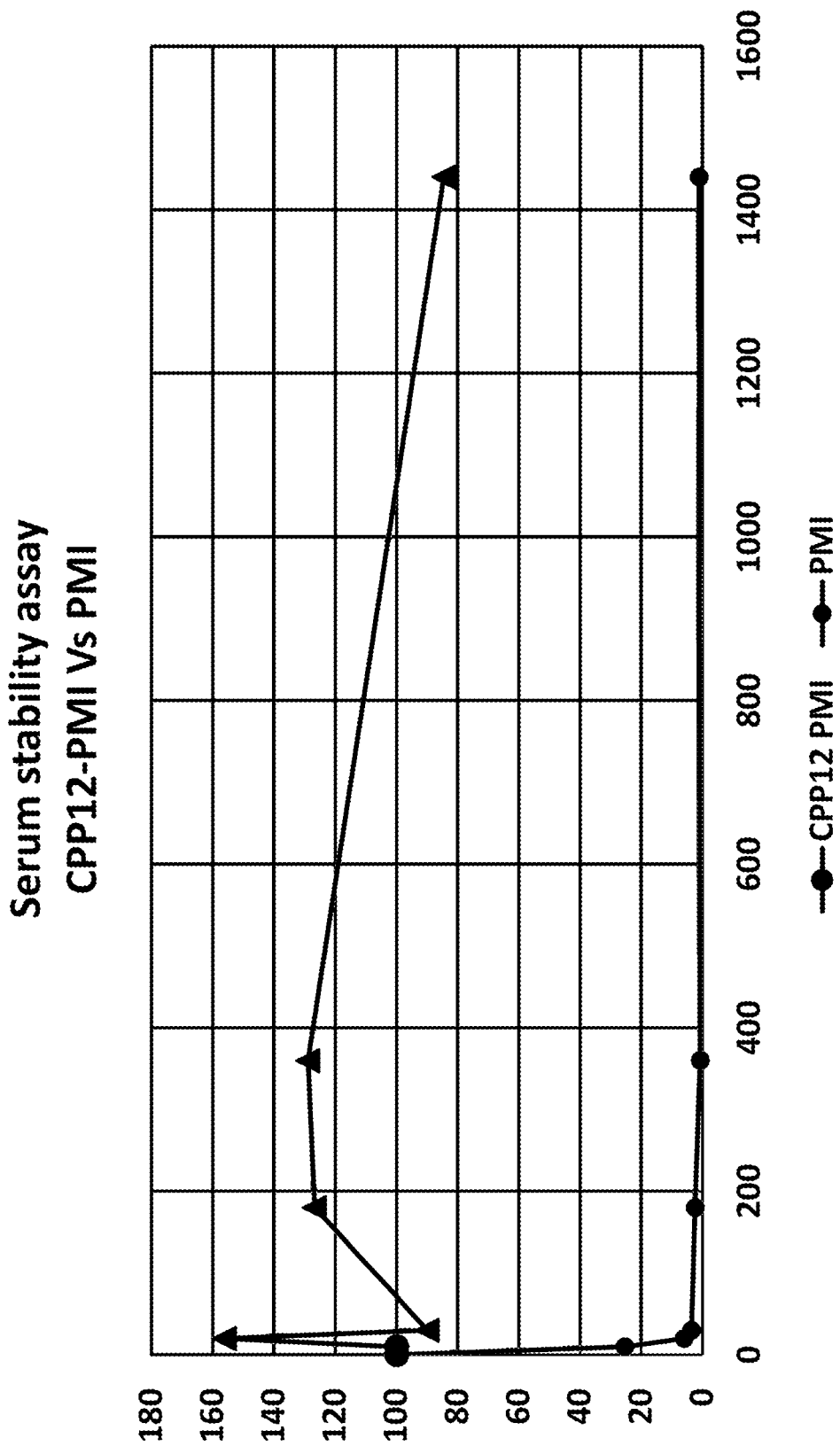
FIG. 17 graphically illustrates the serum stability of bicyclic peptide comprising a cyclic CPP12 (FfΦRrRr) conjugated to a peptidyl inhibitor against the MDM2-p53 interaction (PMI), compared to that of the linear peptidyl inhibitor against the PMI.
Figure 18:
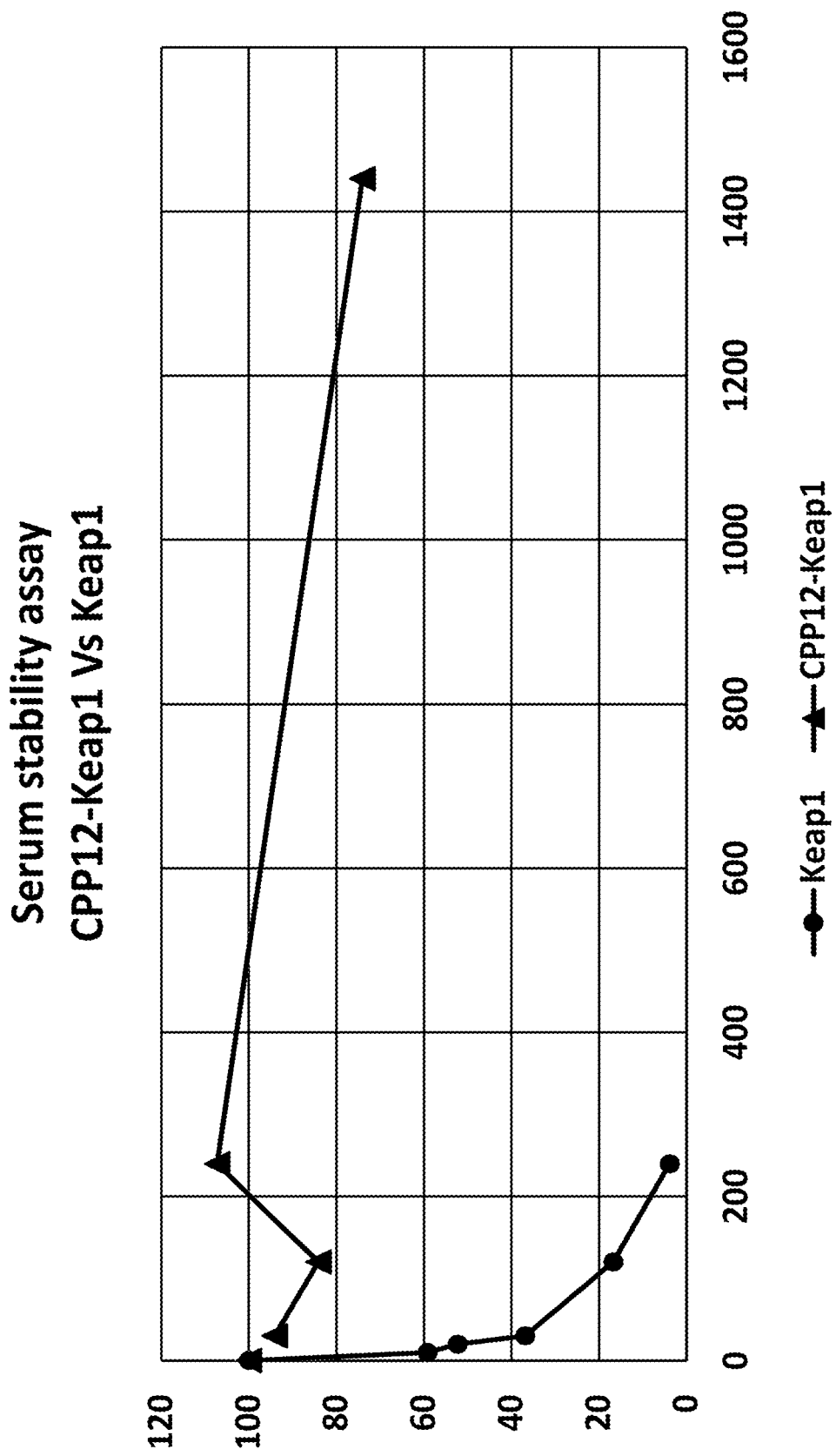
FIG. 18 graphically illustrates the serum stability of a bicyclic peptide comprising cyclic CPP12 (FfΦRrRr) conjugated to a peptidyl inhibitor against the Keap1-Nrf2 interaction, compared to that of the linear peptidyl inhibitor against the Keap1-Nrf2.
Figure 19:
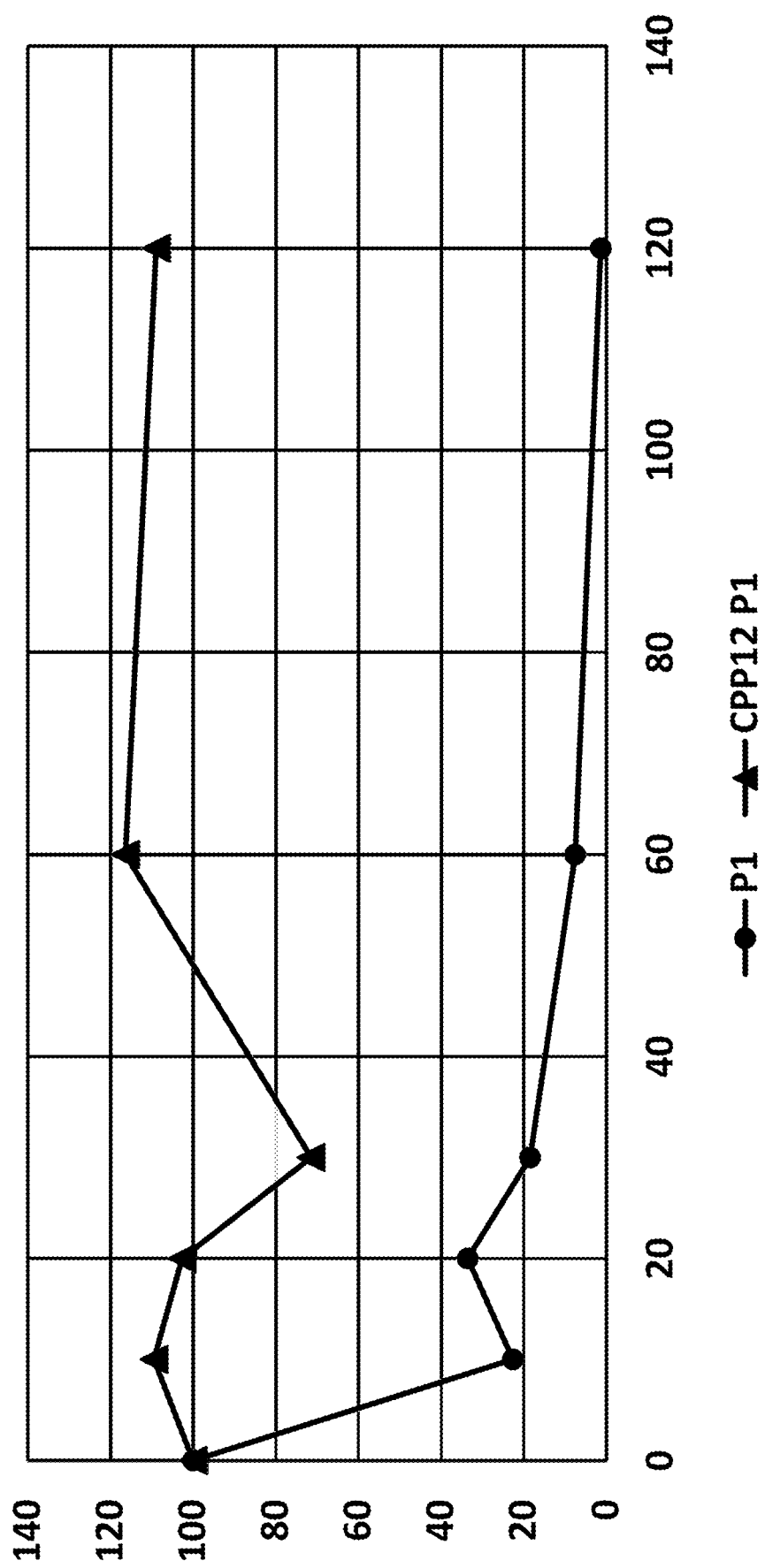
FIG. 19 graphically illustrates the serum stability of a bicyclic peptide comprising CPP12 (FfΦRrRr) conjugated to a peptidyl inhibitor against Pin-1 (P1), compared to that of linear peptidyl inhibitor against P1.

The serum stability of the bicyclic peptides (cyclic CPP+peptidyl cargo) synthesized according to Scheme 2 were assayed and compared to cellular uptake efficiency of linear peptidyl cargo (without the cyclic CPP). Unconjugated peptides and CPP12-peptide conjugates were incubated in 25% human serum for varying periods of time (min) and the remaining intact peptide was quantitated by analytical HPLC. Specifically, the serum stability of a bicyclic peptide comprising a cyclic CPP12 (FfΦRrRr) conjugated to a peptidyl inhibitor against the MDM2-p53 interaction (PMI) (FIG. 17), or conjugated to a peptidyl inhibitor against the Keap1-Nrf2 interaction (FIG. 18), or conjugated to a peptidyl inhibitor against Pin-1 (P1) (FIG. 19), compared serum stability of the respective linear peptidyl inhibitors.

Conjugation with CPP12 (via cyclization) greatly increases serum stability of all peptides.

Those skilled in the art will recognize, or be able to ascertain using no more than routine experimentation, many equivalents to the specific embodiments of the invention described herein. Such equivalents are intended to be encompassed by the following claims.

What is claimed is:
1. A bicyclic peptide selected from the group consisting of:
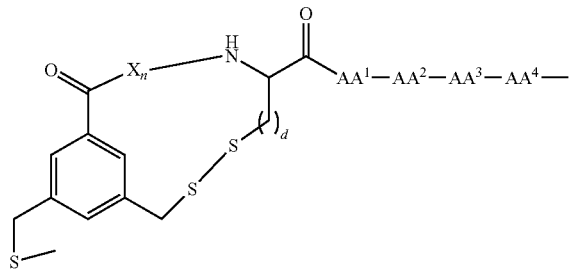
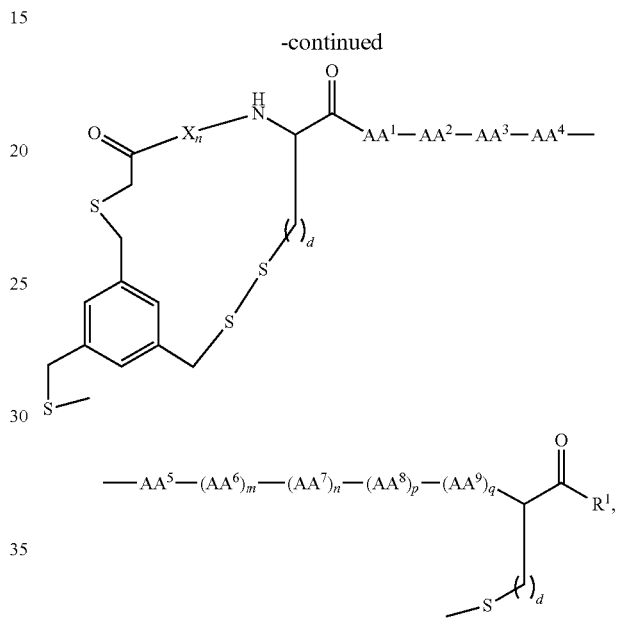
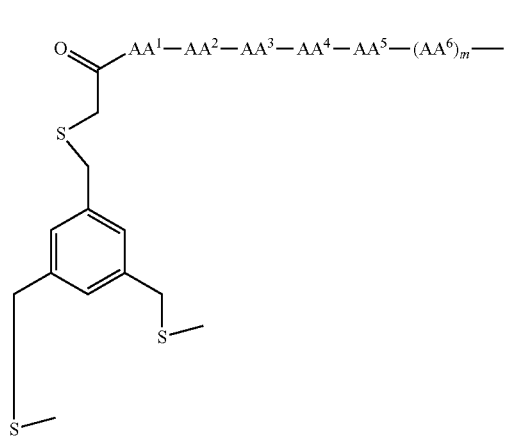
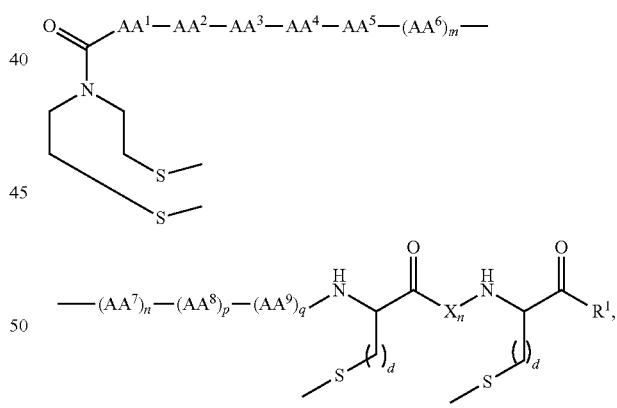
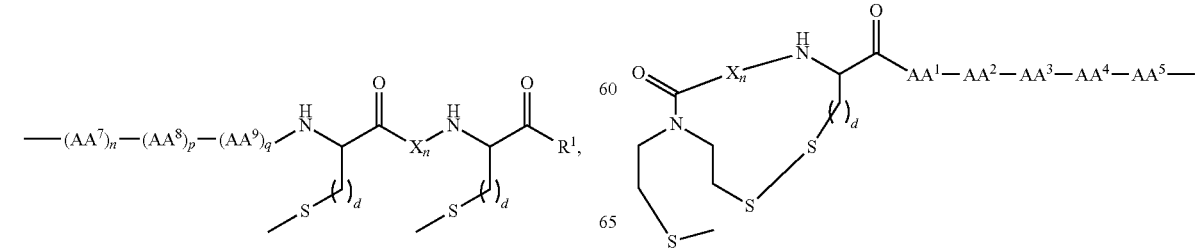

or a pharmaceutically acceptable salt thereof,
wherein:
AA$^1$, AA$^2$, AA$^3$, AA$^4$, AA$^5$, AA$^6$, AA$^7$, AA$^8$, and AA$^9$ are each independently an amino acid, wherein at least two of AA$^1$, AA$^2$, AA$^3$, AA$^4$, AA$^5$, AA$^6$, AA$^7$, AA$^8$, and AA$^9$ are arginine and at least two of AA$^1$, AA$^2$, AA$^3$, AA$^4$, AA$^5$, AA$^6$, AA$^7$, AA$^8$, and AA$^9$ independently comprise a hydrophobic side chain;
m, n, p, and q are independently selected from 0 and 1;
X$_n$ is a cargo moiety comprising a peptide sequence having from 1 to 20 amino acids;
wherein each d is independently 1 or 2; and
wherein R$^1$ is OH, OR$^2$, NHR$^2$; and R$^2$ is a alkyl, aryl, heteroaryl, amino acid, peptide sequence of 2 to 20 amino acid, detectable moiety, or solid support.

2. The bicyclic peptide of claim 1, wherein the at least two amino acid which independently comprise a hydrophobic side chain are selected from the group consisting of glycine, phenylglycine, alanine, valine, leucine, isoleucine, norleucine, phenylalanine, tryptophan, naphthylalanine, proline, and combinations thereof, wherein the aromatic side chains on phenylglycine, phenylalanine, tryptophan, or naphthylalanine are each optionally substituted with a halogen.

3. The bicyclic peptide of claim 2, wherein the at least two amino acid which independently comprise a hydrophobic side chain are independently selected from the group consisting of phenylalanine, naphthylalanine, and combinations thereof.

4. The bicyclic peptide of claim 1, wherein the at least two amino acids which independently comprise a hydrophobic residue are consecutive amino acids.

5. The bicyclic peptide of claim 1, wherein:
AA$^1$ is L-arginine;
AA$^2$ is L-arginine;
AA$^3$ is L-arginine;
AA$^4$ is L-naphthylalanine;
AA$^5$ is L-phenylalanine; and
m, n, p, and q, are each 0.

6. The bicyclic peptide of claim 1, wherein:
AA$^1$ is L-phenylalanine;
AA$^2$ is L-naphthylalanine;
AA$^3$ is L-arginine;
AA$^4$ is L-arginine;
AA$^5$ is L-arginine;
m is 1 and AA$^6$ is L-arginine; and
n, p, and q are each 0.

7. The bicyclic peptide of claim 1, wherein:
AA$^1$ is L-arginine;
AA$^2$ is L-arginine;
AA$^3$ is L-arginine;
AA$^4$ is L-arginine;
AA$^5$ is L-naphthylalanine;
m is 1 and AA$^6$ is L-phenylalanine; and
n, p, and q are each 0.

8. The bicyclic peptide of claim 1, wherein at least three consecutive amino acids have alternating chirality.

9. The bicyclic peptide of claim 8, wherein the at least three consecutive amino acids having alternating chirality are arginines.

10. The bicyclic peptide of claim 9, wherein:
AA$^1$ is D-phenylalanine;
AA$^2$ is L-naphthylalanine;
AA$^3$ is L-arginine;
AA$^4$ is D-arginine;
AA$^5$ is L-arginine;
m is 1 and AA$^6$ is D-arginine; and
n, p, and q are each 0.

11. The bicyclic peptide of claim 9, wherein:
AA$^1$ is D-phenylalanine;
AA$^2$ is L-naphthylalanine;
AA$^3$ is L-arginine;
AA$^4$ is D-arginine;
AA$^5$ is L-arginine;
m and n are each 1, and AA$^6$ is D-arginine and AA$^7$ is L-arginine; and
p and q are each 0.

12. The bicyclic peptide of claim 9, wherein:
AA$^1$ is L-phenylalanine;
AA$^2$ is D-phenylalanine;
AA$^3$ is L-naphthylalanine;
AA$^4$ is L-arginine;
AA$^5$ is D-arginine;
m and n are each 1, and AA$^6$ is L-arginine and AA$^7$ is D-arginine; and
p and q are each 0.

13. The bicyclic peptide of claim 1, wherein the peptide sequence in X$_n$ inhibits at least one protein-protein interaction.

14. The bicyclic peptide of claim 13, wherein the protein-protein interaction is an interaction between a IκB-kinase (IKK) complex and a regulatory protein NF-κB essential modifier (NEMO).

15. The bicyclic peptide of claim 13, wherein the peptide sequence in X$_n$ is an inhibitor against Ras, PTP1 B, Pin 1, Grb2 SH2, MDM2, or combinations thereof.

16. The bicyclic peptide of claim 1, wherein the peptide sequence in X$_n$ is a wild-type peptidyl ligand or a peptide mimetic.

17. A method for delivering a therapeutic agent to cytoplasm of a cell, comprising administering a compound of claim 1.

18. The compound of claim 1, wherein AA$^1$, AA$^2$, AA$^3$, AA$^4$, AA$^5$, AA$^6$, AA$^7$, AA$^8$, and AA$^9$ is selected from any one of SEQ ID NOS: 64-99, 102-118, and 120-146.

* * * * *

UNITED STATES PATENT AND TRADEMARK OFFICE
CERTIFICATE OF CORRECTION

PATENT NO. : 11,351,222 B2
APPLICATION NO. : 16/348706
DATED : June 7, 2022
INVENTOR(S) : Dehua Pei and Ziqing Qian It is certified that error appears in the above-identified patent and that said Letters Patent is hereby corrected as shown below:

In the Claims

Claim 17, Column 206, Line 21, delete "compound" and insert -- bicyclic peptide --.

Claim 18, Column 206, Line 23, delete "compound" and insert -- bicyclic peptide --.

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 214

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

His Lys Gly Phe Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Ala Phe Trp Thr Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-Nle

<400> SEQUENCE: 3

His Ala Leu Xaa
1

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
```

```
<223> OTHER INFORMATION: L-phenylglycine
<220> FEATURE:
<221> NAME/KEY: MOD_RES
<222> LOCATION: (10)..(10)
<223> OTHER INFORMATION: L-2,3-diaminopropionic acid

<400> SEQUENCE: 4

Xaa Tyr Ala Lys Tyr Phe Gly Lys His Xaa
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: L-Nle
<220> FEATURE:
<221> NAME/KEY: MOD_RES
<222> LOCATION: (11)..(11)
<223> OTHER INFORMATION: L-2,3-diaminopropionic acid

<400> SEQUENCE: 5

Ala Phe Trp Thr Glu Lys Xaa Leu Ala His Xaa
 1               5                  10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-2,3-diaminopropionic acid
<220> FEATURE:
<221> NAME/KEY: MOD_RES
<222> LOCATION: (8)..(8)
<223> OTHER INFORMATION: L-2,3-diaminopropionic acid

<400> SEQUENCE: 6

Phe Xaa Ser Val Pro Tyr His Xaa
 1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: L-2,3-diaminopropionic acid

<400> SEQUENCE: 7

Trp Phe Asp Lys Phe Asn His Xaa
 1               5

<210> SEQ ID NO 8
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

```
<222> LOCATION: (1)..(1)
<223> OTHER INFORMATION: D-amino acid

<400> SEQUENCE: 8

Xaa
1

<210> SEQ ID NO 9
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 9

Xaa
1

<210> SEQ ID NO 10
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 10

Xaa
1

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Arg Phe Glx Glx Phe Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine

<400> SEQUENCE: 12

Arg Asp Xaa Glx Asn Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct
```

-continued

```
<400> SEQUENCE: 13

Glx Glx Pro Gly Ala Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Glx Glx Ala Ser Ala Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Glx Glx Leu Pro Thr Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine

<400> SEQUENCE: 16

Xaa Arg Asn Glx Ile Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Glx Thr Glu Ala Asn Lys
1               5

<210> SEQ ID NO 18
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 18

Xaa
1
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine

<400> SEQUENCE: 19

Glx Xaa Ser Glx Glx Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine

<400> SEQUENCE: 20

Glx Xaa Met Ser Glx Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Glx Ser Met Glx Gly Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine

<400> SEQUENCE: 22

Glx Ser Xaa Glx Glx Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Glx Arg Val Asp Ala Lys
1               5

<210> SEQ ID NO 24
```

-continued

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (4)..(4)
<223> OTHER INFORMATION: L-propargylglycine

<400> SEQUENCE: 24

Arg Asp Xaa Xaa Asn
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-naphthylalanine
<220> FEATURE:
<221> NAME/KEY: MOD_RES
<222> LOCATION: (6)..(6)
<223> OTHER INFORMATION: L-2,3-diaminopropionic acid

<400> SEQUENCE: 25

Xaa Arg Arg Arg Arg Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine
<220> FEATURE:
<221> NAME/KEY: MOD_RES
<222> LOCATION: (4)..(4)
<223> OTHER INFORMATION: L-propargylglycine

<400> SEQUENCE: 26

Xaa Arg Asn Xaa Ile
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MOD_RES
<222> LOCATION: (3)..(3)
<223> OTHER INFORMATION: L-phenylglycine

<400> SEQUENCE: 27
```

```
Xaa Ser Xaa Lys Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-propargylglycine

<400> SEQUENCE: 28

Xaa Arg Val Asp Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine

<400> SEQUENCE: 29

Ala Xaa Arg Asn Xaa Ile
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine
<220> FEATURE:
<221> NAME/KEY: MOD_RES
<222> LOCATION: (4)..(4)
<223> OTHER INFORMATION: L-propargylglycine

<400> SEQUENCE: 30

Xaa Arg Asn Xaa Ile Ala
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine

<400> SEQUENCE: 31
```

```
Ala Xaa Arg Asn Xaa Ile Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 32

Ala Ala Xaa Arg Asn Xaa Ile Ala
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 33

Ala Phe Xaa Arg Asn Xaa Ile Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine
<220> FEATURE:
<221> NAME/KEY: MOD_RES
<222> LOCATION: (8)..(8)
<223> OTHER INFORMATION: Aminobutyric acid

<400> SEQUENCE: 34

Ala Xaa Xaa Arg Asn Xaa Ile Xaa
1               5

<210> SEQ ID NO 35
<211> LENGTH: 9
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine
<220> FEATURE:
<221> NAME/KEY: MOD_RES
<222> LOCATION: (8)..(8)
<223> OTHER INFORMATION: Aminobutyric acid

<400> SEQUENCE: 35

Xaa Ile Xaa Arg Asn Xaa Ile Xaa Lys
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine
<220> FEATURE:
<221> NAME/KEY: MOD_RES
<222> LOCATION: (7)..(7)
<223> OTHER INFORMATION: Aminobutyric acid

<400> SEQUENCE: 36

Xaa Xaa Arg Asn Xaa Ile Xaa
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 37

Ala Leu Xaa Arg Asn Xaa Ile Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 38

Ala Gln Xaa Arg Asn Xaa Ile Asp
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 39

Ile Glu Xaa Arg Asn Xaa Ile Asp
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 40

Ala Ser Xaa Arg Asn Xaa Ile Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine

<400> SEQUENCE: 41

Leu Xaa Arg Asn Xaa Ile Glu
1               5

<210> SEQ ID NO 42
<211> LENGTH: 10
```

```
-continued

<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(3)
<223> OTHER INFORMATION: L-phenylglycine

<400> SEQUENCE: 42

Ala Xaa Xaa Arg Asn Pro Arg Ala Ile Phe
1               5                   10

<210> SEQ ID NO 43
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-Ornithine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 43

Ala Xaa Xaa Arg Asn Xaa Ile Phe
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 44

Ala Xaa Xaa Arg Asn Xaa Ile Asn
1               5

<210> SEQ ID NO 45
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 45

Xaa
```

```
<210> SEQ ID NO 46
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 46

Xaa Asn Xaa Arg Asn Xaa Ile Ile
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine
<220> FEATURE:
<221> NAME/KEY: MOD_RES
<222> LOCATION: (8)..(8)
<223> OTHER INFORMATION: L-norleucine

<400> SEQUENCE: 47

Ala Xaa Xaa Arg Asn Xaa Ile Xaa
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine
<220> FEATURE:
<221> NAME/KEY: MOD_RES
<222> LOCATION: (7)..(7)
<223> OTHER INFORMATION: L-phenylglycine

<400> SEQUENCE: 48

Trp Xaa Arg Asn Xaa Ile Xaa
```

```
<210> SEQ ID NO 49
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 49

Ala Asn Xaa Arg Asn Xaa Ile Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-norleucine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 50

Arg Xaa Xaa Arg Asn Xaa Ile Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (5)..(5)
<223> OTHER INFORMATION: L-propargylglycine
<220> FEATURE:
<221> NAME/KEY: MOD_RES
<222> LOCATION: (9)..(9)
<223> OTHER INFORMATION: L-naphthylalanine

<400> SEQUENCE: 51

His Xaa Arg Asn Xaa Ile Tyr Lys Xaa
1               5

<210> SEQ ID NO 52
<211> LENGTH: 8
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine
<220> FEATURE:
<221> NAME/KEY: MOD_RES
<222> LOCATION: (8)..(8)
<223> OTHER INFORMATION: Aminobutyric acid

<400> SEQUENCE: 52

Ala Xaa Xaa Arg Asn Xaa Ile Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine
<220> FEATURE:
<221> NAME/KEY: MOD_RES
<222> LOCATION: (8)..(8)
<223> OTHER INFORMATION: Aminobutyric acid

<400> SEQUENCE: 53

Xaa Ile Xaa Arg Asn Xaa Ile Xaa
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 54

Ala Leu Xaa Arg Asn Xaa Ile Asp
1               5

<210> SEQ ID NO 55
<211> LENGTH: 8
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 55

Ala Gln Xaa Arg Asn Xaa Ile Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-Ornithine
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 56

Ala Xaa Xaa Arg Asn Xaa Ile Phe
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 57

Ala Xaa Xaa Arg Asn Xaa Ile Phe
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Aminobutyric acid
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
```

<223> OTHER INFORMATION: L-propargylglycine
<220> FEATURE:
<221> NAME/KEY: MOD_RES
<222> LOCATION: (8)..(8)
<223> OTHER INFORMATION: Aminobutyric acid

<400> SEQUENCE: 58

Ala Xaa Xaa Arg Asn Xaa Ile Xaa
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (6)..(6)
<223> OTHER INFORMATION: L-propargylglycine

<400> SEQUENCE: 59

Ala Ala Xaa Arg Asn Xaa Ile Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-propargylglycine

<400> SEQUENCE: 60

Ala Ala Phe Arg Asn Xaa Ile Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-propargylglycine

<400> SEQUENCE: 61

Ala Leu Phe Arg Asn Xaa Ile Asp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-phenylglycine

<400> SEQUENCE: 62

```
Xaa Tyr Ala Lys Tyr Phe Gly Lys His
1               5
```

<210> SEQ ID NO 63
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: L-norleucine

<400> SEQUENCE: 63

```
Ala Phe Trp Thr Glu Lys Xaa Leu Ala His
1               5                   10
```

<210> SEQ ID NO 64
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 64

```
Phe Xaa Arg Arg Arg
1               5
```

<210> SEQ ID NO 65
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 65

```
Phe Xaa Arg Arg Arg Cys
1               5
```

<210> SEQ ID NO 66
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: MOD_RES
<222> LOCATION: (6)..(6)
<223> OTHER INFORMATION: Selenocysteine

<400> SEQUENCE: 66

```
Phe Xaa Arg Arg Arg Xaa
1               5
```

<210> SEQ ID NO 67
<211> LENGTH: 5

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-naphthylalanine

<400> SEQUENCE: 67

Arg Arg Arg Xaa Phe
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-naphthylalanine

<400> SEQUENCE: 68

Arg Arg Arg Arg Xaa Phe
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 69

Phe Xaa Arg Arg Arg Arg
1               5

<210> SEQ ID NO 70
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 70

Xaa
1

<210> SEQ ID NO 71
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 71
```

```
Xaa
1

<210> SEQ ID NO 72
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 72

Phe Xaa Arg Arg Arg Arg
1               5

<210> SEQ ID NO 73
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 73

Xaa
1

<210> SEQ ID NO 74
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-naphthylalanine

<400> SEQUENCE: 74

Arg Arg Phe Arg Xaa Arg
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: L-naphthylalanine

<400> SEQUENCE: 75

Phe Arg Arg Arg Arg Xaa
1               5

<210> SEQ ID NO 76
<211> LENGTH: 1
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MOD_RES
<222> LOCATION: (1)..(1)
<223> OTHER INFORMATION: D-amino acid

<400> SEQUENCE: 76

Xaa
1

<210> SEQ ID NO 77
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-naphthylalanine

<400> SEQUENCE: 77

Arg Arg Xaa Phe Arg Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Construct

<400> SEQUENCE: 78

Cys Arg Arg Arg Arg Phe Trp
1               5

<210> SEQ ID NO 79
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 79

Xaa
1

<210> SEQ ID NO 80
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-naphthylalanine

<400> SEQUENCE: 80

Phe Phe Xaa Arg Arg Arg Arg
1               5

<210> SEQ ID NO 81
<211> LENGTH: 7
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (6)..(6)
<223> OTHER INFORMATION: L-naphthylalanine

<400> SEQUENCE: 81

Arg Phe Arg Phe Arg Xaa Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Selenocysteine

<400> SEQUENCE: 82

Xaa Arg Arg Arg Arg Phe Trp
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Cys Arg Arg Arg Arg Phe Trp
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 84

Phe Xaa Arg Arg Arg Arg Gln Lys
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 85

Phe Xaa Arg Arg Arg Arg Gln Cys
1               5

<210> SEQ ID NO 86
<211> LENGTH: 1
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 86

Xaa
1

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 87

Phe Xaa Arg Arg Arg Arg Arg
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-naphthylalanine
<220> FEATURE:
<221> NAME/KEY: MOD_RES
<222> LOCATION: (8)..(8)
<223> OTHER INFORMATION: L-norleucine

<400> SEQUENCE: 88

Arg Arg Arg Arg Xaa Phe Asp Xaa Cys
1               5

<210> SEQ ID NO 89
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 89

Phe Xaa Arg Arg Arg
1               5

<210> SEQ ID NO 90
<211> LENGTH: 5
<212> TYPE: PRT
<213> ORGANISM: Artificial Sequence
<220> FEATURE:
<223> OTHER INFORMATION: Synthetic Construct

<400> SEQUENCE: 90

Phe Trp Arg Arg Arg
```

```
1               5
```

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: misc_feature
<222> LOCATION: (4)..(4)
<223> OTHER INFORMATION: Xaa can be any naturally occurring amino acid

<400> SEQUENCE: 91

```
Arg Arg Arg Xaa Phe
1               5
```

<210> SEQ ID NO 92
<211> LENGTH: 5
<212> TYPE: PRT
<213> ORGANISM: Artificial Sequence
<220> FEATURE:
<223> OTHER INFORMATION: Synthetic Construct

<400> SEQUENCE: 92

```
Arg Arg Arg Trp Phe
1               5
```

<210> SEQ ID NO 93
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 93

```
Phe Xaa Arg Arg Arg Arg
1               5
```

<210> SEQ ID NO 94
<211> LENGTH: 5
<212> TYPE: PRT
<213> ORGANISM: Artificial Sequence
<220> FEATURE:
<223> OTHER INFORMATION: Synthetic Construct

<400> SEQUENCE: 94

```
Phe Phe Arg Arg Arg
1               5
```

<210> SEQ ID NO 95
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 95

```
Xaa
1

<210> SEQ ID NO 96
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 96

Xaa
1

<210> SEQ ID NO 97
<211> LENGTH: 5
<212> TYPE: PRT
<213> ORGANISM: Artificial Sequence
<220> FEATURE:
<223> OTHER INFORMATION: Synthetic Construct

<400> SEQUENCE: 97

Phe Arg Phe Arg Arg
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Construct

<400> SEQUENCE: 98

Phe Arg Arg Phe Arg
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Construct

<400> SEQUENCE: 99

Phe Arg Arg Arg Phe
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 100

Gly Xaa Arg Arg Arg
1               5

<210> SEQ ID NO 101
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 101

Phe Phe Phe Arg Ala
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Construct

<400> SEQUENCE: 102

Phe Phe Phe Arg Arg
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Construct

<400> SEQUENCE: 103

Phe Phe Arg Arg Arg Arg
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic Construct

<400> SEQUENCE: 104

Phe Arg Arg Phe Arg Arg
1               5

<210> SEQ ID NO 105
<211> LENGTH: 6
<212> TYPE: PRT
<213> ORGANISM: Artificial Sequence
<220> FEATURE:
<223> OTHER INFORMATION: Synthetic Construct

<400> SEQUENCE: 105

Phe Arg Arg Arg Phe Arg
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic Construct

<400> SEQUENCE: 106

Arg Phe Phe Arg Arg Arg
1               5

<210> SEQ ID NO 107
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 107

Arg Phe Arg Arg Phe Arg
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic Construct

<400> SEQUENCE: 108

Phe Arg Phe Arg Arg Arg
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic Construct

<400> SEQUENCE: 109

Phe Phe Phe Arg Arg Arg
1               5

<210> SEQ ID NO 110
<211> LENGTH: 6
<212> TYPE: PRT
<213> ORGANISM: Artificial Sequence
<220> FEATURE:
<223> OTHER INFORMATION: Synthetic Construct

<400> SEQUENCE: 110

Phe Phe Arg Arg Arg Phe
1               5

<210> SEQ ID NO 111
<211> LENGTH: 6
<212> TYPE: PRT
<213> ORGANISM: Artificial Sequence
<220> FEATURE:
<223> OTHER INFORMATION: Synthetic Construct

<400> SEQUENCE: 111

Phe Arg Phe Phe Arg Arg
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic Construct

<400> SEQUENCE: 112

Arg Arg Phe Phe Phe Arg
1               5

<210> SEQ ID NO 113
<211> LENGTH: 6
<212> TYPE: PRT
```

```
<213> ORGANISM: Artificial Sequence
<220> FEATURE:
<223> OTHER INFORMATION: Synthetic Construct

<400> SEQUENCE: 113

Phe Phe Arg Phe Arg Arg
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic Construct

<400> SEQUENCE: 114

Phe Phe Arg Arg Phe Arg
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic Construct

<400> SEQUENCE: 115

Phe Arg Arg Phe Phe Arg
1               5

<210> SEQ ID NO 116
<211> LENGTH: 6
<212> TYPE: PRT
<213> ORGANISM: Artificial Sequence
<220> FEATURE:
<223> OTHER INFORMATION: Synthetic Construct

<400> SEQUENCE: 116

Phe Arg Arg Phe Arg Phe
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic Construct

<400> SEQUENCE: 117

Phe Arg Phe Arg Phe Arg
1               5

<210> SEQ ID NO 118
<211> LENGTH: 6
<212> TYPE: PRT
<213> ORGANISM: Artificial Sequence
<220> FEATURE:
<223> OTHER INFORMATION: Synthetic Construct

<400> SEQUENCE: 118

Arg Phe Phe Arg Phe Arg
1               5

<210> SEQ ID NO 119
<211> LENGTH: 6
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-naphthylalanine

<400> SEQUENCE: 119

Gly Xaa Arg Arg Arg Arg
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic Construct

<400> SEQUENCE: 120

Phe Phe Phe Arg Arg Arg Arg
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic Construct

<400> SEQUENCE: 121

Arg Phe Phe Arg Arg Arg Arg
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic Construct

<400> SEQUENCE: 122

Arg Arg Phe Phe Arg Arg Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic Construct

<400> SEQUENCE: 123

Arg Phe Phe Phe Arg Arg Arg
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic Construct

<400> SEQUENCE: 124

Arg Arg Phe Phe Phe Arg Arg
1               5

<210> SEQ ID NO 125
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 125

Phe Phe Arg Arg Phe Arg Arg
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic Construct

<400> SEQUENCE: 126

Phe Phe Arg Arg Arg Arg Phe
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic Construct

<400> SEQUENCE: 127

Phe Arg Arg Phe Phe Arg Arg
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Phe Phe Phe Arg Arg Arg Arg Arg
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Phe Phe Phe Arg Arg Arg Arg Arg Arg
1               5

<210> SEQ ID NO 130
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 130

Xaa
1
```

<210> SEQ ID NO 131
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(2)
<223> OTHER INFORMATION: L-4-fluorophenylalanine

<400> SEQUENCE: 131

Xaa Xaa Arg Arg Arg Arg
1               5

<210> SEQ ID NO 132
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 132

Xaa
1

<210> SEQ ID NO 133
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 133

Xaa
1

<210> SEQ ID NO 134
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 134

Xaa
1

<210> SEQ ID NO 135
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)

```
<223> OTHER INFORMATION: D-amino acid

<400> SEQUENCE: 135

Xaa
1

<210> SEQ ID NO 136
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 136

Xaa
1

<210> SEQ ID NO 137
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 137

Xaa
1

<210> SEQ ID NO 138
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 138

Xaa
1

<210> SEQ ID NO 139
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 139

Xaa
1

<210> SEQ ID NO 140
<211> LENGTH: 1
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 140

Xaa
1

<210> SEQ ID NO 141
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 141

Xaa
1

<210> SEQ ID NO 142
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 142

Xaa
1

<210> SEQ ID NO 143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 143

Trp Trp Trp Arg Arg Arg Arg
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic Construct

<400> SEQUENCE: 144

Trp Trp Trp Arg Arg Arg Arg Arg
1               5

<210> SEQ ID NO 145
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 145

Phe Trp Arg Arg Arg Arg
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct

<400> SEQUENCE: 146

Trp Trp Trp Arg Arg Arg
1               5

<210> SEQ ID NO 147
<211> LENGTH: 5
<212> TYPE: PRT
<213> ORGANISM: Artificial Sequence
<220> FEATURE:
<223> OTHER INFORMATION: Synthetic Construct

<400> SEQUENCE: 147

Arg Arg Arg Arg Arg
1               5

<210> SEQ ID NO 148
<211> LENGTH: 5
<212> TYPE: PRT
<213> ORGANISM: Artificial Sequence
<220> FEATURE:
<223> OTHER INFORMATION: Synthetic Construct

<400> SEQUENCE: 148

Ala Ala Ala Ala Ala
1               5

<210> SEQ ID NO 149
<211> LENGTH: 4
<212> TYPE: PRT
<213> ORGANISM: Artificial Sequence
<220> FEATURE:
<223> OTHER INFORMATION: Synthetic Construct

<400> SEQUENCE: 149

Phe Phe Phe Phe
1

<210> SEQ ID NO 150
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: phosphocoumaryl amino propionic acid

<400> SEQUENCE: 150

Asp Glu Xaa Leu Ile
1               5

<210> SEQ ID NO 151
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 151

Ala Ala Ala Ala Ala Ala Ala
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct

<400> SEQUENCE: 152

Arg Ala Arg Ala Arg
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic Construct

<400> SEQUENCE: 153

Asp Ala Asp Ala Asp
1               5

<210> SEQ ID NO 154
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-norleucine
<220> FEATURE:
<221> NAME/KEY: MOD_RES
<222> LOCATION: (3)..(3)
<223> OTHER INFORMATION: 2-aminobutyric acid

<400> SEQUENCE: 154

Asp Xaa Xaa Asp
1

<210> SEQ ID NO 155
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MOD_RES
<222> LOCATION: (2)..(2)
<223> OTHER INFORMATION: 2-aminobutyric acid

<400> SEQUENCE: 155

Xaa Thr Arg Val
1
```

```
<210> SEQ ID NO 156
<211> LENGTH: 5
<212> TYPE: PRT
<213> ORGANISM: Artificial Sequence
<220> FEATURE:
<223> OTHER INFORMATION: Synthetic Construct

<400> SEQUENCE: 156

Ser Ala Ser Ala Ser
1               5

<210> SEQ ID NO 157
<211> LENGTH: 8
<212> TYPE: PRT
<213> ORGANISM: Artificial Sequence
<220> FEATURE:
<223> OTHER INFORMATION: Synthetic Construct

<400> SEQUENCE: 157

Ala Leu Asp Trp Ser Trp Leu Gln
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic Construct

<400> SEQUENCE: 158

Ala Leu Asp Ala Ser Ala Leu Gln
1               5

<210> SEQ ID NO 159
<211> LENGTH: 10
<212> TYPE: PRT
<213> ORGANISM: Artificial Sequence
<220> FEATURE:
<223> OTHER INFORMATION: Synthetic Construct

<400> SEQUENCE: 159

Ser Phe Ala Glu Tyr Trp Ala Leu Leu Ser
1               5                   10

<210> SEQ ID NO 160
<211> LENGTH: 29
<212> TYPE: PRT
<213> ORGANISM: Artificial Sequence
<220> FEATURE:
<223> OTHER INFORMATION: Synthetic Construct

<400> SEQUENCE: 160

Arg Gln Ile Lys Ile Trp Phe Gln Asn Arg Arg Met Lys Trp Lys Lys
1               5                   10                  15

Gly Gly Thr Ala Leu Asp Trp Ser Trp Leu Gln Thr Glu
            20                  25

<210> SEQ ID NO 161
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine
<220> FEATURE:
```

```
<221> NAME/KEY: MOD_RES
<222> LOCATION: (5)..(5)
<223> OTHER INFORMATION: L-2-naphthylalanine

<400> SEQUENCE: 161

Arg Arg Arg Arg Xaa Phe Cys Ser Ala Ser Ala Ser Cys Lys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: L-2-naphthylalanine

<400> SEQUENCE: 162

Ser Ala Ser Ala Ser Cys Phe Xaa Arg Arg Arg Arg Cys Lys
1               5                   10

<210> SEQ ID NO 163
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 163

Arg Arg Arg Arg Xaa Phe Cys Ala Leu Asp Trp Ser Trp Leu Gln Cys
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 164

Arg Arg Arg Arg Xaa Phe Cys Ala Leu Asp Ala Ser Ala Leu Gln Cys
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 165

Arg Arg Arg Arg Xaa Phe Cys Ala Leu Asp Trp Ser Trp Leu Gln
1               5                   10                  15

<210> SEQ ID NO 166
```

```
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: L-2-naphthylalanine

<400> SEQUENCE: 166

Arg Arg Arg Arg Xaa Phe Cys Ser Phe Ala Glu Tyr Trp Ala Leu Leu
1               5                   10                  15

Ser Cys

<210> SEQ ID NO 167
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (16)..(16)
<223> OTHER INFORMATION: L-2-naphthylalanine

<400> SEQUENCE: 167

Ser Phe Ala Glu Tyr Trp Ala Leu Leu Ser Cys Arg Arg Arg Arg Xaa
1               5                   10                  15

Phe Cys

<210> SEQ ID NO 168
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-homoproline
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 168

Pro Xaa Gly Xaa Tyr
1               5

<210> SEQ ID NO 169
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-homoproline
<220> FEATURE:
<221> NAME/KEY: MOD_RES
<222> LOCATION: (4)..(5)
<223> OTHER INFORMATION: L-4-(phosphonodifluoromethyl)phenylalanine

<400> SEQUENCE: 169

Ser Xaa Ile Xaa Xaa
1               5
```

```
<210> SEQ ID NO 170
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 170

Ile His Ile Xaa Ile
1               5

<210> SEQ ID NO 171
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 171

Xaa
1

<210> SEQ ID NO 172
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 172

Xaa
1

<210> SEQ ID NO 173
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 173

Xaa
1

<210> SEQ ID NO 174
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
```

-continued

```
<221> NAME/KEY: MOD_RES
<222> LOCATION: (4)..(4)
<223> OTHER INFORMATION: L-4-(phosphonodifluoromethyl)phenylalanine

<400> SEQUENCE: 174

Thr Xaa Ala Xaa Gly
1               5

<210> SEQ ID NO 175
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 175

Xaa
1

<210> SEQ ID NO 176
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 176

Xaa
1

<210> SEQ ID NO 177
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 177

Xaa
1

<210> SEQ ID NO 178
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 178

Ser Pro Gly Xaa His
1               5

<210> SEQ ID NO 179
```

```
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 179

Xaa Tyr Ile Xaa His
1               5

<210> SEQ ID NO 180
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 180

Xaa
1

<210> SEQ ID NO 181
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 181

Xaa
1

<210> SEQ ID NO 182
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: L-4-fluorophenylalanine
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 182

Xaa Ser Ile Xaa Gln Phe
1               5

<210> SEQ ID NO 183
<211> LENGTH: 1
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 183

Xaa
1

<210> SEQ ID NO 184
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 184

Xaa
1

<210> SEQ ID NO 185
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: L-phenylglycine
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (5)..(5)
<223> OTHER INFORMATION: L-norleucine

<400> SEQUENCE: 185

Ile Pro Xaa Xaa Xaa
1               5

<210> SEQ ID NO 186
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-homoproline
<220> FEATURE:
<221> NAME/KEY: MOD_RES
<222> LOCATION: (3)..(3)
<223> OTHER INFORMATION: L-4-fluorophenylalanine
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (5)..(5)
<223> OTHER INFORMATION: L-homoproline

<400> SEQUENCE: 186
```

```
Gln Xaa Xaa Xaa Xaa
1               5

<210> SEQ ID NO 187
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 187

Xaa
1

<210> SEQ ID NO 188
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 188

Xaa
1

<210> SEQ ID NO 189
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 189

Xaa
1

<210> SEQ ID NO 190
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 190

Xaa
1

<210> SEQ ID NO 191
<211> LENGTH: 1
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MOD_RES
<222> LOCATION: (1)..(1)
<223> OTHER INFORMATION: D-amino acid

<400> SEQUENCE: 191

Xaa
1

<210> SEQ ID NO 192
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 192

Xaa
1

<210> SEQ ID NO 193
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 193

Xaa
1

<210> SEQ ID NO 194
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 194

Xaa
1

<210> SEQ ID NO 195
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 195

Xaa
1
```

```
<210> SEQ ID NO 196
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 196

Xaa
1

<210> SEQ ID NO 197
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 197

Asn Thr Val Xaa Thr
1               5

<210> SEQ ID NO 198
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 198

Xaa
1

<210> SEQ ID NO 199
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 199

Xaa
1

<210> SEQ ID NO 200
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
```

```
<400> SEQUENCE: 200

Xaa
1

<210> SEQ ID NO 201
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 201

Xaa
1

<210> SEQ ID NO 202
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 202

Xaa
1

<210> SEQ ID NO 203
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 203

Xaa
1

<210> SEQ ID NO 204
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: L-phenylglycine
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (5)..(5)
<223> OTHER INFORMATION: L-homoproline

<400> SEQUENCE: 204

Pro Xaa His Xaa Xaa
```

```
<210> SEQ ID NO 205
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 205

Xaa
1

<210> SEQ ID NO 206
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 206

Pro Ala His Xaa Gly
1               5

<210> SEQ ID NO 207
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: L-4-(phosphonodifluoromethyl)phenylalanine

<400> SEQUENCE: 207

Ala Tyr His Xaa Ile
1               5

<210> SEQ ID NO 208
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 208

Xaa
1

<210> SEQ ID NO 209
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
```

-continued

```
<222> LOCATION: (1)..(1)
<223> OTHER INFORMATION: D-amino acid

<400> SEQUENCE: 209

Xaa
1

<210> SEQ ID NO 210
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 210

Xaa
1

<210> SEQ ID NO 211
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 211

Xaa
1

<210> SEQ ID NO 212
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 212

Xaa
1

<210> SEQ ID NO 213
<211> LENGTH: 1
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid

<400> SEQUENCE: 213

Xaa
1

<210> SEQ ID NO 214
<211> LENGTH: 1
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: D-amino acid
<400> SEQUENCE: 214
Xaa
1
```